United States Patent
Mansour et al.

(10) Patent No.: US 11,077,184 B2
(45) Date of Patent: *Aug. 3, 2021

(54) LIPOSOME COMPOSITIONS COMPRISING PAM2CYS OR PAM3CYS ADJUVANT AND METHODS FOR INDUCING A HUMORAL IMMUNE RESPONSE

(71) Applicant: IMMUNOVACCINE TECHNOLOGIES INC., Dartmouth (CA)

(72) Inventors: Marc Mansour, Halifax (CA); Lisa Diana MacDonald, Halifax (CA); Genevieve Mary Weir, Dartmouth (CA); Leeladhar Sammatur, Irvine, CA (US); Kendall Sharp, Halifax (CA)

(73) Assignee: IMMUNOVACCINE TECHNOLOGIES INC., Dartmouth (CA)

( * ) Notice: Subject to any disclaimer, the term of this patent is extended or adjusted under 35 U.S.C. 154(b) by 6 days.

This patent is subject to a terminal disclaimer.

(21) Appl. No.: 16/139,361

(22) Filed: Sep. 24, 2018

(65) Prior Publication Data

US 2019/0142928 A1 May 16, 2019

Related U.S. Application Data

(63) Continuation of application No. 14/347,928, filed as application No. PCT/CA2012/050705 on Oct. 5, 2012, now Pat. No. 10,105,435.

(60) Provisional application No. 61/544,020, filed on Oct. 6, 2011.

(51) Int. Cl.
| | |
|---|---|
| *A61K 39/395* | (2006.01) |
| *A61K 39/145* | (2006.01) |
| *A61K 9/127* | (2006.01) |
| *A61K 39/07* | (2006.01) |
| *A61K 39/02* | (2006.01) |
| *A61K 39/12* | (2006.01) |
| *A61K 39/39* | (2006.01) |
| *A61K 39/00* | (2006.01) |

(52) U.S. Cl.
CPC ............ *A61K 39/145* (2013.01); *A61K 9/127* (2013.01); *A61K 39/07* (2013.01); *A61K 39/099* (2013.01); *A61K 39/12* (2013.01); *A61K 39/39* (2013.01); *A61K 2039/5252* (2013.01); *A61K 2039/55511* (2013.01); *A61K 2039/55555* (2013.01); *A61K 2039/55566* (2013.01); *C12N 2760/16134* (2013.01)

(58) Field of Classification Search
None
See application file for complete search history.

(56) References Cited

U.S. PATENT DOCUMENTS

| | | |
|---|---|---|
| 3,906,092 A | 9/1975 | Hilleman |
| 4,610,868 A | 9/1986 | Fountail et al. |
| 4,803,070 A | 2/1989 | Cantrell et al. |
| 4,806,350 A | 2/1989 | Gerber |
| 4,806,352 A | 2/1989 | Cantrell |
| 4,920,016 A | 8/1990 | Allen et al. |
| 5,013,556 A | 5/1991 | Woodle et al. |
| 5,015,476 A | 5/1991 | Cochrum et al. |
| 5,084,269 A | 1/1992 | Kullenberg |
| 5,340,588 A | 8/1994 | Domb |
| 5,422,109 A | 6/1995 | Brancq et al. |
| 5,637,300 A | 6/1997 | Dunbar et al. |
| 5,662,931 A | 9/1997 | Munechika et al. |
| 5,688,772 A | 11/1997 | Estrada et al. |
| 5,705,151 A | 1/1998 | Dow et al. |
| 5,709,879 A | 1/1998 | Barchfeld et al. |
| 5,736,141 A | 4/1998 | Brown et al. |
| 5,820,879 A | 10/1998 | Fernandez et al. |
| 5,831,016 A | 11/1998 | Wang et al. |
| 5,844,075 A | 12/1998 | Kawakami et al. |
| 5,855,894 A | 1/1999 | Brown et al. |
| 5,863,549 A | 1/1999 | Tarantino |
| 5,897,873 A | 4/1999 | Popescu |
| 5,910,306 A | 6/1999 | Alving et al. |
| 5,919,480 A | 7/1999 | Kedar et al. |
| 5,980,898 A | 11/1999 | Glenn et al. |
| 5,990,287 A | 11/1999 | Hosokawa et al. |
| 6,037,135 A | 3/2000 | Kubo et al. |

(Continued)

FOREIGN PATENT DOCUMENTS

| | | |
|---|---|---|
| CA | 2078990 | 10/1991 |
| CA | 2082155 | 11/1991 |

(Continued)

OTHER PUBLICATIONS

European communication issued by the European Patent Office in European Application No. 12 838 879.0, dated Aug. 4, 2017.

(Continued)

*Primary Examiner* — Yunsoo Kim
(74) *Attorney, Agent, or Firm* — Troutman Pepper Hamilton Sanders LLP

(57) ABSTRACT

The invention provides compositions comprising liposomes, an antigen capable of inducing a humoral immune response, a carrier comprising a continuous phase of a hydrophobic substance, and an adjuvant that activates or increases the activity of TLR2. The invention also provides uses for such compositions in inducing a humoral response and methods for their use in the treatment of a disease, disorder or ailment ameliorated by a humoral immune response.

21 Claims, 7 Drawing Sheets

Specification includes a Sequence Listing.

(56) References Cited

U.S. PATENT DOCUMENTS

| | | | |
|---|---|---|---|
| 6,080,725 A | 6/2000 | Marciani |
| 6,090,406 A | 7/2000 | Popescu et al. |
| 6,093,406 A | 7/2000 | Alving et al. |
| 6,096,313 A | 8/2000 | Jäger et al. |
| 6,110,492 A | 8/2000 | Alving et al. |
| 6,124,270 A | 9/2000 | Haensler |
| 6,168,804 B1 | 1/2001 | Samuel et al. |
| 6,183,746 B1 | 2/2001 | Urban et al. |
| 6,214,367 B1 | 4/2001 | Harvey |
| 6,218,371 B1 | 4/2001 | Krieg et al. |
| 6,228,648 B1 | 5/2001 | Condon et al. |
| RE37,224 E | 6/2001 | Brown et al. |
| 6,267,985 B1 | 7/2001 | Chen et al. |
| 6,284,267 B1 | 9/2001 | Aneja |
| 6,291,430 B1 | 9/2001 | Chaux et al. |
| 6,306,405 B1 | 10/2001 | O'Hagan et al. |
| 6,309,569 B1 | 10/2001 | Farrar et al. |
| 6,372,227 B1 | 4/2002 | Garcon et al. |
| 6,406,719 B1 | 6/2002 | Farrar et al. |
| 6,461,325 B1 | 9/2002 | Van Nest et al. |
| 6,464,980 B1 | 10/2002 | Fikes et al. |
| 6,468,558 B2 | 10/2002 | Wong |
| 6,472,159 B1 | 10/2002 | Darbouret et al. |
| 6,472,375 B1 | 10/2002 | Hoon et al. |
| 6,497,896 B2 | 12/2002 | Sands et al. |
| 6,511,676 B1 | 1/2003 | Boulikas |
| 6,517,816 B1 | 2/2003 | Gonzalez et al. |
| 6,528,058 B1 | 3/2003 | Edgar et al. |
| 6,534,064 B1 | 3/2003 | O'Hagan et al. |
| 6,537,966 B1 | 3/2003 | Duan et al. |
| 6,544,518 B1 | 4/2003 | Friede et al. |
| 6,572,861 B1 | 6/2003 | Roberts et al. |
| 6,602,510 B1 | 8/2003 | Fikes et al. |
| 6,630,161 B1 | 10/2003 | Leesman |
| 6,632,447 B1 | 10/2003 | Steiner et al. |
| 6,649,172 B2 | 11/2003 | Johnson |
| 6,565,777 B2 | 12/2003 | Farrar et al. |
| 6,670,195 B1 | 12/2003 | Ghiso et al. |
| 6,676,958 B2 | 1/2004 | Gerber |
| 6,780,421 B1 | 8/2004 | Haensler et al. |
| 6,790,457 B1 | 9/2004 | Brown et al. |
| 6,793,923 B2 | 9/2004 | Brown et al. |
| 6,838,089 B1 | 1/2005 | Carlsson et al. |
| 6,881,405 B2 | 4/2005 | Leveugle et al. |
| 6,956,021 B1 | 10/2005 | Edwards et al. |
| 6,977,074 B2 | 12/2005 | Kündig et al. |
| 6,982,314 B2 | 1/2006 | Rosey |
| 7,019,112 B1 | 3/2006 | Slingluff et al. |
| 7,026,443 B1 | 4/2006 | Sette et al. |
| 7,037,509 B2 | 5/2006 | Koelle et al. |
| 7,056,515 B2 | 6/2006 | Brown et al. |
| 7,067,120 B2 | 6/2006 | Dianwen et al. |
| 7,087,236 B1 | 8/2006 | Brayden |
| 7,122,191 B2 | 10/2006 | Dominowski et al. |
| 7,306,787 B2 | 12/2007 | Tarara et al. |
| 7,604,802 B2 | 10/2009 | O'Hagan |
| 7,611,721 B1 | 11/2009 | Hagen |
| 7,687,455 B2 | 3/2010 | Bonnet et al. |
| 7,824,686 B2 | 11/2010 | Brown et al. |
| 7,943,147 B2 | 5/2011 | Carter et al. |
| 8,628,937 B2 | 1/2014 | Brown et al. |
| 10,105,435 B2 * | 10/2018 | Mansour ............... A61K 39/39 |
| 2002/0110568 A1 | 8/2002 | Brown et al. |
| 2003/0003105 A1 | 1/2003 | Gerber |
| 2003/0044454 A1 | 3/2003 | Fukui et al. |
| 2003/0181834 A1 | 8/2003 | Friede et al. |
| 2003/0185879 A1 | 10/2003 | Boulikas |
| 2003/0202979 A1 | 10/2003 | Gerber |
| 2003/0211115 A1 | 11/2003 | Gerber |
| 2003/0211140 A1 | 11/2003 | Mantripragada et al. |
| 2004/0170640 A1 | 9/2004 | Gerber |
| 2004/0202669 A1 | 10/2004 | O'Hagan |
| 2004/0213837 A1 | 10/2004 | Mantripragada et al. |
| 2004/0258701 A1 | 12/2004 | Dominowski et al. |
| 2005/0002952 A1 | 1/2005 | Haensler et al. |
| 2005/0002999 A1 | 1/2005 | Mehta et al. |
| 2005/0013812 A1 | 1/2005 | Dow et al. |
| 2005/0019339 A1 | 1/2005 | Brown et al. |
| 2005/0037061 A1 | 2/2005 | Hosokawa et al. |
| 2005/0079208 A1 | 4/2005 | Albani |
| 2005/0084524 A1 | 4/2005 | Martin et al. |
| 2005/0118154 A1 | 6/2005 | Hung et al. |
| 2005/0158375 A1 | 7/2005 | Kimura et al. |
| 2005/0175683 A1 | 8/2005 | Zhang et al. |
| 2005/0202078 A1 | 9/2005 | Schiffelers et al. |
| 2005/0214322 A1 | 9/2005 | Garcon et al. |
| 2005/0220781 A1 | 10/2005 | Yan et al. |
| 2005/0220814 A1 | 10/2005 | Dominowski et al. |
| 2005/0249795 A1 | 11/2005 | Zhang et al. |
| 2005/0260643 A1 | 11/2005 | Hung et al. |
| 2005/0266066 A1 | 12/2005 | Uchida et al. |
| 2006/0008909 A1 | 1/2006 | Cullis et al. |
| 2006/0182792 A1 | 8/2006 | Richardsen et al. |
| 2006/0183670 A1 | 8/2006 | Orban |
| 2006/0275777 A1 | 12/2006 | Waelti |
| 2006/0286038 A1 | 12/2006 | Rairkar et al. |
| 2007/0014805 A1 | 1/2007 | Dalencon et al. |
| 2007/0059318 A1 | 3/2007 | Balu-Iyer et al. |
| 2007/0082855 A1 | 4/2007 | Veldman et al. |
| 2007/0141078 A1 | 6/2007 | D'Hondt et al. |
| 2007/0212329 A1 | 9/2007 | Bruck et al. |
| 2007/0274980 A1 | 11/2007 | Balu-Iyer et al. |
| 2008/0014217 A1 | 1/2008 | Hanon et al. |
| 2008/0050395 A1 | 2/2008 | Gerber |
| 2008/0233143 A1 | 9/2008 | Jackson et al. |
| 2009/0017057 A1 | 1/2009 | Chen et al. |
| 2009/0035266 A1 | 2/2009 | Schlom et al. |
| 2009/0074853 A1 | 3/2009 | Brown et al. |
| 2009/0081244 A1 | 3/2009 | Glenn et al. |
| 2009/0032666 A1 | 4/2009 | Brown et al. |
| 2009/0124549 A1 | 5/2009 | Lewinsohn et al. |
| 2009/0155308 A1 | 6/2009 | Moon et al. |
| 2009/0169636 A1 | 7/2009 | O'Hagan et al. |
| 2009/0247456 A1 | 10/2009 | Srivastava et al. |
| 2009/0297593 A1 | 12/2009 | Daftarian et al. |
| 2010/0129385 A1 | 5/2010 | Jackson et al. |
| 2010/0203116 A1 | 8/2010 | Mansour et al. |
| 2010/0209452 A1 | 8/2010 | Mansour |
| 2011/0070298 A1 | 3/2011 | Mansour et al. |
| 2011/0200632 A1 | 8/2011 | Jackson et al. |

FOREIGN PATENT DOCUMENTS

| | | |
|---|---|---|
| CA | 2086094 | 12/1991 |
| CA | 2115424 | 3/1993 |
| CA | 2183435 | 8/1995 |
| CA | 2205083 | 5/1996 |
| CA | 2137363 | 6/1999 |
| CA | 2436348 | 6/2002 |
| CA | 2523032 | 4/2007 |
| CA | 2542212 A1 | 4/2007 |
| CA | 2622464 A1 | 4/2007 |
| CA | 2533705 | 7/2007 |
| EP | 0640347 A1 | 3/1995 |
| EP | 1333858 | 2/2006 |
| GB | 2134869 | 8/1984 |
| JP | 2004-512384 | 4/2004 |
| JP | 2010-540570 | 12/2010 |
| JP | 2011-506309 | 3/2011 |
| JP | 2011-523653 | 8/2011 |
| WO | WO 92/00081 | 1/1992 |
| WO | WO 92/10513 | 6/1992 |
| WO | WO 93/25231 | 12/1993 |
| WO | WO 1995/31480 | 11/1995 |
| WO | WO 1996/014871 | 5/1996 |
| WO | WO 98/053799 | 12/1998 |
| WO | WO 2000/37100 | 6/2000 |
| WO | 2002/038175 | 5/2002 |
| WO | WO 2002/38175 | 5/2002 |
| WO | WO 2002/070006 A2 | 9/2002 |
| WO | WO 2004/000873 A2 | 12/2003 |
| WO | WO 2004/052917 | 6/2004 |
| WO | WO 2004/058179 | 7/2004 |
| WO | WO 2004/094454 | 11/2004 |

(56) References Cited

FOREIGN PATENT DOCUMENTS

| WO | WO 2005/019435 | 3/2005 |
|---|---|---|
| WO | WO 2005/025614 A2 | 3/2005 |
| WO | WO 2005/072777 A2 | 8/2005 |
| WO | WO 2005/089164 | 9/2005 |
| WO | WO 2006 050155 | 5/2006 |
| WO | WO 2006/113679 A2 | 10/2006 |
| WO | WO 2007/041832 A1 | 4/2007 |
| WO | WO 2007/071707 | 6/2007 |
| WO | WO 2007/071710 | 6/2007 |
| WO | WO 2007/071711 | 6/2007 |
| WO | 2009/043165 | 4/2009 |
| WO | 2009/072767 | 6/2009 |
| WO | 2009/146523 | 12/2009 |
| WO | WO 2009/146523 A1 | 12/2009 |
| WO | WO 2003/066680 | 8/2013 |

OTHER PUBLICATIONS

Barrenschee, et al., "Effects of the TLR2 Agonists MALP-2 and Pam3Cys in Isolated Mouse Lungs," PLoS ONE, 2010, vol. 5, No. 11, 12 pages total.
Israeli Office Action regarding Israeli Patent Application 231888, dated Jan. 17, 2017 (3 pgs.).
English translation of Israeli Office Action regarding Israeli Patent Application 231888, dated Jan. 17, 2017 (5 pgs.).
Rose et al.:"FSL-1, a bacterial derived toll like receptor2/6 agonist, enhances resistance to experimental HSV-2 infection" Virology Jour. vol. 6, No. 1, (Jan. 1, 2009), p. 195. (11 pgs.).
Steinhagen et al., "TLR-Based Immune Adjuvants", Vaccine 29 (2011), pp. 3341-3355.
Bessler et al., "Bacterial Cell Wall Components as Immunomodulators-I. Lipopeptides as Adjuvants for Parental and Oral Immunization", Intl. J. Immunopharmac. (1997) vol. 19, No. 9/10, pp. 547-550.
First Office Action regarding related Japanese patent application JP 2014-533747, dated Jul. 12, 2016 (3pgs.).
English translation of First Office Action regarding related Japanese patent application JP 2014-533747, dated Jul. 12, 2016 (3pgs.).
Basto et al., "Targeting TLR2 for Vaccine Development", J. Immunol Research, vol. 2014, Article ID 619410 (23 pgs.).
Muller et al., "Specific Anitbody Response Towards Predicted Epitopes of the Epidermal Growth Factor Receptor Induced by a Thermostable Synthetic Peptide Adjuvant Conjugate", Immunol. (1989) 78, 499-504 (6 pgs.).
Reichel et al., "Stereochemical Dependence of the Self-Assembly of the Immunoadjuvants Pam3CYS and Pam3Cys-Ser", J. Am. Chem. Soc. 1999, 121, 7989-7997 (9 pgs.).
Voss et al., "The Activity of Lipopeptide TLR2 Agonists Critically Depends on the Presence of Solubilizers", Eur. J. Immunol. 2007, 37:3489-3498 (10 pgs.).
Zeng et al., "Highly Immunogenic and Totally Synthetic Lipopeptides as Self-Adjuvanting Immunocontraceptive Vaccines", J. Immunol 2002; 169:4905-4912 (9 pgs.).
Singapore Written Opinion Appln No. 11201401177W.
Biochemicals Catalogue 2012; New: Antifungal Compounds, EMC Microcollections, (2012), pp. 1-46, see pp. 1-11.
Zeng et al., "Structural Requirement for the Agonist Activity of the TLR2 Ligand PAM2CYS", Amino Acids (2010) 39:471-480.
Moyle et al., "Self-Adjuvanting Lipopeptide Vaccines", Current Medical Chemistry (2008) 15, 506-516.
Karkada et al., "A Liposome-Based Platform, Vaccimax. and Its Modified Water-Free Platform Depovax Enhance Efficacy of In Vivo Nucleic Acid Delivery", Vaccine 28 (2010) 6176-6182.
Daftarian et al., "Eradication of Established HPV 16-Expressing Tumors by a Single Administration of a Vaccine Composed of a Liposome-Encapsulated CTL-T Helper Fusion Peptide in a Water-in-Oil Emulsion", Vaccine 24 (2006), 5235-5244.
Mansour et al., "Improved Efficacy of a Licensed Acellular Pertussis Vaccine, Reformulated in an Adjuvant Emulsion of Liposomes in Oil, in a Murine Model", Clinical and Vaccine Immunology vol. 14, No. 10,(Oct. 2007) 1381-1383.

Steinhagen et al., "TLR-Based Immune Adjuvants", Vaccine 29 (2011) 3341-3355.
Bal et al., "Co-encapsulation of Antigen and Toll-Like Receptor Ligand in Cationic Liposomes Affects the Quality of the Immune Response in Mice After Intradermal Vaccination", Vaccine 29 (2011) 1045-1052.
Partial Supplementary European Search Report for EP12838879.0, dated Feb. 11, 2015 (9 pgs.).
Sparwasser, T. et al., "Bacterial DNA and immunostimulatory CpG oligonucleotides trigger maturation and activation of murine dendritic cells", Eur. J. Immunol., (1998) p. 2045-2054, vol. 28.
Stephen, E.L. et al., "Effect a nuclease-resistant derivative of polyrinoinosinio-polyribocytidylic acid complex on yellow fever in rhesus monkeys (*Macaca mulatta*)", J Infect Dis, (1977) p. 122-128, vol. 136.
Stephen, E.L. at al., "Swine influenza virus vaccine: potentiation of antibody responses in rhesus monkeys", Science, (1977) p. 1289-1290, vol. 197.
Stern, P.L., "Immune control of human papillomavirus (HPV) associated anogenital disease and potential for vaccination", J. Clin. Viral., (2005) 32 Suppl. 1:S72-81.
Stone, "Newcastle Disearse Oil Emulsion Vaccines Prepared with Animal, Vegetable, and Synthetic Oils", Avian Diseases 41:591-597, 1997.
Tai et al., "A Universal T Cell Vaccine Against Influenza A", The FASEB Journal, (Apr. 2008), vol. 22 Abstract No. 853.11.
Takeuchi, O. et al., "Cutting edge: role of toll-like receptor 1 in mediating immune response to microbial lipoproteins", The Journal of Immunology (2002) p. 10-14, ISSN 0022-1767, vol. 169.
Takeuchi, O. et al., "Pattern recognition receptors and inflammation" Cell (2010), vol. 140, No. 6, p. 805-820.
Talmadge, J.E. et al., "Immunotherapeutic potential in murine tumor models of polyinosinic-polycytidylic acid and poly-L-lysine solubilized by carboxymethylcellulose", Cancer Res., (1985) p. 1066-1072, vol. 45.
Teuten, A.J. et al., "Characterization of structural and folding properties of streptokinase by n.m.r. spectroscopy", Biochem. J., (1993) p. 313-319, vol. 290.
The National Wildlife Research Center, "Porcine Zona Pellucida Immunocontraception in Mammals," (Oct. 9, 2007), accessed online: www.a-phis.usda.gov/ws/nwrc/pzp.htm>.
Thueng-In, K. et al., "Heterosubtypic immunity to influenza mediated by liposome adjuvanted H5N1 recombinant protein vaccines", Vaccine (2010), vol. 28, p. 6765-6777.
Tillman, B.W. et al., "Adenoviral vectors targeted to CD40 enhance the efficacy of dendrite cell-based vaccination against human papillomavirus 16-induced tumor cells in a murine model", Cancer Res., (2000) p. 5456-5463, vol. 60.
Tiwari, S. et al., "Gel core liposomes: an advanced carrier for improved vaccine delivery", J. Microencapsul., (Feb. 2009), p. 75-82, vol. 26, No. 1 (Abstract only).
Torrèns, I. et al., "A mutant streptokinase lacking the C-terminal 42 amino acids is less immunogenic", Immunology Letters, (1999) p. 213-218, vol. 70.
Torrèns, I. et al., "Immunotherapy with CTL peptide and VSSP eradicated established human papillomavirus (HPV) type 16 E7-expressing tumors", Vaccine, (2005) p. 5768-5774, vol. 23.
Trumpfheller, C. et al., "The microbial mimic poly IC induces durable and protective CD4+ T cell immunity together with a dendritic cell targeted vaccine", Proc Natl Aced Sci USA, (2008) p. 2574-2579, vol. 105.
Tsukui, T. et al., "Interleukin 2 production in vitro by peripheral lymphocytes in response to human Papillomavirus-derived peptides: correlation with cervical pathology", Cancer Res., (1996) p. 3967-3974, vol. 56.
Van Oosterhout, A.J.M. et al., "Th1/Th2 paradigm: not seeing the forest for the trees?", Eur. Respir. J., (2005) p. 591-593, vol. 26.
Velders, M.P. et al., "Eradication of established tumors by vaccination with Venezuelan equine encephalitis virus replicon particles delivering human papillomavirus 16 E7 RNA", Cancer Res., (2001) p. 7861-7867, vol. 61.

(56) References Cited

OTHER PUBLICATIONS

Walboomers, J.M. et al., "Human papillomavirus is a necessary cause of invasive cervical cancer worldwide", J. Pathol., (1999) p. 12-19, vol. 189.
Wang, J.-C. et al., "Cutting edge: CD4+ T cell help can be essential for primary CD8+ T cell responses in vivo", J. Immunol., (2003) p. 6339-6343, vol. 171.
Weeratna, R.D. et al., "CpG DNA induces stronger immune responses with less toxicity than other adjuvants", Vaccine (2000) p. 1755-1762, vol. 18.
Welters et al., "Multiple CD4 and CD8 T-cell activation parameters predict vaccine efficacy in vivo mediated by individual DC-activating agonists", Vaccine (2007), vol. 25, No. 8, p. 1379-1389.
Wiedemann, F. et al., Histopathological studies on the local reactions induced by complete Freund's adjuvant (CFA), bacterial lipopolysaccharide (LPS), and synthetic lipopeptide (P3C) conjugates, J Pathol (1991), vol. 164, No. 3, p. 265-271.
Wiesmuller, K.H. et al.., "Peptide vaccines and peptide libraries", Biol. Chem., (Apr. 2001), p. 571-579, vol. 382.
Wilcox, R.A. et al., "Provision of antigen and CD137 signaling breaks immunological ignorance, promoting regression of poorly immunogenic tumors", J. Clin. Invest., (2002) p. 651-659, vol. 109.
Willard et al., Pregnancy detection and the effects of age, body weight, and previous reproductive performance on pregnancy status and weaning rates of farmed fallow deer (*Dama dama*), J. Animal Science, (1999) p. 32-38, vol. 77.
Witt et al., "Phase I trial of en oral immunomodulator and interferon inducer in cancer patients", Cancer Research (1993), vol. 53, p. 5176-5180.
Yoneyama, M. et el., "The RNA helicase RIG-I has an essential function in double-stranded RNA-induced innate antiviral responses", Nat Immunol, (2004) p. 730-737. vol. 5.
Zaks, K. et al., "Efficient immunization and cross-priming by vaccine adjuvants containing TLR3 or TLR9 agonists complexed to cationic liposomes", J. Immunol., (2006) p. 7335-7345, vol. 176.
Zauner, W. et al., "Defined synthetic vaccines", Biol. Chem., (2001) p. 581-595, vol. 382.
Zhang et al., "A Novel DNA Vaccine Based on Ubiquitin-Proteasome Pathway Targeting 'Self'-Antigens Expressed in Melanoma/Melanocyte", Gene Therapy (2005), vol. 12, p. 1049-1057.
Zhu, X. et al. "Toll like receptor-3 ligand poly-ICLC promotes the efficacy of peripheral vaccinations with tumor antigen-derived peptide epitopes in murine CNS tumor models", J Transl. Med., (2007) vol. 5:10.
Zinkernagel, R.M., "On cross-priming of MHC class I-specific CTL: rule or exception?", Eur. J. Immunol., (2002) p. 2385-2392, vol. 32.
Zur Hausen, H., "Papillomaviruses and cancer: from basic studies to clinical application", Nat. Rev. Cancer, (2002) p. 342-350, vol. 2.
Pam2CSK4, Product Information Sheet, InvivoGen, San Diego, CA 92121—USA.
Pam3CSK4, Product Information Sheet, InvivoGen, San Diego, CA 92121—USA.
International Search Report dated Jan. 10, 2013, International Application No. PCT/CA2012/050705.
Liang, M.T. et al., "Particulate systems as adjuvants and carriers for peptideand protein antigens", Current Drug Delivery, (2006), p. 379-388, vol. 3.
Llopiz, D. et al., "Combined immunization with adjuvant molecules poly(I:C) and anti-CD40 plus a tumor antigen has potent prophylactic and therapeutic antitumor effects", Cancer Immunol Immunother, (2008) p. 19-29, vol. 57.
Maes et al., "Potentiation of FMD vaccines with plycationic-nucleic acid complexes", Arch Virol., (1977), vol. 55, No. 4, p. 275-85.
Mansour, M. et al. "Therapy of Established B16-F10 Melanoma Tumours by a Single Vaccination of CTL/T Helper Peptides in VacciMax®", J. Transl. Med., (Apr. 2007), p. 1-8, vol. 5, No. 20.
Mansour, M. et al. "Improved efficacy of a licensed acellular pertussis vaccine, reformulated in an adjuvant emulsionl of liposomes in oil, in a murine model", Clin. and Vaccine Immunol., (Oct. 2007), p. 1381-1363, vol. 14, No. 10.
Matsumoto, M. el al, TLR3: interferon induction by double-stranded RNA including poly(I:C), Adv Drug Deliv Rev (2008), vol. 60, No. 7, p. 805-812.
Matthews, L.J. et al., "Immunogenically fit subunit vaccine components via epitope discovery from natural peptide libraries", J. Immunol, (2002) p. 837-846, vol. 169.
Mayordomo, J.I. et al., "Bone marrow-derived dendritic cells pulsed with synthetic tumour peptides elicit protective and therapeutic antitumour immunity", Nat. Med., (1995) p. 1297-1302, vol. 1.
Meyer et al., "Recent developments in the application of plasmid DNA-based vectors and small interfering RNA therapeutics for cancer", Human Gene Therapy (Nov. 2006), vol. 17, No. 11, p. 1062-1076.
Millan, C.L.B. et al., "CpG DNA can induce strong Th1 humoral and cell-mediated immune responses against hepatitis B surface antigen in young mice", PNAS, (1998) p. 15553-15558, vol. 95.
Mosmann, T.R., "Role of a New Cytokine, Interleukin-10, in the Cross-Regulation of T Helper Cells", Acad. Sci. (1991) p. 337-344, vol. 628.
Moyle et al., "Self-adjuvanting lipopeptide vaccines", Curr. Med. Chem. (2008), vol. 15, No. 5, p. 506-516.
Muderhwa, J.M. et al., "Oil-in-water liposomal emulsions: characterization and potential use in vaccine delivery", J. Pharm. Sci. (Dec. 1999) p. 1332-1339, ISSN 0022-3549, vol. 88, No. 12.
Muttilainen, S. et al., "The Neisseria meningitidis outer membrane protein P1 produced in Bacillus subtilis and reconstituted into phospholipid vesicles elicits antibodies to native P1 epitopes", Microbial Pathogenesis, (1995) p. 423-436, vol. 18.
Nakamura, O. et al., "Phase I-II trials of poly(ICLC) in malignant brain tumor patients", J Interferon Res, (1982) p. 1-4, vol. 2.
Nash et al., "Formulation of a potential antipregnancy vaccine based on the b-subunit of human chorionic gonadotropin (b-hCG). II. Use of compounds of the muramyl dipeptide (MDP) family as adjuvants", J. Reprod. Immunol., (1985) p. 151-162, vol. 7, No. 2.
Needleman, S.B. and Wunsch, C.D. "A General Method Applicable to the Search for Similarities in the Amino Acid Sequence of Two Proteins", J. Mol. Biol., (1970) p. 443-453, vol. 48.
Öhlschläger, P. et al., "Human Papillomavirus Type 16 L1 Capsomeres Induce Li-Specific Cytotoxic T Lymphocytes and Tumor Regression in C57BL/6 Mice", Journal of Virology (2003) p. 4635-4645, vol. 77.
Ouyang, X. et al., "Cooperation between MyD88 and TRIF pathways in TLR synergy via IRF5 activation", Biochem Biophys Res Commun (2007), vol. 354, No. 4, p. 1045-1051.
Padalko, E. et al., "The interferon inducer ampligen [poly(I)-poly(C12U)] markedly protects mice against coxsackie B3 virus-induced myocarditis", Antimicrob Agents Chemother, (2004) p. 264-274, vol. 48.
Padilla-Paz, L.A., "Human papillomavirus vaccine: history, immunology, current status, and future prospects", Clin. Obstet. Gynecol., (2005) p. 226-240, vol. 48.
Parkin, D.M. et al., "Estimating the world cancer burden: Globocan 2000", Int. J. Cancer, (2001) p. 153-156, vol. 94.
Parrado et al., "The domain organization of streptokinase: Nuclear magnetic resonance, circular dichroism, and functional characterization of proteolytic fragments", Protein Sci., (1996) p. 693-704, vol. 5.
Pearson and Lipman, "Improved Tools for biological sequence comparison", Proc Natl Acad Sci USA (1988), vol. 85. No. 8, p. 2444-2448.
Pilon-Thomas, S. et al., "Immunostimulatory Effects of CpG-ODN Upon Dendritic Cell-Based Immunotherapy in a Murine Melanoma Model", Journal Immunotherapy, (2006) p. 381-387, vol. 29, No. 4.
Poast, J. et al., "Poly I:CLC induction of the interferon system in mice: an initial study of four detection methods", J Interferon Cytokine Res, (2002) p. 1035-1040, vol. 22.
Puri, S.K. et al., "Poly ICLC inhibits Plasmodium cynomolgi B malaria infection in rhesus monkeys", J Interferon Cytokine Res., (1996) p. 49-52, vol. 16.

(56) References Cited

OTHER PUBLICATIONS

Pye, D. et al., "Selection of an adjuvant for vaccination with the malariai antigen, MSA-2", Vaccine, (1997) p. 1017-1023, vol. 15, No. 9.
Rao, M. et al., "Delivery of lipids and liposomal proteins to the cytoplasm and Golgi of antigen-presenting cells", Adv. Drug Deliv. Rev., (2000) p. 171-188, vol. 41.
Rao, M. et al., "Intracellular processing of liposome-encapsulated antigens by macrophages depends upon the antigen", Infect. Immun., (1995) p. 2396-2402, vol. 63.
Re, F. et al., IL-10 released by concomitant TLR2 stimulation blocks the induction of a subset of Th1 cytokines that are specifically induced by TLR4 or TLR3 in human dendritic cells, J Immunol (2004), vol. 173. No. 12, p. 7548-7555.
Rechtsteiner et al., "Cutting Edge: Priming of CTL by transcutaneous peptide immunization with imiquimod", Journal of Immunology (2005), vol. 174, p. 2476-2480.
Reis E Sousa,C., "Toll-tike receptors and dendritic cells: for whom the bug tolls", Semin. Immunol., (2004) p. 27-34, vol. 16.
Richards et al., "Liposome-stabilized oil-in-water emulsions as adjuvants: Increased emulsion stability promotes induction of cytotoxic T lymphocytes against an HIV envelope antigen", Immunology and Cell Biology (2004), vol. 82, p. 531-538.
Riedl, K. et al., "The novel adjuvant IC31® strongly improves influenza vaccine-specific cellular and humoral immune responses in young adult and aged mice", Vaccine, (2008) p. 3461-3468, vol. 26.
Roberge, J.Y. et al., "A Strategy for a Convergent Synthesis of N-Linked Glycopeptides on a Solid Support", Science, (1995) p. 202-204, vol. 269.
Salazar, A.M. et al., "Long-term treatment of malignant gliomas with intramuscularly administered poluyinosinic-polycytidylic acid stabilized with polylysine and carboxymethylcellulose: an open pilot study", Neurosurgery, (1996) p. 1096-103 and discussion 1103-1104, vol. 38.
Salem, M.L. et al., "The adjuvant effects of the toll-like receptor 3 ligand polyinosinic-cytidylic acid poly (I:C) on antigen-specific CD8+ T cell responses are partially dependent on NK cells with the induction of a beneficial cytokine milieu", Vaccine, (2006) p. 5119-5132, vol. 24.
Salem, M.L. et al., "Defining the antigen-specific T-cell response to vaccination and poly(I:C)/TLR3 signaling: evidence of enhanced primary and memory CD8 T-cell responses and antitumor Immunity", Immunother, (2005) p. 220-228, vol. 28.
Sarma, P.S. et al., "Virus-induced sarcoma of mice: inhibition by a synthetic polyribonucleotide complex", Proc Natl Acad Sci USA, (1969) p. 1046-1051, vol. 62.
Schellack, C. et al., "IC31, a novel adjuvant signaling via TLR9, induces potent cellular and humoral immune responses", Vaccine, (2006) p. 5461-5472, vol. 24.
Schijns, V.E., "Immunological con pts of vaccine adjuvant activity", Current Opinion in Immunology, (2000) p. 456-463, vol. 12.
Schreckenberger, C. et al., "Vaccination strategies for the treatment and prevention of cervical cancer", Curr. Opin. Oncol., (2004) p. 485-491, vol. 16.
Schueler-Furman, O. et al., "Knowledge-based structure prediction of MHC class I bound peptides: a study of 23 complexes", Folding & Design, (1998) p. 549-564, vol. 3.
Seya T. et al., "Roll of Toll-like receptors in adjuvant-augmented immune therapies", Evid Based Complement Alternat Med (2006), vol. 3, No. 1, p. 31-38.
Shedlock, D.J. et al., "Requirement for CD4 T cell help in generating functional CD8 T cell memory", Science, (2003) p. 337-339, vol. 300.
Sloat, B.R. et al., "Nasal immunization with the mixture of PA63, LF, and a PGA conjugate induced strong antibody responses against all three antigens", FEMS Immunol Med Microbial, (2008) p. 169-179, vol. 5.
Smith, K.M., et al., "In Viva Generated Th1 Cells Can Migrate to B Cell Follicles to Support B Cell Responses", J. Immunol., (2004) p. 1640-1646, vol. 173.
Smith, T.F. and Waterman, M.S. "Comparison of Biosequences", Adv. Appl. Math, (1981) p. 482-489, vol. 2.
So, Nancy S.Y. et al., "Vigorous Response of Human Innate Functioning IgM Memory B cells upon Infection by Neisseria gonorrhoeae", J. Immund., (2012), Vo. 188, published online.
Fagerstone, K. A. et al., "Wildlife Fertility Control", The Wildlife Society Technical Review 02-2, (2002) p. 1-29, University of Nebraska—Lincoln.
Fausch, S.C. et al., "Human Papillomavirus Can Escape Immune Recognition through Lanrgerhans Cell Phosphoinositide 3-Kinase Activation", J. Immunol., (2005) p. 7172-7178, vol. 174.
Feltkamp, M.C. et al., "Vaccination with cytotoxic T lymphocyte epitope-containing peptide protects against a tumor induced by human papillomavirus type 16-transformed cells", Eur. J. Immunol., (1993) p. 2242-2249, vol. 23.
Fernando, G.J. et al., "Vaccine-induced Th1-type responses are dominant over Th2-type responses in the short term whereas pre-existing Th2 responses are dominant in the longer term", Scandinavian Journal of Immunology, (1998) p. 459-465, vol. 47 No. 5.
Fraker, M.A. et al., "Long-Lasting, Single-Dose Immunocontraception of Feral Fallow Deer in British Columbia", J. Wildl. Manage., (2002) p. 1141-1147 vol. 66.
Frazer, I.H., "Prevention of cervical cancer through papillomavirus vaccination", Nat. Rev. Immunol., (2004) p. 46-54, vol. 4.
Frey, A. et al., "A statistically defined endpoint titer determination method for immunoassays", J Immunol Methods, (1998) p. 35-41, vol. 221.
Frezard, F., "Liposomes: from biophysics to the design of peptide vaccines", Brazilian Journal of Medical Biology and Research, (1999) p. 181-189, vol. 32.
Fujimura, T. et al., "Inhibitory effect of the polyinosinic-polycytidylic acid/cationic liposome on progression of murine B16F10 melanoma", Eur J Immunol, (2006) p. 3371-3380, vol. 36.
Gerard, C.M. et al., "Therapeutic potential of protein and adjuvant vaccinations on tumour growth", Vaccine, (2001) p. 2583-2589, vol. 19.
Ghosh, T.K. et al., "Toll-like receptor (TLR2) 2-9 agonists-induced cytokines and chemokines: I. Comparison with T cell receptor-induced responses", Cell Immunol (2006), vol. 243. No. 1, p. 48-57.
Gillison, M.L., "Human papillomavirus-associated head and neck cancer is a distinct epidemiologic, clinical, and molecular entity", Semin. Oncol., (2004) p. 744-754, vol. 31.
Goedert, M. et al., "A Century of Alzheimer's Disease", Science, (2006) p. 777-81, vol. 314.
Gorman, S.P. et al., "Evaluation of a porcine zona pellucida vaccine for the immunocontraception of domestic kittens (*Felis catus*)", Theriogenology, (2002) p. 135-149, vol. 58.
Gowen, B.B., et al., "TLR3 is essential for the induction of protective immunity against Punta Toro Virus infection by the double-stranded RNA (dsRNA), poly(I:C12U), but not Poly(I:C): differential recognition of synthetic dsRNA molecules", J Immunol, (2007) p. 5200-5208, vol. 178.
Greene, J.J. et al. "Interferon induction and its dependence on the primary and secondary structure of poly(inosinic acid). poly(cytidylic acid)", Biochemistry, (1978) p. 4214-4220, vol. 17.
Gregoriadis, G., "Immunological adjuvants: A role for liposomes", Immunology Today, (1990) p. 89-97, vol. 11, No. 3.
Gulley, J.L. et al., "Combining a recombinant cancer vaccine with standard definitive radiotherapy in patients with localized prostate cancer", Clinical Cancer Research, (2005) p. 3353-3362 vol. 11.
Gupta et al., "Adjuvants—a balance between toxicity and adjuvanticity", Vaccine, (1993) p. 293-306, vol. 11, No. 13.
Gupta, R. et al., "Adjuvants for human vaccines-current status, problems and future prospects", Vaccine, (1995) p. 1263-1276, vol. 13, No. 14.
Guschlbauer, W. et al., "Poly-2'-deoxy-2'-fluoro-cytidylic acid: enzymatic synthesis, spectroscopic characterization and interaction with poly-inosinic acid", Nucleic Acids Res, (1977) p. 1933-43, vol. 4.
Guy, B. "The perfect mix: recent rogress in adjuvant research", Nat Rev Microbiol., (2007) p. 505-517, vol. 5.

(56) References Cited

OTHER PUBLICATIONS

Harada, M. et al., "Vaccination of cytotoxic T lymphocyte-directed peptides elicited and spread humoral and Th1-type immune responses to prostate-specific antigen protein in a prostate cancer patient", J. Immunother. (Jul.-Aug. 2005) p. 368-375, ISSN 1524-9557, vol. 28, No. 4.
Harrenstien, L.A. et al., "Effects of Porcine Zona Pellucida Immunocontraceptives in Zoo Felids", J. Zoo Wildlife Medicine, (2004) p. 271-279, vol. 35.
Hendrix, C.W. et al. "Biologic effects after a single dose of poly(I):poly(C12U) in healthy volunteers", Antimicrob. Agents Chemother., (1993) p. 429-435, vol. 37.
Heurtault. B. et al., "Liposome-based Systems for Anti-tumor Vaccination: Influence of Lipopeptide Adjuvants", Journal of Liposome Research (2006), vol. 16, p. 205-213.
Hilbert, A. et al., "Biodegradable microspheres containing influenza A vaccine: immune response in mice", Vaccine, (1999) p. 1065-1073, vol. 17, No. 9-10.
Houston, W.E. et al., "Modified polyriboinosinic-polyribocytidylic acid, an immunological adjuvant", Infect Immun, (1976) p. 318-319, vol. 14.
Husband, A.J., "Novel vaccination strategies for the control of mucosal infection", Vaccine, (1993) p. 107-112, vol. 11, No. 2 (abstract only).
Ichinohe, T. et al., "Cross-protection against H5N1 influenza virus infection is afforded by intranasal inoculation with seasonal trivalent inactivated influenza vaccine", J Infect Dis., (2007) p. 1313-1320, vol. 196.
Itoh, T. et al., "Transcutaneous immunization with cytotoxic T-cell peptide epitopes provides effective antitumor immunity in mice", J. Immunother., (2005) p. 430-437, vol. 28.
Itzhaki, R.F. et al., "Simplex Virus Type 1 in Alzheimer's Disease: The Enemy Within", J Alzheimer Dis., (2008) p. 393-405, vol. 13.
Ivanova et al., "Contraceptive potential of porcine zone pellucida in cats", Theriogenology, (1995) p. 969-981, vol. 43.
Jentoft, N. et al., "Labeling of proteins by reductive methylation using sodium cyanoborohydride", J. Biol. Chem., (1979) p. 4369-4365, vol. 254, No. 11.
Jerome, V. et al, "Cytotoxic T lymphocytes responding to low dose TRP2 antigen are induced against B16 melanoma by liposome-encapsulated TRP2 peptide and CpG DNA adjuvant", J. Immunother., (2006) p. 294-305, vol. 29, No. 3.
Jin, B. et al, "Induction of potent cellular immune response in mice by hepatitis C virus NS3 protein with double-stranded RNA", Immunology, (2007) p. 15-27, vol. 122.
Johnston, M.I. et al., "Structural features of double-stranded polyribonucleotides required for immunological specificity and interferon induction", Proc Nati Aced Sci USA, (1975) p. 4564-4568, vol. 72.
Kadowaki, N. et al., "Subsets of human dendritic cell precursors express different toll-like receptors and respond to different microbial antigens", J. Exp. Med., (2001) p. 863-869, vol. 194.
Kamath, A.T. et al., "Protective anti-mycobacterial T cell responses through exquisite in vivo activation of vaccine-targeted dendritic cells", Eur J Immunol., (2008) p. 1247-1256, vol. 38.
Karkada et al., "A liposome-based platform, VaccciMax, and its modified water-free platform DepoVax enhance efficacy in vivo nucleic acid delivery", Vaccine (Aug. 31, 2010), Elsevier Ltd, GB, vol. 28, No. 38, p. 6176-6182.
Kawaoka, Y. et al., "Molecular Characterization of a New Hemagglutinin, Subtype H14, of Influenza A Virus", Virology, (1990) p. 759-767, vol. 179.
Kende, M. et al., "Ranking of prophylactic efficacy of poly(ICLC) against Rift Valley fever virus infection in mice by incremental relative risk of death", Antimicrob Agents Chemother., (1987) p. 1194-1198, vol. 31.
Knutson, K.L., et al., "Immunization of cancer patients with a HER-2/neu, HLA-A2 peptide, p369-377, results in short-lived peptide-specific immunity", Clinical Cancer Research, (2002) p. 1014-1018, vol. 8, No. 5.

Koutsky, L.A., et al., "A controlled trial of a human papilloavirus type 16 vaccine", N. Engl. J. Med., (2002) p. 1645-1651, vol. 347.
Krown, S.E. et al., "Phase I trials of poly(I,C) complexes in advanced cancer", J Biol Response Mod, (1985) p. 640-649. vol. 4.
Lahiri et al., "Engagement of TLR signaling as adjuvant; towards smarter vaccine and beyond", Vaccine (2008),vol. 26, No. 52, p. 6777-6783.
Lambros, M.P. et al. "Liposomes, a potential immunoadjuvant and carrier for a cryptococcal vaccine", J. Pharmaceutical Sciences, (Sep. 1998), p. 1144-1148, vol. 87, No. 9.
Levy, H.B. "Historical overview of the use of polynucleotides in cancer", J Biol Response Mod., (1985) p. 475-480, vol. 4.
Levy, H.B. et al., "Topical treatment of vaccinia virus infection with an interferon inducer in rabbits", J Infect Dis., (1978) p. 78-81, vol. 137.
Levy, J.K. et al., "Survey of zona pellucida antigens for immunocontraception of cats", Theriogenology, (2005) p. 1334-1341, vol. 63.
Adam, J.K. et al., "Immune responses in cancer", Pharmacol. Ther., (2003) p. 113-132, vol. 99.
Agger, E.M. et al, "Protective immunity to tuberculosis with Ag85B-ESAT-6 in a synthetic cationic adjuvant system IC31", Vaccine, (2006) p. 5452-5460, vol. 24.
Alexander, J. et al., "Development of high potency universal DR-restricted helper epitopes by modification of high affinity DR-blocking peptides", Immunity (1994) p. 751-761, vol. 1.
Alexopoulou, L. et al., "Recognition of double-stranded RNA and activation of NF-kappaB by Toll-like receptor 3", Nature, (2001) p. 732-738, vol. 413.
Allegra, C.J. et al., "Cytotoxins and cancer immunotherapy. The dance of the macabre?", J. National Cancer Institute, (2005) p. 1396-1397, vol. 97.
Altschul, S.F. et al., "Basic Local Alignment Search Tool", J. Mol. Biol., (1990) p. 403-410, vol. 215.
Alving, C.R., "Design and selection of vaccine adjuvants: animal models and human trials", Vaccine, (2002) p. S56-S64, vol. 20.
Antonia, S.J. et al., "Combination of p53 cancer vaccine with chemotherapy in patients with extensive stage small cell lung cancer" Clinical Cancer Research, (2006) p. 878-887, vol. 12.
Avril T. et al., Not all polyriboinosinic-polyribocytidylic acids (Poly I:C) are equivalent for inducing maturation of dendritic cells: implication for alpha-type-1 polarized DCs, J Immunother (2009), vol. 32, No. 4, p. 353-362.
Awasthi, A. et al., "Poly ICLC enhances the antimalarial activity of chloroquine against multidrug-resistant Plasmodium yoelii nigeriensis in mice", J Interferon Cytokine Res., (1997) p. 419-423, vol. 17.
Bagavant et al., "Antifertility effects of porcine zone pellucida-3 immunization using permissible adjuvants in female bonnet monkeys (*Macaca radiata*): reversibility, effect on follicular development and hormonal profiles", J. Reprod. Fertil., (1994) p. 17-25, vol. 102.
Banga, A.K. Therapeutic Peptides and Proteins, Formulations, Processing and Delivery Systems, (1995), Technomic Publishing Co., Lancaster, PA.
Barchet, W. et al., "Accessing the therapeutic potential of immunostimulatory nucleic acids", Curr Opin Immunol (2008), vol. 20, No. 4, p. 389-395.
Bellone, M. et al., "Relevance of the tumor antigen in the validation of three vaccination strategies for melanoma", Journal of Immunology, (2000) p. 2651-2656, vol. 165, No. 5.
Bever, C.T. et al., "Preliminary trial of poly ICLC in chronic progressive multiple sclerosis", Neurology, (1986). p. 494-498, vol. 36.
Blander J.M. et al., "Phagocytosis and antigen presentation: a partnership initiated by Toll-like receptors", Ann Rheum Dis (2008), vol. 67, Suppl. 3, p. iii44-9.
Bobst, A.M. et al., "Interferon induction by poly(inosinic acid). poly(cytidylic acid) segmented by spin-labels", Biochemistry, (1981) p. 4798-4803, vol. 20.
Bosch, F.X. et al., "Prevalence of human papillomavirus in cervical cancer: a worldwide perspective", J. Natl. Cancer Inst., (1995) p. 796-802, vol. 87.

(56) References Cited

OTHER PUBLICATIONS

Bronte, V. et al., "Genetic Vaccination with "Self" Tyrosinase-related Protein 2 Causes Melanoma Eradication but not Vitiligo", Cancer Research, (Jan. 15, 2000) p. 253-258, vol. 60.
Brown, R.G. et al., "Evidence for a long-lasting single administration contraceptive vaccine in wild grey seals", J. Reprod. Immunol., (1997) p. 43-51, vol. 35.
Brown, R.G. et al., "Temporal trends in antibody production in captive grey, harp and hooded seals to a single administration immunocontraceptive vaccine", J. Reprod. Immunol., (1997) p. 53-64, vol. 35.
Cassarino, D.S. et al., "The effects of gp100 and tyrosinase peptide vaccinations on nevi in melanoma patients", J. Cutaneous Path., (2006) p. 335-342, vol. 33.
Celis E. et al., "Recognition of hepatitis B surface antigen by human T lymphocytes. Proliferative and cytotoxic responses to a major antigenic determinant defined by synthetic peptides", Journal of Immunology. (1988) p. 1808-1815, vol. 140.
Chakraborty, M. et al., "External beam radiation of tumors alters phenotype of tumor cells to render them susceptible to vaccine-mediated T-cell killing", Cancer Research, (2004) p. 4328-4337, vol. 64.
Chen, Y.F. et al., "Cytotoxic-T-lymphocyte human papillomavirus type 16 E5 peptide with CpG-oligodeoxynucleotide can eliminate tumor growth in C57BL/6 mice", J. Virol. (Feb. 2004) p. 1333-1343, ISSN 0022-538X, vol. 78, No. 3.
Chikh, G. et al., "Liposomal delivery of CTL epitopes to dendritic cells", Biosci. Rep. (Apr. 2002) p. 339-353, ISSN 0144-8463, vol. 22, No. 2.
Chirigos, M.A. et al., "Pharmacokinetic and therapeutic activity of polyinosinic-polycytidylic acid stabilized with poly-L-lysine in carboxymethylcellulose [poly(I,C)-LC]", J Biol Response Mod, (1985) p. 621-627, vol. 4.
Choi, W-J et al., "Low toxicity cationic lipid-based emulsion for gene transfer", Biomaterials, (2004), p. 5893-5903, vol. 25.
Chong P. et al., "Identification of T- and B-cell epitopes of the S2 and S3 subunits of pertussis toxin by use of synthetic peptides", Infection and Immunity, (1992) p. 4640-4647, vol. 60.
Chung, H. et al., "Oil components modulate physical characteristics andfunction of the natural oil emulsions as drug or gene delivery system", J. Cont. Rel., (2001), p. 339-350, vol. 71.
Compagnon et al., "Targeting of Poly(rI)-Poly(rC) by Fusogenic (F Protein) Immunoliposomes", Experimental Cell Research (1992), vol. 200, 333-338.
Copland, M.J. et al., "Lipid based particulate formulations for the delivery of antigen", Immunol. Cell Biol., (2005) p. 97-105, vol. 83.
Correale, P. et al, "Fluorouracil-based chemotherapy enhances the antitumor activity of a thymidylate synthase-directed plyepitopic peptide vaccine", Journal of the National Cancer Institute, (2005) p. 1437-1445, vol. 97.
Cox, J.C. et al., "Adjuvants-a classification and review of their modes of action", Vaccine, (1997) p. 248-256, vol. 15, No. 3.
Cui, Z. et al., "Liposome-polycation-DNA (LPD) particle as a carrier and adjuvant for protein-based vaccines: Therapeutic effect against cervical cancer", Cancer Immunol. Immunother. (2005) p. 1180-1190, vol. 54.
Cui, Z. & Qui, F., "Synthetic double-stranded RNA poly(I:C) as a potent peptide vaccine adjuvant: therapeutic activity against human cervical cancer in a rodent model", Cancer Immunol Immunother, (2006) p. 1267-1269, vol. 55.
Da Silva, D.M. et al., "Heterologous boosting increases immunogenicity of chimeric papillomavirus virus-like particle vaccines", Vaccine, (2003) p. 3219-3227, vol. 21.
Daftarian, P. et al., "Eradication of established HPV 16-expressing tumors by a single administration of a vaccine composed of a liposome-encapsulated CTL-T helper fusion peptide in a water-in-oil emulsion", Vaccine (2006) p. 5236-5244. vol. 24, No. 24.
Daftarian, P. et al., "Two distinct pathways of immuno-modulation improve potency of p53 immunization in rejecting established tumors", Cancer Res., (2004) p. 5407-5414, vol. 64.
Daftarian, P. et al. "Rejection of large HPV-16 expressing tumours in aged mice by a single immunization of VacciMax® encapsulated CTL/T helper peptides", J. Trans. Med., (Jun. 2007), p. 1-9, vol. 5, No. 26.
Davis, H.L. et al., "CpG DNA Is a Potent Enhancer of Specific Immunity in Mice Immunized with Recombinant Hepatitis B Surface Antigen", J. Immunol., (1998) p. 870-876, vol. 160.
De Clercq, E. et al,"Antiviral activity of polynucleotides:copolymer of inosinic acid and N2-dimethylguanylic of 2-methylthioinosinic acid", Nucleic Acids Res, (1975) p. 121-129, vol. 2.
De Clercq, E. et al. "Interferon induction by a 2'-modified double-helical RNA, poly(2'-azido-2'-deoxyinosinic acid) . polycytidylic acid", Eur J Biochem, (1978) p. 341-349, vol. 88.
Demotz S. et al., "Delineation of several DR-restricted tetanus toxin T cell epitopes", Journal of Immunology, (1989) p. 394-402, vol. 142.
Diethelm-Okita, B.M. et al., "Universal epitopes for human CD4+ cells on tetanus and diphtheria toxins", Journal of Infectious Diseases, (2000) p. 1001-1009, vol. 181.
Dockrell and Kinghorn, "Imiquimod acid resiquimod as novel immunomodulators", Journal of Antimicrobial Chemotherapy (2001) vol. 48, p. 751-755.
Dong, L.W. et al., "Signal regulatory protein alpha negatively regulates both TLR3 and cytoplasmic pathways in type 1 Interferon induction", Mol Immunol, (2008) p. 3025-3035, vol. 45.
Dudley, M.E. et al., "Adoptive transfer of cloned melanoma-reactive T lymphocytes for the treatment of patients with metastatic melanoma", Journal of Immunotherapy, (2001) p. 363-373, vol. 24, No. 4.
Durie, B.G. et al., "Poly(I,C)-LC as an interferon inducer in refractory multiple myeloma", J Biol Response Mod., (1985) p. 518-524, vol. 4.
Edelman et al., "Adjuvants", Intern. Rev. Immunol., (1990) p. 51-66, vol. 7, No. 1.
Berzofsky et al., Jounal of Clinical Invest. 2004, vol. 113(11), p. 1515-1525.
Communication (Decision of Rejection) dated Feb. 22, 2019 in co-pending Japanese Patent Application No. 2017-138141.
Communication (Decision to Dismiss the Amendment) dated Feb. 22, 2019 in co-pending Japanese Patent Application No. 2017-138141.
YanMei Liang et al., "Toll-like receptor 2 induces mucosal homing receptor expression and IgA production by human B cells" Clinical Immunology, 2011, vol. 138, pp. 33-40.
Stefan Borsutzky et al., "The Mucosal Adjuvant Macrophage-Activating Lipopeptide-2 Directly Stimulates B Lymphocytes via the TLR2 without the Need of Accessory Cells" The Journal of Immunology, 2005, vol. 174, pp. 6308-6313.
Office Action dated Oct. 5, 2019, issued in Brazilian Application No. BR112014007927-7.
European Search Report issued in EP Application No. 12838879.0 dated Jul. 7, 2015.
"Bacterial lipopeptides activate Toll-like receptors 1, 2 and 6", microcollections, Apr. 16, 2003, P055195656.
Rosenberg et al., "Different Adjuvantcity of Incomplete Freunds Adjuvant Derived from Beef or Vegetable Components in Melanoma Patients Immunized with a Peptide Vaccine", Journal of Immunotherapy, vol. 33, No. 6, Jul. 1, 2010, pp. 626-629.
Karkada et al., "A novel breast/ovarian cancer peptide vaccine platform that promotes specific type-1 but not Treg/Tr1-type responses", Journal of Immunotherapy, vol. 33, No. 3, Apr. 1, 2010, pp. 250-261.

* cited by examiner

SEQUENCE LISTING

```
<160> NUMBER OF SEQ ID NOS: 20

<210> SEQ ID NO 1
<211> LENGTH: 6
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM, PAM2, or PAM3
<220> FEATURE:
<221> NAME/KEY: Misc_Feature
<222> LOCATION: (6)..(6)
<223> OTHER INFORMATION: Optionally conjugated to Biotin-Aca-Aca,
      Fluorescein-Aca-Aca, Rhodamine-Aca-Aca, or FLAG-tag

<400> SEQUENCE: 1

Cys Ser Lys Lys Lys Lys
              5

<210> SEQ ID NO 2
<211> LENGTH: 10
<212> TYPE: PRT
<213> ORGANISM: Artificial Sequence
<220> FEATURE:
<223> OTHER INFORMATION: Synthetic diacylated lipoprotein FSL-1
<220> FEATURE:
<221> NAME/KEY: Misc_Feature
<222> LOCATION: (1)..(1)
<223> OTHER INFORMATION: Linked to PAM or PAM2

<400> SEQUENCE: 2

Cys Gly Asp Pro Lys His Pro Lys Ser Phe
              5                  10

<210> SEQ ID NO 3
<211> LENGTH: 5
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PHC, PAM-Cys(PAM) or PAM-Dhc
<220> FEATURE:
<221> NAME/KEY: Misc_Feature
<222> LOCATION: (5)..(5)
<223> OTHER INFORMATION: Optionally conjugated to Biotin-Aca-Aca
```

<400> SEQUENCE: 3

Ser Lys Lys Lys Lys
                5

<210> SEQ ID NO 4
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 4

Cys Ser Ser Asn Ala Lys Ile Asp Gln Leu Ser Ser Asp Val Gln Thr
                5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 5

Cys Ser Ser Asn Lys Ser Thr Thr Gly Ser Gly Glu Thr Thr Thr Ala
                5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 6

Cys Ser Ser Thr Lys Pro Val Ser Gln Asp Thr Ser Pro Lys Pro Ala
                5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 7

Cys Ser Ser Gly Ser Lys Pro Ser Gly Gly Pro Leu Pro Asp Ala Lys
                5                   10                  15

<210> SEQ ID NO 8
<211> LENGTH: 16
<212> TYPE: PRT
<213> ORGANISM: Artificial Sequence
<220> FEATURE:

```
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 8

Cys Ser Ser Gly Asn Lys Ser Ala Pro Ser Ser Ala Ser Ser Ser
                 5                  10                 15

<210> SEQ ID NO 9
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 9

Cys Gly Ser His Gln Met Lys Ser Glu Gly His Ala Asn Met Gln Leu
                 5                  10                 15

<210> SEQ ID NO 10
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 10

Cys Ser Ser Ser Asn Asn Asp Ala Ala Gly Asn Gly Ala Ala Gln Thr
                 5                  10                 15

<210> SEQ ID NO 11
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 11

Cys Lys Gln Asn Val Ser Ser Leu Asp Glu Lys Asn Ser Val Ser Val
                 5                  10                 15

<210> SEQ ID NO 12
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 12

Cys Asn Asn Ser Gly Lys Asp Gly Asn Thr Ser Ala Asn Ser Ala Asp
                 5                  10                 15
```

```
<210> SEQ ID NO 13
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 13

Cys Asn Asn Gly Gly Pro Glu Leu Lys Ser Asp Glu Val Ala Lys Ser
                5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 14

Cys Ser Gln Glu Pro Ala Ala Pro Ala Ala Glu Ala Thr Pro Ala Gly
                5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 15

Cys Ser Ser Ser Lys Ser Ser Asp Ser Ser Ala Pro Lys Ala Tyr Gly
                5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 16

Cys Ala Gln Glu Lys Glu Ala Lys Ser Glu Leu Asp Tyr Asp Gln Thr
                5                   10                  15

<210> SEQ ID NO 17
<211> LENGTH: 9
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM-Dhc
```

```
<400> SEQUENCE: 17

Gly Asp Pro Lys His Pro Lys Ser Phe
                5

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
tccatgacgt tcctgacgtt                                                   20

<210> SEQ ID NO 19
<211> LENGTH: 13
<212> TYPE: PRT
<213> ORGANISM: Artificial Sequence
<220> FEATURE:
<223> OTHER INFORMATION: T Helper Epitope - PADRE
<220> FEATURE:
<221> NAME/KEY: Misc_Feature
<222> LOCATION: (3)..(3)
<223> OTHER INFORMATION: Xaa is any amino acid or cyclohexylalanyl

<400> SEQUENCE: 19

Ala Lys Xaa Val Ala Ala Trp Thr Leu Lys Ala Ala Ala
                5                   10

<210> SEQ ID NO 20
<211> LENGTH: 21
<212> TYPE: PRT
<213> ORGANISM: Artificial Sequence
<220> FEATURE:
<223> OTHER INFORMATION: T Helper Epitope - Tetanuus toxoid peptide

<400> SEQUENCE: 20

Phe Asn Asn Phe Thr Val Ser Phe Trp Leu Arg Val Pro Lys Val Ser
                5                   10                  15

Ala Ser His Leu Glu
            20
```

LIPOSOME COMPOSITIONS COMPRISING PAM2CYS OR PAM3CYS ADJUVANT AND METHODS FOR INDUCING A HUMORAL IMMUNE RESPONSE

CROSS-REFERENCE TO RELATED APPLICATIONS

This application is a continuation of U.S. patent application Ser. No. 14/347,928, filed Mar. 27, 2014 which is a U.S. National Phase of International Patent Application No. PCT/CA2012/050705, filed Oct. 5, 2012, which claims priority U.S. Provisional Application Ser. No. 61/544,020, filed Oct. 6, 2011, all of which are herein incorporated by reference in their entirety.

SEQUENCE LISTING

This application contains a Sequence Listing which has been submitted in ASCII format via EFS-Web and is hereby incorporated by reference herein in its entirety. The ASCII text file was created on Jun. 21, 2016, is named 249979_000046SeqList.txt and is 6,560 bytes in size.

FIELD OF THE INVENTION

The present application relates to vaccine compositions that enhance the production of antigen-specific antibodies in immunized subjects.

BACKGROUND OF THE INVENTION

Immune responses induced by vaccination can be categorized broadly into humoral or cellular types. A humoral response is typically desired to protect against viral or bacterial invaders, whereas immunity against virally infected cells and cancer cells typically involves a cell mediated response. Humoral immunity is typified by high levels of antibody production by B cells, whereas cellular immunity is characterized by increased activation of cytotoxic CD8 T lymphocytes.

The type of immunity induced by a vaccine largely depends on the type of adjuvant included in the vaccine. Adjuvants based on palmitic acid, such as dipalmitoyl-S-glyceryl-cysteine ($PAM_2Cys$) and tripalmitoyl-S-glyceryl-cysteine ($PAM_3Cys$) and variants thereof, have been reported to enhance humoral and cellular responses against a variety of antigens. For practical reasons, the solubility of such adjuvants has been typically improved with the addition of hydrophilic non-immunogenic amino acid residues (Lysines for example). Such adjuvants have been mixed with antigen but in many instances palmitic acid based adjuvants have been covalently linked to antigens before administering to a subject. Palmitic acid adjuvants have also been co-delivered with antigen using liposomes as carriers. Protein based and carbohydrate based antigens have been combined with palmitic acid adjuvants to produce antibody and T cell responses. The use of palmitic acid adjuvants for cancer applications is well documented, with activity mediated primarily by cellular responses.

Although palmitic acid derivatives are known to proliferate B cells, induce isotypic switching, induce differentiation of human B lymphocytes to IgG secreting plasma cells and increase expression of several co-stimulatory molecules (MHC I, II, CD80, etc), reports of palmitic acid adjuvants inducing antibody responses has varied in the literature from being able to enhance antibody responses to not being particularly useful for generating such responses.

Thus, there remains a need for the development of vaccine compositions for generating strong humoral responses against a variety of antigens. The present invention provides vaccine compositions that contain a lipid-based adjuvant and are particularly useful for inducing a high level of antibodies in immunized subjects.

SUMMARY OF THE INVENTION

In one aspect, there is provided a composition comprising: liposomes; an antigen capable of inducing a humoral immune response; a carrier comprising a continuous phase of a hydrophobic substance; and an adjuvant which activates or increases the activity of the toll-like receptor 2 (TLR2), for example, by interacting with a TLR2 dimer such as TLR1/2 or TLR2/6.

In an embodiment of the composition as described herein, the adjuvant is a lipid-based adjuvant.

In an embodiment of the composition as described herein, the lipid-based adjuvant is a palmitic acid adjuvant.

In an embodiment of the composition as described herein, the lipid-based adjuvant comprises dipalmitoyl-S-glyceryl-cysteine ($PAM_2Cys$) or tripalmitoyl-S-glyceryl-cysteine ($PAM_3Cys$); or the lipid-based adjuvant is Pam-2-Cys-Ser-(Lys)4 (SEQ ID NO: 1) or Pam-3-Cys-Ser-(Lys)4 (SEQ ID NO: 1).

In another embodiment of the composition as described herein, the lipid-based adjuvant is, or comprises: the synthetic diacylated lipoprotein FSL-1 (Pam2CGDPKHPKSF) (SEQ ID NO: 2), a synthetic lipoprotein derived from *Mycoplasma salivarium*, or the macrophage-activating lipopeptide (MALP-2) from *Mycoplasma fermentans*.

In an embodiment, the composition of the invention may comprise an adjuvant as described herein in combination with at least one other suitable adjuvant.

In another embodiment of the composition as described herein, the antigen is a polypeptide or a carbohydrate.

In an embodiment of the composition as described herein, the antigen comprises a B cell epitope, or a plurality of B cell epitopes.

In another embodiment of the composition as described herein, the antigen is a membrane surface-bound cancer antigen; a toxin; an allergen such as pollen; or an amyloid protein.

In another embodiment of the composition as described herein, the liposome comprises a phospholipid or unesterified cholesterol.

In another embodiment, the composition as described herein is capable of inducing a humoral immune response in a subject with a single dose.

The present invention in a further aspect provides a method for treating or preventing a disease or disorder ameliorated by a humoral immune response, said method comprising administering the composition as described herein to a subject.

In another aspect, the present invention provides a method for treating or preventing an infectious disease; a cancer involving a membrane surface-bound cancer antigen; or a disease or disorder where it is desirable to sequester antigen in circulation, such as an amyloid protein for treating e.g. Alzheimer's disease, said method comprising administering the composition as described herein to a subject.

In another aspect, the present invention provides a method for neutralizing a toxin, virus, bacterium or allergen, with an antibody, said method comprising administering the composition as described herein to a subject.

In an embodiment of the invention, the subject referred to herein is a mammal.

In another embodiment of the invention, the subject referred to herein is a human.

According to another aspect, the present invention relates to a kit useful for treating or preventing a disease or disorder as described herein, or neutralizing a toxin, virus, bacterium or allergen, with an antibody, wherein the kit comprises a composition as described herein, and instructions for its use thereof.

According to another aspect, the present invention relates to a method of making a composition of the present invention as described herein.

Other aspects and features of the present invention will become apparent to those of ordinary skill in the art upon review of the following description of specific embodiments of the invention in conjunction with the accompanying figures.

BRIEF DESCRIPTION OF THE FIGURES

In the figures, which illustrate embodiments of the invention by way of example only.

DETAILED DESCRIPTION

Figure 1:
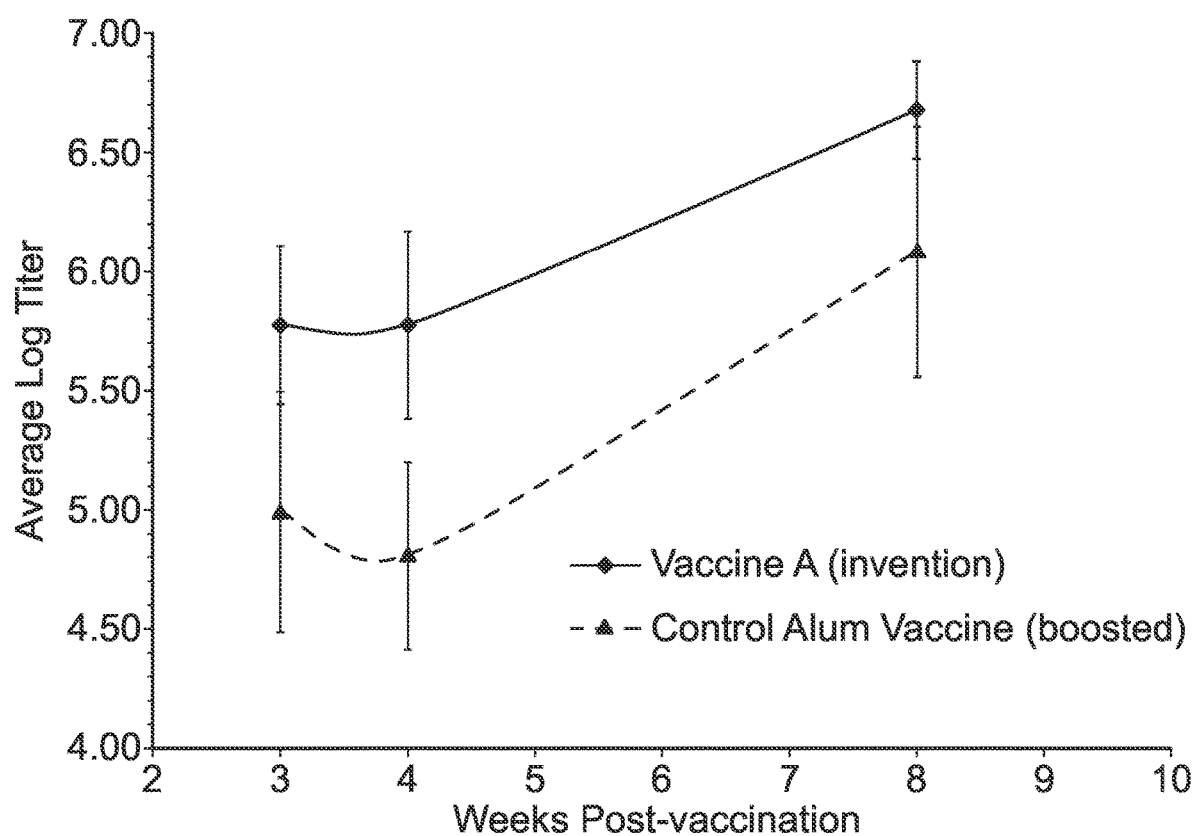
FIG. 1 illustrates the humoral immune response generated by a vaccine made in accordance with the invention ("Vaccine A"). Two groups of mice (n=8 or 9) were vaccinated as follows: Group 1 mice were vaccinated with a single dose of 1 microgram rHA and 1 microgram Pam-3-Cys-Ser-(Lys)4 (SEQ ID NO: 1) in a 50 microliter dose formulated as a water-free/liposome/P3C/hydrophobic carrier vaccine (Vaccine A). Group 2 mice were treated with 1 microgram rHA and 50 micrograms alum per 50 microliter dose of control alum vaccine; mice were boosted 28 days post-vaccination. Humoral immune responses were measured by ELISA as described above. For each treatment group, the log 10 values of the endpoint antibody titers were averaged and standard deviations calculated for each time point.

The type of immunity induced by a vaccine largely depends on the type of adjuvant included in the vaccine. The magnitude and duration of such a response depends on the type of adjuvant used as well as the composition or method by which the antigen and adjuvant are presented to the immune system. For example, live attenuated viruses can be used to deliver genes for antigens of interest that are then produced in vivo to be readily presented by antigen presenting cells; liposomes can be used to co-deliver antigen and adjuvant directly to antigen presenting cells to drive a better immune response than naked antigen and adjuvant are capable of.

The present invention provides vaccine compositions that use an adjuvant that activates or increases the activity of TLR2 to generate unexpectedly strong antibody responses. In some embodiments, vaccine compositions of the invention were capable of protecting a subject from a disease agent with as little as a single dose, whereas, as shown in the examples herein, control vaccines were unable to produce such antibody levels and are incapable of protecting vaccinated subjects to the same degree.

Compositions of the invention, combining an antigen capable of inducing a humoral immune response, an adjuvant that activates or increases the activity of TLR2, liposomes and a carrier comprising a continuous phase of a hydrophobic substance provided surprisingly higher antibody titers than aqueous aluminum based control compositions. Furthermore, a single dose of a composition of the invention was able to effectively protect mice from bacterial challenge and allow them to completely clear the infection from the lungs, which was not observed for aqueous aluminum based control compositions.

The ability to raise robust and long lasting humoral immune responses with at least one immunization using the components of the described composition of the invention (e.g. Examples 1 to 4) illustrates the particular usefulness of these compositions in a wide range of medical applications, such as for example those described herein. As shown in the examples herein, compositions of the invention can produce a strong and enhanced immune response at least as early as three weeks post-immunization, and the immune response is long-lived with antibody titers remaining high for at least twenty-four weeks post-immunization (e.g. FIG. 3).

Compositions of the invention, comprising antigen, liposomes, an adjuvant that activates or increases the activity of TLR2, and a carrier comprising a continuous phase of a hydrophobic substance, may raise robust and long lasting humoral immune responses. For example, the data described in Example 4 herein shows that antibody titers generated by mice in Group 1 (a vaccine of the invention) were significantly higher than the antibody titers generated by mice in control groups without liposomes (Group 2), without hydrophobic carrier (Group 3), or without lipid-based adjuvant (Group 4).

Thus, vaccine compositions of the invention containing a lipid-based adjuvant are capable of generating strong humoral immune responses, with high levels of antibody production, in immunized subjects.

Compositions as described herein may be useful for treating or preventing diseases and/or disorders ameliorated by humoral immune responses (e.g. involving B-cells and antibody production). The compositions find application in any instance in which it is desired to administer an antigen to a subject to induce a humoral immune response or antibody production.

As used herein, to "induce" an immune response is to elicit and/or potentiate an immune response. Inducing an immune response encompasses instances where the immune response is enhanced, elevated, improved or strengthened to the benefit of the host relative to the prior immune response status, for example, before the administration of a composition of the invention.

A humoral immune response, as opposed to cell-mediated immunity, is mediated by secreted antibodies which are produced in the cells of the B lymphocyte lineage (B cells). Such secreted antibodies bind to antigens, such as for example those on the surfaces of foreign substances and/or pathogens (e.g. viruses, bacteria, etc.) and flag them for destruction.

An "antibody" is a protein comprising one or more polypeptides substantially or partially encoded by immunoglobulin genes or fragments of immunoglobulin genes. The recognized immunoglobulin genes include the κ, λ, α, γ, δ, ε and μ constant region genes, as well as myriad immunoglobulin variable region genes. Light chains are classified as either κ or λ. Heavy chains are classified as γ, μ, α, δ, or ε, which in turn define the immunoglobulin classes, IgG, IgM, IgA, IgD and IgE, respectively. A typical immunoglobulin (antibody) structural unit comprises a protein containing four polypeptides. Each antibody structural unit is composed of two identical pairs of polypeptide chains, each having one "light" and one "heavy" chain. The N-terminus of each chain defines a variable region primarily responsible for antigen recognition. Antibody structural units (e.g. of the IgA and IgM classes) may also assemble into oligomeric forms with each other and additional polypeptide chains, for example as IgM pentamers in association with the J-chain polypeptide.

Antibodies are the antigen-specific glycoprotein products of a subset of white blood cells called B lymphocytes (B cells). Engagement of antigen with antibody expressed on the surface of B cells can induce an antibody response comprising stimulation of B cells to become activated, to undergo mitosis and to terminally differentiate into plasma cells, which are specialized for synthesis and secretion of antigen-specific antibody.

B cells are the sole producers of antibodies during an immune response and are thus a key element to effective humoral immunity. In addition to producing large amounts of antibodies, B cells also act as antigen-presenting cells and can present antigen to T cells, such as T helper CD4 or cytotoxic CD8, thus propagating the immune response. B cells, as well as T cells, are part of the adaptive immune response which is essential for vaccine efficacy. During an active immune response, induced either by vaccination or natural infection, antigen-specific B cells are activated and clonally expand. During expansion, B cells evolve to have higher affinity for the epitope. Proliferation of B cells can be induced indirectly by activated T-helper cells, and also directly through stimulation of receptors, such as the toll-like receptors (TLRs).

Antigen presenting cells, such as dendritic cells and B cells, are drawn to vaccination sites and can interact with antigens and adjuvants contained in the vaccine. The adjuvant stimulates the cells to become activated and the antigen provides the blueprint for the target. Different types of adjuvants provide different stimulation signals to cells. For example, Poly I:C (a TLR3 agonist) can activate dendritic cells, but not B cells. Adjuvants such as Pam3Cys, Pam2Cys and FSL-1 are especially adept at activating and initiating proliferation of B cells, which is expected to facilitate the production of an antibody response (Moyle et al., *Curr Med Chem*, 2008; So., *J Immunol*, 2012).

As used herein, the term "antibody response" refers to an increase in the amount of antigen-specific antibodies in the body of a subject in response to introduction of the antigen into the body of the subject.

One method of evaluating an antibody response is to measure the titers of antibodies reactive with a particular antigen. This may be performed using a variety of methods known in the art such as enzyme-linked immunosorbent assay (ELISA) of antibody-containing substances obtained from animals. For example, the titers of serum antibodies which bind to a particular antigen may be determined in a subject both before and after exposure to the antigen. A statistically significant increase in the titer of antigen-specific antibodies following exposure to the antigen would indicate the subject had mounted an antibody response to the antigen.

Other assays that may be used to detect the presence of an antigen-specific antibody include, without limitation, immunological assays (e.g. radioimmunoassay (RIA)), immunoprecipitation assays, and protein blot (e.g. Western blot) assays; and neutralization assays (e.g., neutralization of viral infectivity in an in vitro or in vivo assay).

The compositions of the present invention, by stimulating strong antibody responses, may be capable of protecting a subject from a disease, disorder or ailment associated with an antigen capable of inducing a humoral immune response.

Without limitation, this includes for example, infectious diseases, cancers involving a membrane surface-bound cancer antigen which is recognized by an antibody, diseases where it is desirable to sequester antigen in circulation, like amyloid protein (e.g. Alzheimer's disease); neutralizing toxins with an antibody; neutralizing viruses or bacteria with an antibody; or neutralizing allergens (e.g. pollen) for the treatment of allergies.

"Humoral immune response" as referred to herein relates to antibody production and the accessory processes that accompany it, such as for example T-helper 2 (Th2) cell activation and cytokine production, isotype switching, affinity maturation and memory cell activation. It also refers to the effector functions of an antibody, such as for example toxin neutralization, classical complement activation, and promotion of phagocytosis and pathogen elimination. The humoral immune response is aided by CD4+Th2 cells and therefore the activation or generation of this cell type is also indicative of a humoral immune response as referred to herein.

A "humoral immune response" as referred to herein may also encompass the generation and/or activation of T-helper 17 (Th17) cells. Th17 cells are a subset of helper-effector T-lymphocytes characterized by the secretion of host defense cytokines such as IL-17, IL-17F and IL-22. Th17 cells are considered developmentally distinct from Th1 and Th2 cells, and have been postulated to facilitate the humoral immune response, such as for example, providing an important function in anti-microbial immunity and protecting against infections. Their production of IL-22 is thought to stimulate epithelial cells to produce anti-microbial proteins and production of IL-17 may be involved in the recruitment, activation and migration of neutrophils to protect against host infection by various bacterial and fungal species.

A humoral immune response is the main mechanism for effective infectious disease vaccines. However, a humoral immune response can also be useful for combating cancer. Unlike a cancer vaccine designed to produce a cytotoxic CD8 T cell response that can recognize and destroy cancer cells, B cell mediated responses may target cancer cells through other mechanisms which may in some instances cooperate with a cytotoxic CD8 T cell for maximum benefit. Examples of mechanisms of B cell mediated (e.g. humoral immune response mediated) anti-tumor responses include, without limitation: 1) Antibodies produced by B cells that bind to surface antigens found on tumor cells or other cells that influence tumorigenesis. Such antibodies can, for example. induce killing of target cells through antibody-dependant cell-mediated cytotoxicity (ADCC) or complement fixation, potentially resulting in the release of additional antigens that can be recognized by the immune system; 2) Antibodies that bind to receptors on tumor cells to block their stimulation and in effect neutralize their effects; 3) Antibodies that bind to factors released by or associated with tumor or tumor-associated cells to modulate a signaling or cellular pathway that supports cancer; and 4) Antibodies that bind to intracellular targets and mediate anti-tumor activity through a currently unknown mechanism.

Several methods can be used to demonstrate the induction of humoral immunity following vaccination. These can be broadly classified into detection of: i) specific antigen presenting cells; ii) specific effector cells and their functions; and iii) release of soluble mediators such as cytokines.

i) Antigen Presenting Cells:

Dendritic cells and B-cells (and to a lesser extent macrophages) are equipped with special immuno-stimulatory receptors that allow for enhanced activation of T cells, and are termed professional antigen presenting cells (APC). These immuno-stimulatory molecules (also called as co-stimulatory molecules) are up-regulated on these cells following infection or vaccination, during the process of antigen presentation to effector cells such as CD4 and CD8 cytotoxic T cells. Such co-stimulatory molecules (such as CD80, CD86, MHC class I or MHC class II) can be detected by using flow cytometry with fluorochrome-conjugated antibodies directed against these molecules along with antibodies that specifically identify APC (such as CD11c for dendritic cells).

ii) Cd4+"Helper" T-Cells:

CD4+ lymphocytes, or helper T cells, are immune response mediators, and play an important role in establishing and maximizing the capabilities of the adaptive immune response. These cells have no cytotoxic or phagocytic activity; and cannot kill infected cells or clear pathogens, but, in essence "manage" the immune response, by directing other cells to perform these tasks. Two types of effector CD4+T helper cell responses can be induced by a professional APC, designated Th1 and Th2, each designed to eliminate different types of pathogens.

Helper T cells express T-cell receptors (TCR) that recognize antigen bound to Class II MHC molecules. The activation of a naive helper T-cell causes it to release cytokines, which influences the activity of many cell types, including the APC that activated it. The two Th cell populations, Th1 and Th2, differ in the pattern of the effector proteins (cytokines) produced. In general, Th1 cells assist the cellular immune response by activation of macrophages and cytotoxic T-cells; whereas Th2 cells promote the humoral immune response by stimulation of B-cells for conversion into plasma cells and by formation of antibodies. A response regulated by Th2 type cells may predominantly enhance the production of IgG1 in mouse (IgG2 in humans). The measure of cytokines associated with Th1 or Th2 responses will give a measure of successful vaccination. This can be achieved by specific ELISA designed for Th1-cytokines such as IFN-γ, IL-2, IL-12, TNF-α and others, or Th2-cytokines such as IL-4, IL-5, IL10 among others.

Another Th cell population is the Th17 cell. The measure of cytokines associated with Th17 cells can also give a measure of a successful vaccination. This can be achieved, for example, by specific ELISA designed for Th17 cytokines such as IL-17, IL-17F and IL-22.

iii) Measurement of Cytokines:

released from regional lymph nodes gives a good indication of successful immunization. As a result of antigen presentation and maturation of APC and immune effector cells such as CD4 and CD8 T cells, several cytokines are released by lymph node cells. By culturing these LNC in vitro in the presence of antigen, an antigen-specific immune response can be detected by measuring release if certain important cytokines such as IL-4, IL-5, and IL10 for detection of a humoral immune response. This could be done by ELISA using culture supernatants and recombinant cytokines as standards.

Successful immunization may further be determined in a number of additional ways known to the skilled person including, but not limited to, hemagglutination inhibition (HAI) and serum neutralization inhibition assays to detect functional antibodies; challenge studies, in which vaccinated subjects are challenged with the associated pathogen to determine the efficacy of the vaccination; and the use of fluorescence activated cell sorting (FACS) to determine the population of cells that express a specific cell surface marker, e.g. in the identification of activated or memory lymphocytes. Also, vaccine efficacy in stimulating a humoral immune response can be assessed by ELISA detection of antigen-specific antibody levels in the serum of immunized subjects. A skilled person may also determine if immunization with a composition of the invention elicited a humoral (or antibody mediated) response using other known methods. See, for example, Current Protocols in Immunology Coligan et al., ed. (Wiley Interscience, 2007). The term "infectious disease", as used herein, may refer for example to any communicable disease, contagious disease or transmissible disease resulting from the infection, presence and/or growth of pathogenic biological agents. Without limitation, an infectious pathogenic agent may include for example viruses, bacteria, fungi, protozoa, and parasites. Non-limiting examples of infectious diseases include influenza (e.g. infection by influenza virus), respiratory tract infections such as, for example, bronchiolitis and pneumonia (e.g. infection by respiratory syncytial virus), pertussis or whooping cough (e.g. infection by *Bordetella pertussis*), anthrax (e.g. infection by *Bacillus anthracis*) and malaria (e.g. infection by *Plasmodium malariae, Plasmodium falciparum, Plasmodium vivax, Plasmodium ovale* or *Plasmodium knowlesi*).

As used herein, the terms "cancer", "cancer cells", "tumor" and "tumor cells", (used interchangeably) refer to cells that exhibit abnormal growth, characterized by a significant loss of control of cell proliferation or cells that have been immortalized. The term "cancer" or "tumor" includes metastatic as well as non-metastatic cancer or tumors. A cancer may be diagnosed using criteria generally accepted in the art, including the presence of a malignant tumor.

A "toxin", as used herein, refers to any substance produced by living cells or organisms (e.g. plants, animals, microorganisms, etc.) that is capable of causing a disease or ailment, or an infectious substance, or a recombinant or synthesized molecule capable of adverse effect. Toxins may be for example small molecules, peptides, or proteins. Toxins include drug substances such as, for example, cocaine.

An "allergen", as used herein, refers to any substance that can cause an allergy. The allergen and may be derived from, without limitation, cells, cell extracts, proteins, polypeptides, peptides, polysaccharides, polysaccharide conjugates, peptide and non-peptide mimics of polysaccharides and other molecules, small molecules, lipids, glycolipids, and carbohydrates of plants, animals, fungi, insects, food, drugs, dust, and mites. Allergens include but are not limited to environmental aeroallergens; plant pollens (e.g. ragweed/hayfever); weed pollen allergens; grass pollen allergens; Johnson grass; tree pollen allergens; ryegrass; arachnid allergens (e.g. house dust mite allergens); storage mite allergens; Japanese cedar pollen/hay fever; mold/fungal spore allergens; animal allergens (e.g., dog, guinea pig, hamster, gerbil, rat, mouse, etc., allergens); food allergens (e.g. crustaceans; nuts; citrus fruits; flour; coffee); insect allergens (e.g. fleas, cockroach); venoms: (Hymenoptera, yellow jacket, honey bee, wasp, hornet, fire ant); bacterial allergens (e.g. streptococcal antigens; parasite allergens such as *Ascaris* antigen); viral antigens; drug allergens (e.g. penicillin); hormones (e.g. insulin); enzymes (e.g. streptokinase); and drugs or chemicals capable of acting as incomplete antigens or haptens (e.g. the acid anhydrides and the isocyanates).

Where a hapten is used in a composition of the invention, it may be attached to a carrier, such as for example a protein, to form a hapten-carrier adduct. The hapten-carrier adduct is capable of initiating a humoral immune response, whereas the hapten itself would not elicit antibody production. Non-limiting examples of haptens are aniline, urushiol (a toxin in poison ivy), hydralazine, fluorescein, biotin, digoxigenin and dinitrophenol.

"Treating" or "treatment of", or "preventing" or "prevention of", as referred to herein refers to an approach for obtaining beneficial or desired results, including clinical results. Beneficial or desired clinical results can include, but are not limited to, alleviation or amelioration of one or more symptoms or conditions, diminishment of extent of disease, stabilisation of the state of disease, prevention of development of disease, prevention of spread of disease, delay or slowing of disease progression, delay or slowing of disease onset, conferring protective immunity against a disease-causing agent and amelioration or palliation of the disease state. "Treating" or "preventing" can also mean prolonging survival of a patient beyond that expected in the absence of treatment and can also mean inhibiting the progression of disease temporarily, although more preferably, it involves preventing the occurrence of disease such as by preventing infection in a subject.

The subject to be treated may be any vertebrate, preferably a mammal, more preferably a human.

Adjuvants

Suitable adjuvants of the composition of the invention are adjuvants that activate or increases the activity of TLR2. In some embodiments, the adjuvant is a lipid-based adjuvant, which encompasses any adjuvant that comprises at least one lipid moiety or lipid component.

As used herein, the expression "lipid moiety" or "lipid component" refers to any fatty acid (e.g. fatty acyls) or derivative thereof, including for example triglycerides, diglycerides, and monoglycerides. Exemplary fatty acids include, without limitation, palm itoyl, myristoyl, stearoyl and decanoyl groups or any C2 to C30 saturated or unsaturated fatty acyl group, preferably any C14 to C22 saturated or unsaturated fatty acyl group, and more preferably a C16 saturated or unsaturated fatty acyl group. Thus, as referred to herein, the expression "lipid-based adjuvant" encompasses any adjuvant comprising a fatty acyl group or derivative thereof.

Lipid-based adjuvants of the present invention contain at a minimum at least one lipid moiety, or a synthetic/semi-synthetic lipid moiety analogue, which can be coupled onto an amino acid, an oligopeptide or other molecules (e.g. a carbohydrate, a glycan, a polysaccharide, biotin, Rhodamine, etc.). Thus, without limitation, the lipid-based adjuvant may be, for example, a lipoamino acid, a lipopeptide, a lipoglycan, a lipopolysaccharide or a lipoteichoic acid. Moreover, a lipid moiety or a structure containing a lipid moiety can be coupled covalently or non-covalently to an antigen to create antigenic compounds with built-in adjuvanting properties. For example, and without limitation, the lipid-based moiety may comprise a cation (e.g. nickel) to provide a positive charge for non-covalent coupling.

In some embodiments, the lipid moiety or lipid component may be naturally occurring, such as for example a cell-wall component (e.g. lipoprotein) from a Gram-positive or Gram-negative bacteria, *Rhodopseudomonas viridis*, or *mycoplasma*. In other embodiments, the lipid moiety or lipid component may be synthetic or semi-synthetic.

The lipid-based adjuvant may comprise palmitic acid (PAM) as at least one of the lipid moieties or components of the adjuvant. Such lipid-based adjuvants are referred to herein as a "palmitic acid adjuvant". Palmitic acid is a low molecular weight lipid found in the immunologically reactive Braun's lipoprotein of *Escherichia coli*. Other common chemical names for palmitic acid include, for example, hexadecanoic acid in IUPAC nomenclature and 1-Pentadecanecarboxylic acid. The molecular formula of palmitic acid is $CH_3(CH_2)_{14}CO_2H$. As will be understood to those skilled in the art, it is possible that the lipid chain of palmitic acid may be altered. Exemplary compounds which may be used herein as palmitic acid adjuvants, and methods for their synthesis, are described for example in United States Patent Publications US 2008/0233143; US 2010/0129385; and US 2011/0200632, the disclosures of which are incorporated herein.

As described above for lipid moieties generally, a palmitic acid adjuvant contains at a minimum at least one palmitic acid moiety, which can be coupled onto an amino acid, an oligopeptide or other molecules. A palmitic acid moiety or a structure containing palmitic acid can be coupled covalently or non-covalently to an antigen to create antigenic compounds with built-in adjuvanting properties. The palmitic acid moiety or a chemical structure containing palmitic acid can be conjugated to a cysteine peptide (Cys) to allow for various structural configurations of the adjuvant, including linear and branched structures. The cysteine residue has been commonly extended by polar residues such as Serine (Ser) and/or lysine (Lys) at the C terminus to create adjuvant compounds with improved solubility. Palmitic acid containing adjuvant compounds could be admixed with an antigen, associated with antigen through non-covalent interactions, or alternatively covalently linked to an antigen, either directly or with the use of a linker/spacer, to generate enhanced immune responses. Most commonly, two palmitic acid moieties are attached to a glyceryl backbone and a cysteine residue to create dipalmitoyl-S-glyceryl-cysteine ($PAM_2Cys$) or tripalmitoyl-S-glyceryl-cysteine ($PAM_3Cys$), which can also be used in multiple configurations as described above.

Palmitic acid adjuvants are known to activate B cells causing rapid proliferation and production of antibodies. B cells recognize the antigen co-delivered with the adjuvant in the vaccine formulation and through affinity maturation will proliferate with increasing specificity towards the antigen. Activated B cells are known to secrete large quantities of soluble immunoglobin antibodies that can bind to soluble targets, such as bacteria, present in the blood. Antibody effector functions are i) opsonization; ii) antibody-dependent cell-mediated cytotoxicity (ADCC); iii) complement activation; iv) neutralization. While the majority of the B cells will mature into antibody secreting plasma cells, a portion should differentiate into memory B cells that persist after the immune response has controlled infection. This provides long-term immunity against subsequent exposure to the pathogen. Ideally, a prophylactic vaccine should induce a strong memory B cell population.

Therefore, in an embodiment, the adjuvant of the composition of the invention is any type of adjuvant comprising a palmitic acid moiety or component. The palmitic acid moiety may be modified or manipulated to improve its stability in vitro or in vivo, enhance its binding to receptors (such as for example toll-like receptors as described below) or enhance its biological activity.

In a particular embodiment, the palmitic acid adjuvant may comprise $PAM_2Cys$.

In another particular embodiment, the palmitic acid adjuvant may comprise $PAM_3Cys$.

In another particular embodiment, the palmitic acid adjuvant may be Pam-2-Cys-Ser-(Lys)4 (SEQ ID NO: 1) or Pam-3-Cys-Ser-(Lys)4 (SEQ ID NO: 1). Such palmitic acid adjuvants are available, for example, as research reagents from EMC Microcollections GmbH (Germany) and InvivoGen (San Diego, Calif., USA).

Also available from EMC Microcollections are various analogs of Pam-2-Cys-Ser-(Lys)4 (SEQ ID NO: 1) and Pam-3-Cys-Ser-(Lys)4 (SEQ ID NO: 1), including labelled analogs. These analogs are encompassed herein and include, without limitation, $PAM_3Cys$-SKKKK (SEQ ID NO: 1) (β-irradiated), R-$PAM_3Cys$-SKKKK (SEQ ID NO: 1), S-$PAM_3Cys$-SKKKK (SEQ ID NO: 1), $PAM_3Cys$-SKKKK (Biotin-Aca-Aca) (SEQ ID NO: 1), $PAM_3Cys$-SKKKK (Fluorescein-Aca-Aca) (SEQ ID NO: 1), $PAM_3Cys$-SKKKK(Rhodamine-Aca-Aca) (SEQ ID NO: 1), $PAM_3Cys$-SKKKK-FLAG-tag (SEQ ID NO: 1), PHC-SKKKK (SEQ ID NO: 3), PHC-SKKKK(Biotin-Aca-Aca) (SEQ ID NO: 3), $PAM_3Cys$-SSNAKIDQLSSDVQT (SEQ ID NO: 4), $PAM_3Cys$-SSNKSTTGSGETTTA (SEQ ID NO: 5), $PAM_3Cys$-SSTKPVSQDTSPKPA (SEQ ID NO: 6), $PAM_3Cys$-SSGSKPSGGPLPDAK (SEQ ID NO: 7), $PAM_3Cys$-SSGNKSAPSSSASSS (SEQ ID NO: 8), $PAM_3Cys$-GSHQMKSEGHANMQL (SEQ ID NO: 9), $PAM_3Cys$-SSSNNDAAGNGAAQT (SEQ ID NO: 10), $PAM_3Cys$-KQNVSSLDEKNSVSV (SEQ ID NO: 11), $PAM_3Cys$-NNSGKDGNTSANSAD (SEQ ID NO: 12), $PAM_3Cys$-NNGGPELKSDEVAKS (SEQ ID NO: 13), $PAM_3Cys$-SQEPAAPAAEATPAG (SEQ ID NO: 14), $PAM_3Cys$-SSSKSSDSSAPKAYG (SEQ ID NO: 15), $PAM_3Cys$-AQEKEAKSELDYDQT (SEQ ID NO: 16), $Pam_2Cys$-SKKKK (mixture of RR and RS stereoisomers) (SEQ ID NO: 1), R-$Pam_2Cys$-SKKKK (RR stereoisomer) (SEQ ID NO: 1), S-$Pam_2Cys$-SKKKK (RS stereoisomer) (SEQ ID NO: 1), PamCys(Pam)-SKKKK (SEQ ID NO: 3), $Pam_2Cys$-SKKKK(Biotin-Aca-Aca)-$NH_2$ (SEQ ID NO: 1), $Pam_2Cys$-SKKKK(Fluorescein-Aca-Aca)-$NH_2$ (SEQ ID NO: 1), $PAM_2Cys$-SKKKK(Rhodamine-Aca-Aca)—$NH_2$ (SEQ ID NO: 1), and $PAM_2Cys$-SKKKK-FLAG-tag (SEQ ID NO: 1). Where appropriate, the palmitic acid adjuvant or analog thereof may used as stereochemically defined compounds or as a mixture of stereoisomers.

The adjuvant is one that activates or increases the activity of toll-like receptors (TLRs), and preferably activates or increases the activity of TLR2. As used herein, an adjuvant which "activates" or "increases the activity" of a TLR includes any adjuvant, in some embodiments a lipid-based adjuvant, which acts as a TLR agonist. Further, activating or increasing the activity of TLR2 encompasses its activation in any monomeric, homodimeric or heterodimeric form, and particularly includes the activation of TLR2 as a heterodimer with TLR1 or TLR6 (i.e. TLR1/2 or TLR2/6), as described in further detail below.

TLRs are a conserved family of transmembrane spanning receptors found primarily on leukocytes such as dendritic cells (DCs) and macrophages, professional antigen presenting cells. TLRs have specifically evolved to recognize and induce an immune response to pathogen associated molecular patterns, such as for example bacterial lipoproteins and lipopeptides and viral double stranded RNA. More than 10 distinct TLRs have been identified in mice and humans, although the ligand and signalling pathways are not yet known for some (see Table 1 below). There are 13 identified TLRs in humans, numbered 1 through 13.

| Receptor | Type of Agonist | Adaptor Molecule | Cellular Location | Agonist Examples |
|---|---|---|---|---|
| TLR1/2 | Bacterial lipopeptides | MyD88 | Surface | Pam3 Cys |
| TLR3 | dsRNA | TRIF | Intracellular | Poly I:C |
| TLR4 | Lipopolysaccharide | MyD88/ TRIF | Surface | LPS, MPL |
| TLR5 | Protein | MyD88 | Surface | Flagellin |
| TLR2/6 | Bacterial diacyl lipopeptides | MyD88 | Surface | Zymosan, Pam2 Cys |
| TLR7 | ssRNA | MyD88 | Intracellular | Imiquimod, Loxoribine |
| TLR8 | ssRNA, small synthetic compounds | MyD88 | Intracellular | Resiquimod, R848 |
| TLR9 | Unmethlyated DNA | MyD88 | Intracellular | CpG |

TLRs typically form homodimers, with the exception of TLR2 which forms a heterodimer with TLR1 or TLR6 resulting in differing ligand specificity. TLR2 mediates downstream signalling, so these heterodimers are often referred to collectively as TLR2 (Takeuchi, O. and S. Akira, Cell, 2010, 140(6): p. 805-20). Stimulation of the TLRs on DCs results in upregulation of MHC and co-stimulatory molecules, which enhance the antigen presenting function of these cells, as well as the production of Th1-type cytokines and promotion of cross-presentation (Lahiri et al., Vaccine, 2008, 26(52): p. 6777-83; Welters et al., Vaccine, 2007, 25(8): p. 1379-89; Matsumoto et al., Adv Drug Deliv Rev, 2008, 60(7): p. 805-12; Blander, J. M., Ann Rheum Dis, 2008, 67 Suppl 3: p. iii44-9). Because stimulation through TLRs has a direct effect on boosting the immune response, TLR agonists have been studied as potential adjuvants (Barchet et al., Curr Opin Immunol, 2008, 20(4): p. 389-95).

TLRs have a conserved cytosolic domain termed the Toll-interleukin 1 receptor (TIR) which is associated with an adaptor molecule that facilitates downstream signalling pathways leading to cellular activation. TLRs could be broadly categorized by the adaptor protein they are associated with, MyD88 or TRIF. TLR4 alone can signal through both pathways. Both signalling pathways converge on the activation of the transcription factor NF-KB (Ouyang et al., Biochem Biophys Res Commun, 2007, 354(4): p. 1045-51). Several studies have demonstrated that although different TLRs share some downstream signalling molecules, each receptor produces a unique profile of pro-inflammatory mediators (Welters et al., Vaccine, 2007, 25(8): p. 1379-89; Seya et al., Evid Based Complement Alternat Med, 2006, 3(1): p. 31-8 and discussion 133-7; Ghosh et al., Cell Immunol, 2006, 243(1): p. 48-57; Re, F. and Strominger, J. L., J Immunol, 2004, 173(12): p. 7548-55; Avril et al., J Immunother, 2009, 32(4): p. 353-62). The full downstream pathway for TLR receptors are not fully elucidated, but differences in activation could be the result of the strength of the ligand, subcellular location of the receptor, cell type and the presence of interferon regulatory factors (IRF).

Palmitic acid adjuvants have been reported to signal through toll-like receptor 2 (TLR2). For example, $PAM_2Cys$ is recognized by the heterodimer TLR2 and TLR6. Also as an example, $PAM_3Cys$, which is recognized by the heterodimer TLR1 and TLR2, triggers an anti-bacterial response typified by humoral activity. In contrast double stranded RNA from viruses is recognized by TLR3 and induces an anti-viral response that is usually characterized by interferon release and T cell activity. Mediating cellular responses has been associated with TLR2.

$Pam_3Cys$ has been tested in a variety of animal models and in Phase I clinical trial in humans with no reported side effects (Moyle, P. M. and Toth. I., Curr Med Chem, 2008, 15(5): p. 506-16; Wiedemann et al., J Pathol, 1991, 164(3): p. 265-71). In a screen of TLR agonists on murine DCs, stimulation with $Pam_3Cys$ in vitro produced high levels of the pro-inflammatory cytokines IL-12p40, IL-6 and TNFα that was attained with only small amounts of the adjuvant relative to other TLR agonists tested (Welters et al., Vaccine, 2007, 25(8): p. 1379-89).

As will be appreciated by those skilled in the art, the present invention encompasses adjuvants that activate or increase the activity of a TLR, or acts as an agonist to a TLR, particularly a lipid-based adjuvant. In a particular embodiment, the lipid-based adjuvant activates or increases the activity of TLR2. Without limitation, such lipid-based adjuvants may be a palmitic acid adjuvant which activates or increases the activity of a TLR, such as a palmitic acid adjuvant comprising $PAM_2Cys$ or $PAM_3Cys$.

Other exemplary TLR2 agonists which may be used as a lipid-based adjuvant in the composition of the invention include, without limitation, cell-wall components such as lipoteichoic acid and lipoprotein from Gram-positive bacteria, and lipoarabinomannan from mycobacteria. A number of these cell-wall components are available from InvivoGen (San Diego, Calif., USA), such as lipoarabinomannan from M. smegmatis (LAM-MS), lipomannan from M. smegmatis (LM-MS), lipopolysaccharide from P. gingivalis (LPS-PG Ultrapure), and lipoteichoic acid from B. subtilis (LTA-BS) and S. aureus (LTA-SA). In some embodiments, the lipid-based adjuvant that activates or increases the activity of TLR2 may encompass a heat-killed bacteria that comprises any one or more of the cell-wall components described above. Such heat-killed bacteria are available, for example, from InvivoGen (San Diego, Calif., USA).

Synthetic lipoproteins that act as TLR agonists are also encompassed by the invention, and include without limitation the palmitic acid adjuvants and analogs described above and synthetic diacylated lipoprotein FSL-1 available from InvivoGen (San Diego, Calif., USA) and EMC Microcollections GmbH (Germany). FSL-1 (Pam2CGDPKHPKSF; SEQ ID NO: 2) is a synthetic lipoprotein that represents the N-terminal part of the 44-kDa lipoprotein LP44 of *Mycoplasma salivarium*. FSL-1 comprises PAM$_2$Cys and has a similar framework structure as macrophage activating lipopeptide-2 (MALP-2), a *Mycoplasma fermentans* derived lipopeptide. It is postulated that FSL-1 and MALP-2, containing a lipolyated N-terminal diacylated cysteine residue, are recognized by dimer TLR2 and TLR6 9TLR2/6). Synthetic MALP-2 is available from Enzo Life Sciences (Farmingdale, N.Y., USA).

In an embodiment, the lipid-based adjuvant of the invention comprises FSL-1 or MALP-2, or the lipid-based adjuvant is FSL-1 or MALP-2. Where appropriate, FSL-1 or MALP-2 may used as stereochemically defined compounds or as a mixture of stereoisomers. The FSL-1 or MALP-2 may be labelled (e.g. biotin, Fluorescein, Rhodamine, etc.). FSL-1 is also available as a FSL-1 Ala-scan collection (EMC Microcollections) comprising nine different FSL-1-Ala compounds. Each of these FSL-1-Ala molecules is encompassed herein individually or in combination.

Further embodiments of lipid-based adjuvants of the invention may include substructures of TLR2 ligands such as monoacylated lipopeptides. Without limitation, these may include, for example, Pam-Dhc-SKKKK (SEQ ID NO: 3), Pam-CSKKKK (SEQ ID NO: 1), Pam-Dhc-GDPKHPKSF (SEQ ID NO: 17) or Pam-CGDPKHPKSF (SEQ ID NO: 2) (EMC Microcollections).

Other lipid-based adjuvants that activate or increase the activity of TLR2 can be identified, for example, by using the InvivoGen (San Diego, Calif., USA) HEK-Blue® TLR2 activation reporter system. This system allows for evaluation of the ability of potential TLR2 ligands to stimulate TLR2 in either human (hTLR2) or murine (mTLR2) cells.

In some embodiments, the lipid-based adjuvant of the compositions of the invention is one that activates or increases the activity of only TLR2, heterodimer TLR1 and TLR2 (TLR1/2), and/or heterodimer TLR2 and TLR6 (TLR2/6), while other TLRs are not activated. In a further embodiment, the lipid-based adjuvant activates or increases only the activity of heterodimer TLR1/2 and/or TLR2/6, but does not activate other TLRs.

The composition of the invention may comprise an adjuvant as described above in combination with at least one other suitable adjuvant. Exemplary embodiments of the at least one other adjuvant encompasses, but is by no means limited to, organic and inorganic compounds, polymers, proteins, peptides, sugars from synthetic, non-biological or biological sources (including but not limited to virosomes, virus-like particles, viruses and bacteria of their components).

Further examples of compatible adjuvants may include, without limitation, chemokines, Toll like receptor agonists, colony stimulating factors, cytokines, 1018 ISS, aluminum salts, Amplivax, AS04, AS15, ABM2, Adjumer, Algammulin, AS01B, AS02 (SBASA), ASO2A, BCG, Calcitriol, Chitosan, Cholera toxin, CP-870,893, CpG, polyiC, CyaA, Dimethyldioctadecylammonium bromide (DDA), Dibutyl phthalate (DBP), dSLIM, Gamma inulin, GM-CSF, GMDP, Glycerol, IC30, IC31, Imiquimod, ImuFact IMP321, IS Patch, ISCOM, ISCOMATRIX, JuvImmune, LipoVac, LPS, lipid core protein, MF59, monophosphoryl lipid A, Montanide® IMS1312, Montanide® based adjuvants, OK-432, OM-174, OM-197-MP-EC, ONTAK, PepTel vector system, other palmitoyl based molecules, PLG microparticles, resiquimod, squalene, SLR172, YF-17 DBCG, QS21, QuilA, P1005, Poloxamer, Saponin, synthetic polynucleotides, Zymosan, pertussis toxin.

Accordingly, the composition may comprise one or more pharmaceutically acceptable adjuvants, where at least one of the adjuvants of the composition is an adjuvant that activates or increases the activity of TLR2.

In another embodiment, the antigen may be coupled to a lipid moiety, such as for example a palmitic acid moiety, to provide the adjuvanting property. The composition may also comprise further pharmaceutically acceptable excipients, diluents, etc., as known in the art. See, for example, Remington's Pharmaceutical Sciences (Remington's Pharmaceutical Sciences, Mack Publishing Company, Easton, Pa., USA 1985) and The United States Pharmacopoeia: The National Formulary (USP 24 NF19) published in 1999.

In an embodiment, such additional suitable adjuvants may comprise a CpG-containing oligodeoxynucleotide (CpG ODN), such as 5'-TCCAT<u>GACGTT</u>CCT<u>GACGTT</u>-3' (SEQ ID NO: 18). The skilled person may select an appropriate CpG on the basis of the target species and efficacy.

The amount of adjuvant used depends on the amount of antigen and on the type of adjuvant. One skilled in the art can readily determine the amount of adjuvant needed in a particular application by empirical testing.

Antigens

The compositions of the invention comprise one or more antigens. As used herein, the term "antigen" refers to a substance that can bind specifically to an antibody. Suitable antigens of the composition are those that are capable of inducing a humoral immune response in a subject.

Antigens useful in the compositions of the invention include, without limitation, polypeptides, carbohydrates, a microorganism or a part thereof, such as a live, attenuated, inactivated or killed bacterium, virus or protozoan, or part thereof. The antigen may be, for example, a pathogenic biological agent, a toxin, an allergen, a peptide, a suitable native, non-native, recombinant or denatured protein or polypeptide, or a fragment thereof, or an epitope that is capable of producing a humoral immune response in a subject.

As used herein and in the claims, the term "antigen" also includes a polynucleotide that encodes the polypeptide that functions as an antigen. Nucleic acid-based vaccination strategies are known, wherein a vaccine composition that contains a polynucleotide is administered to a subject. The antigenic polypeptide encoded by the polynucleotide is expressed in the subject, such that the antigenic polypeptide is ultimately present in the subject, just as if the vaccine composition itself had contained the polypeptide. For the purposes of the present invention, the term "antigen", where the context dictates, encompasses such polynucleotides that encode the polypeptide which functions as the antigen.

Polypeptides or fragments thereof that may be useful as antigens in the invention include, without limitation, those derived from Cholera toxoid, tetanus toxoid, diphtheria toxoid, hepatitis B surface antigen, hemagglutinin (e.g. H5N1 recombinant hemagglutinin protein), anthrax recombinant protective antigen (List Biologics; Campbell, Calif.), neuraminidase, influenza M protein, PfHRP2, pLDH, aldolase, MSP1, MSP2, AMA1, Der-p-1, Der-f-1, Adipophilin, AFP, AIM-2, ART-4, BAGE, α-feto protein, BCL-2, Bcr-Abl, BING-4, CEA, CPSF, CT, cyclin D1Ep-CAM, EphA2, EphA3, ELF-2, FGF-5, G250, Gonadotropin Releasing Hormone, HER-2, intestinal carboxyl esterase (iCE), IL13Rα2, MAGE-1, MAGE-2, MAGE-3, MART-1, MART-2, M-CSF, MDM-2, MMP-2, MUC-1, NY-EOS-1, MUM-1, MUM-2, MUM-3, pertussis toxoid protein, p53, PBF, PRAME, PSA, PSMA, RAGE-1, RNF43, RU1, RU2AS, SART-1, SART-2, SART-3, SAGE-1, SCRN 1, SOX2, SOX10, STEAP1, survivin, Telomerase, TGβRII, TRAG-3, TRP-1, TRP-2, TERT and WT1.

Viruses, or parts thereof, useful as antigens in the invention include, without limitation, Cowpoxvirus, Vaccinia virus, Pseudocowpox virus, Human herpesvirus 1, Human herpesvirus 2, Cytomegalovirus, Human adenovirus A-F, Polyomavirus, Human papillomavirus, Parvovirus, Hepatitis A virus, Hepatitis B virus, Hepatitis C virus, Human immunodeficiency virus, Orthoreovirus, Rotavirus, Ebolavirus, parainfluenza virus, influenza virus (e.g. H5N1 influenza virus, influenza A virus, influenza B virus, influenza C virus), Measles virus, Mumps virus, Rubella virus, Pneumovirus, Human respiratory syncytial virus, Rabies virus, California encephalitis virus, Japanese encephalitis virus, Hantaan virus, Lymphocytic choriomeningitis virus, Coronavirus, Enterovirus, Rhinovirus, Poliovirus, Norovirus, Flavivirus, Dengue virus, West Nile virus, Yellow fever virus and varicella.

In an embodiment, a composition of the invention may be used to treat and/or prevent an influenza virus infection in a subject in need thereof. Influenza is a single-stranded RNA virus of the family Orthomyxoviridae and is often characterized based on two large glycoproteins on the outside of the viral particle, hemagglutinin (HA) and neuraminidase (NA). Numerous HA subtypes of influenza A have been identified (Kawaoka et al., Virology (1990) 179:759-767; Webster et al., "Antigenic variation among type A influenza viruses," p. 127-168. In: P. Palese and D. W. Kingsbury (ed.), Genetics of influenza viruses. Springer-Verlag, New York).

Bacteria or parts of thereof useful as antigens in the invention include, without limitation, Anthrax (*Bacillus anthracis*), *Brucella, Bordetella pertussis, Candida, Chlamydia pneumoniae, Chlamydia psittaci,* Cholera, *Clostridium botulinum, Coccidioides immitis, Cryptococcus, Diphtheria, Escherichia coli* 0157: H7, Enterohemorrhagic *Escherichia coli*, Enterotoxigenic *Escherichia coli, Haemophilus influenzae, Helicobacter pylori, Legionella, Leptospira, Listeria, Meningococcus, Mycoplasma pneumoniae, Mycobacterium, Pertussis, Pneumonia, Salmonella, Shigella, Staphylococcus, Streptococcus pneumoniae* and *Yersinia enterocolitica*.

The antigen may alternatively be of protozoan origin, e.g. of the genus *Plasmodium* (*Plasmodium falciparum, Plasmodium malariae, Plasmodium vivax, Plasmodium ovale* or *Plasmodium knowlesi*), which causes malaria.

The antigen may alternatively be a naturally occurring or synthesized toxin, such as a drug substance (e.g. cocaine).

The term "polypeptide" encompasses any chain of amino acids, regardless of length (e.g., at least 6, 8, 10, 12, 14, 16, 18, or 20 amino acids) or post-translational modification (e.g., glycosylation or phosphorylation), and includes, for example, natural proteins, synthetic or recombinant polypeptides and peptides, epitopes, hybrid molecules, variants, homologs, analogs, peptoids, peptidomimetics, etc. A variant or derivative therefore includes deletions, including truncations and fragments; insertions and additions, for example conservative substitutions, site-directed mutants and allelic variants; and modifications, including peptoids having one or more non-amino acyl groups (for example, sugar, lipid, etc.) covalently linked to the peptide and post-translational modifications. As used herein, the term "conserved amino acid substitutions" or "conservative substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Polypeptides or peptides that have substantial identity to a preferred antigen sequence may be used. Two sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e., to have substantial identity) if they share at least 60%, 70%, 75%, 80%, 85%, 90%, 95%, 96%, 97%, 98%, 99% identity over a specified region. The term "identity" refers to sequence similarity between two polypeptides molecules. Identity can be determined by comparing each position in the aligned sequences. A degree of identity between amino acid sequences is a function of the number of identical or matching amino acids at positions shared by the sequences, for example, over a specified region. Optimal alignment of sequences for comparisons of identity may be conducted using a variety of algorithms, as are known in the art, including the ClustalW program, available at http://clustalw.genome.ad.ip, the local homology algorithm of Smith and Waterman, 1981, Adv. Appl. Math 2: 482, the homology alignment algorithm of Needleman and Wunsch, 1970, *J. Mol. Biol.* 48:443, the search for similarity method of Pearson and Lipman, 1988, Proc. Natl. Acad. Sci. USA 85:2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). For example, the "BLAST 2 Sequences" tool, available through the National Center for Biotechnology Information (through the internet at http://www.ncbi.nlm.nih.gov/BLAST/bl2seq/wblast2.cgi) may be used, selecting the "blastp" program at the following default settings: expect threshold 10; word size 3; matrix BLOSUM 62; gap costs existence 11, extension 1. In another embodiment, the person skilled in the art can readily and properly align any given sequence and deduce sequence identity and/or homology by mere visual inspection.

Polypeptides and peptides used to practice the invention can be isolated from natural sources, be synthetic, or be recombinantly generated polypeptides. Peptides and proteins can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g., Caruthers (1980) Nucleic Acids Res. Symp. Ser. 215-223; Hom (1980) Nucleic Acids Res. Symp. Ser. 225-232; Banga, A. K, Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

In some embodiments, the antigen may be a purified antigen, e.g., from about 25% to 50% pure, from about 50% to about 75% pure, from about 75% to about 85% pure, from about 85% to about 90% pure, from about 90% to about 95% pure, from about 95% to about 98% pure, from about 98% to about 99% pure, or greater than 99% pure.

As noted above, the term "antigen" also includes a polynucleotide that encodes the polypeptide that functions as an antigen. As used herein and in the claims, the term "polynucleotide" encompasses a chain of nucleotides of any length (e.g. 9, 12, 18, 24, 30, 60, 150, 300, 600, 1500 or more nucleotides) or number of strands (e.g. single-stranded or double-stranded). Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

The polynucleotide may be delivered in various forms. In some embodiments, a naked polynucleotide may be used, either in linear form, or inserted into a plasmid, such as an expression plasmid. In other embodiments, a live vector such as a viral or bacterial vector may be used.

One or more regulatory sequences that aid in transcription of DNA into RNA and/or translation of RNA into a polypeptide may be present. In some instances, such as in the case of a polynucleotide that is a messenger RNA (mRNA) molecule, regulatory sequences relating to the transcription process (e.g. a promoter) are not required, and protein expression may be effected in the absence of a promoter. The skilled artisan can include suitable regulatory sequences as the circumstances require.

In some embodiments, the polynucleotide is present in an expression cassette, in which it is operably linked to regulatory sequences that will permit the polynucleotide to be expressed in the subject to which the composition of the invention is administered. The choice of expression cassette depends on the subject to which the composition is administered as well as the features desired for the expressed polypeptide.

Typically, an expression cassette includes a promoter that is functional in the subject and can be constitutive or inducible; a ribosome binding site; a start codon (ATG) if necessary; the polynucleotide encoding the polypeptide of interest; a stop codon; and optionally a 3' terminal region (translation and/or transcription terminator). Additional sequences such as a region encoding a signal peptide may be included. The polynucleotide encoding the polypeptide of interest may be homologous or heterologous to any of the other regulatory sequences in the expression cassette. Sequences to be expressed together with the polypeptide of interest, such as a signal peptide encoding region, are typically located adjacent to the polynucleotide encoding the protein to be expressed and placed in proper reading frame. The open reading frame constituted by the polynucleotide encoding the protein to be expressed solely or together with any other sequence to be expressed (e.g. the signal peptide), is placed under the control of the promoter so that transcription and translation occur in the subject to which the composition is administered.

The amount of antigen used in a single treatment with a composition as described herein may vary depending on the type of antigen and the size of the subject. One skilled in the art will be able to determine, without undue experimentation, the effective amount of antigen to use in a particular application. The term "effective amount" as used herein means an amount effective, at dosages and for periods of time necessary, to achieve the desired result.

In another embodiment, the antigen may be or comprise a B cell epitope capable of inducing a humoral immune response. For example, the antigen may be or comprise a B cell epitope derived from a virus, such as for example influenza virus or respiratory syncytial virus.

In another embodiment, the B cell epitope may be an epitope derived from the hemagglutinin glycoprotein of the H5N1 influenza virus.

In another embodiment, the antigen may be or comprise a B cell epitope derived from a bacterium, such as for example *Bordetella pertussis* or *Bacillus anthracis*.

In another embodiment, the B cell epitope may be an epitope of the pertussis toxoid protein produced by *Bordetella pertussis*.

In another embodiment, the B cell epitope may be an epitope of the anthrax recombinant protective antigen.

In another embodiment, the antigen may be or comprise a B cell epitope associated with an infectious disease.

In another embodiment, the antigen may be or comprise a B cell epitope derived from a protozoan, such as from the genus *Plasmodium*.

In another embodiment, the antigen may be a cancer or tumor-associated protein, such as for example, a membrane surface-bound cancer antigen which is capable of being recognized by an antibody.

Cancers that may be treated and/or prevented by the use or administration of a composition of the invention include, without limitation, carcinoma, adenocarcinoma, lymphoma, leukemia, sarcoma, blastoma, myeloma, and germ cell tumors. In one embodiment, the cancer may be caused by a pathogen, such as a virus. Viruses linked to the development of cancer are known to the skilled person and include, but are not limited to, human papillomaviruses (HPV), John Cunningham virus (JCV), Human herpes virus 8, Epstein Barr Virus (EBV), Merkel cell polyomavirus, Hepatitis C Virus and Human T cell leukaemia virus-1. A composition of the invention may be used for either the treatment or prophylaxis of cancer, for example, in the reduction of the severity of cancer or the prevention of cancer recurrences. Cancers that may benefit from the compositions of the invention include any malignant cell that expresses one or more tumor specific antigens.

In another embodiment, the antigen may be a toxin or an allergen that is capable of being neutralized by an antibody. In an embodiment, the toxin is a drug substance such as, for example, cocaine.

In another embodiment, the antigen may be an antigen associated with a disease where it is desirable to sequester the antigen in circulation, such as for example an amyloid protein (e.g. Alzheimer's disease). Thus, a composition of the invention may be suitable for use in the treatment and/or prevention of a neurodegenerative disease in a subject in need thereof, wherein the neurodegenerative disease is associated with the expression of an antigen. The subject may have a neurodegenerative disease or may be at risk of developing a neurodegenerative disease. Neurodegenerative diseases that may be treated and/or prevented by the use or administration of a composition of the invention include, without limitation, Alzheimer's disease, Parkinson's disease, Huntington's disease, and amyotrophic lateral sclerosis (ALS). For example, Alzheimer's disease is characterized by the association of ß-amyloid plaques and/or tau proteins in the brains of patients with Alzheimer's disease (see, for example, Goedert and Spillantini, Science, 314: 777-781, 2006). Herpes simplex virus type 1 has also been proposed to play a causative role in people carrying the susceptible versions of the apoE gene (Itzhaki and Wozniak, J Alzheimers Dis 13: 393-405, 2008).

In a further embodiment, the composition may comprise a mixture of B cell epitopes as antigens for inducing a humoral immune response. The B cell epitopes may be linked to form a single polypeptide.

In another embodiment, the antigen may be any peptide or polypeptide that is capable of inducing a specific humoral immune response to a specific conformation on targeted tumor cells.

T Helper Epitopes

T helper epitopes are a sequence of amino acids (natural or non-natural amino acids) that have T helper activity. T helper epitopes are recognised by T helper lymphocytes, which play an important role in establishing and maximising the capabilities of the immune system, and are involved in activating and directing other immune cells, such as for example B cell antibody class switching.

A T helper epitope can consist of a continuous or discontinuous epitope. Hence not every amino acid of a T helper is necessarily part of the epitope. Accordingly, T helper epitopes, including analogs and segments of T helper epitopes, are capable of enhancing or stimulating an immune response. Immunodominant T helper epitopes are broadly reactive in animal and human populations with widely divergent MHC types (Celis et al. (1988) *J. Immunol.* 140:1808-1815; Demotz et al. (1989) *J. Immunol.* 142:394-402; Chong et al. (1992) *Infect. Immun.* 60:4640-4647). The T helper domain of the subject peptides has from about 10 to about 50 amino acids and preferably from about 10 to about 30 amino acids. When multiple T helper epitopes are present, then each T-helper epitope acts independently.

In one embodiment, the composition described herein may also comprise at least one T helper epitope. In some instances, the T-helper epitope may form part of the antigen. In particular, if the antigen is of sufficient size, it may contain an epitope that functions as a T-helper epitope. In other embodiments, the T-helper epitope is a separate molecule from the antigen.

In another embodiment, T helper epitope analogs may include substitutions, deletions and insertions of from one to about 10 amino acid residues in the T helper epitope. T helper segments are contiguous portions of a T helper epitope that are sufficient to enhance or stimulate an immune response. An example of T-helper segments is a series of overlapping peptides that are derived from a single longer peptide.

Sources of T helper epitopes for use in the present invention include, for example, hepatitis B surface antigen helper T cell epitopes, pertussis toxin helper T cell epitopes, measles virus F protein helper T cell epitope, *Chlamydia trachomitis* major outer membrane protein helper T cell epitope, diphtheria toxin helper T cell epitopes, *Plasmodium falciparum* circumsporozoite helper T cell epitopes, *Schistosoma mansoni* triose phosphate isomerase helper T cell epitopes, *Escherichia coli* TraT helper T cell epitopes and immune-enhancing analogs and segments of any of these T helper epitopes.

In one embodiment, the T helper epitope is a universal T helper epitope. A universal T helper epitope as used herein refers to a peptide or other immunogenic molecule, or a fragment thereof, that binds to a multiplicity of MHC class II molecules in a manner that activates T-cell function in a class II ($CD4^+$ T cells)-restricted manner.

In another embodiment, the T helper epitope may be a universal T helper epitope such as PADRE (pan-DR epitope) comprising the peptide sequence AKXVAAWTLKAAA (SEQ ID NO: 19), wherein X may be cyclohexylalanyl.

PADRE specifically has a CD4+T-helper epitope, that is, it stimulates induction of a PADRE-specific CD4+T helper response.

Tetanus toxoid has T helper epitopes that work in the similar manner as PADRE. Tetanus and diphtheria toxins have universal epitopes for human $CD4^+$ cells. (Diethelm-Okita, B. M. et al., Universal epitopes for human $CD4^+$ cells on tetanus and diphtheria toxins. *J. Infect. Diseases,* 181: 1001-1009, 2000). In another embodiment, the T helper epitope may be a tetanus toxoid peptide such as F21E comprising the peptide sequence FNNFTVSFWLRVPKVSASHLE (SEQ ID NO: 20) (amino acids 947-967).

In another embodiment, the T helper epitope is fused to at least one antigen (i.e., a peptide), or a mixture of antigens, to make a fusion peptide.

Carriers

The carrier of the composition comprises a continuous phase of a hydrophobic substance, preferably a liquid hydrophobic substance. The continuous phase may be an essentially pure hydrophobic substance or a mixture of hydrophobic substances. In addition, the carrier may be an emulsion of water in a hydrophobic substance or an emulsion of water in a mixture of hydrophobic substances, provided the hydrophobic substance constitutes the continuous phase. Further, in another embodiment, the carrier may function as an adjuvant.

Hydrophobic substances that are useful in the compositions as described herein are those that are pharmaceutically and/or immunologically acceptable. The carrier is preferably a liquid but certain hydrophobic substances that are not liquids at atmospheric temperature may be liquefied, for example by warming, and are also useful in this invention. In one embodiment, the hydrophobic carrier may be a Phosphate Buffered Saline/Freund's Incomplete Adjuvant (PBS/FIA) emulsion.

Oil or water-in-oil emulsions are particularly suitable carriers for use in the present invention. Oils should be pharmaceutically and/or immunologically acceptable. Suitable oils include, for example, mineral oils (especially light or low viscosity mineral oil such as Drakeol® 6VR), vegetable oils (e.g., soybean oil), nut oils (e.g., peanut oil), or mixtures thereof. In an embodiment, the oil is a mannide oleate in mineral oil solution, commercially available as Montanide® ISA 51. Animal fats and artificial hydrophobic polymeric materials, particularly those that are liquid at atmospheric temperature or that can be liquefied relatively easily, may also be used.

In embodiments herein where the composition is described as being a water-free liposome suspension ("water-free"), it is possible that the hydrophobic carrier of these "water-free" compositions may still contain small quantities of water, provided that the water is present in the non-continuous phase of the carrier. For example, individual components of the composition may have bound water that may not be completely removed by processes such as lyophilization or evaporation and certain hydrophobic carriers may contain small amounts of water dissolved therein. Generally, compositions of the invention that are described as "water-free" contain, for example, less than about 10%, 9%, 8%, 7%, 6%, 5%, 4%, 3%, 2%, 1%, 0.5%, 0.1%, 0.05%, or 0.01% water on a weight/weight basis of the total weight of the carrier component of the composition.

Liposomes

Liposomes are completely closed lipid bilayer membranes containing an entrapped aqueous volume. Liposomes may be unilamellar vesicles (possessing a single bilayer membrane) or multilamellar vesicles characterized by multimembrane bilayers, each bilayer may or may not be separated from the next by an aqueous layer. A general discussion of liposomes can be found in Gregoriadis G. *Immunol. Today,* 11:89-97, 1990; and Frezard, F., *Braz. J. Med. Bio. Res.,* 32:181-189, 1999. As used herein and in the claims, the term "liposomes" is intended to encompass all such vesicular structures as described above, including, without limitation, those described in the art as "niosomes", "transfersomes" and "virosomes".

Although any liposomes may be used in this invention, including liposomes made from archaebacterial lipids, particularly useful liposomes use phospholipids and unesterified cholesterol in the liposome formulation. The cholesterol is used to stabilize the liposomes and any other compound that stabilizes liposomes may replace the cholesterol. Other liposome stabilizing compounds are known to those skilled in the art. For example, saturated phospholipids produce liposomes with higher transition temperatures indicating increased stability.

Phospholipids that are preferably used in the preparation of liposomes are those with at least one head group selected from the group consisting of phosphoglycerol, phosphoethanolamine, phosphoserine, phosphocholine and phosphoinositol. More preferred are liposomes that comprise lipids which are 94-100% phosphatidylcholine. Such lipids are available commercially in the lecithin Phospholipon® 90 G. When unesterified cholesterol is also used in liposome formulation, the cholesterol is used in an amount equivalent to about 10% of the weight of phospholipid. If a compound other than cholesterol is used to stabilize the liposomes, one skilled in the art can readily determine the amount needed in the composition.

Liposome compositions may be obtained, for example, by using natural lipids, synthetic lipids, sphingolipids, ether lipids, sterols, cardiolipin, cationic lipids and lipids modified with poly (ethylene glycol) and other polymers. Synthetic lipids may include the following fatty acid constituents; lauroyl, myristoyl, palmitoyl, stearoyl, arachidoyl, oleoyl, linoleoyl, erucoyl, or combinations of these fatty acids.

Compositions

Further embodiments of the present invention include methods of making a composition of the invention comprising liposomes; an antigen capable of inducing a humoral immune response; a carrier comprising a continuous phase of a hydrophobic substance; and an adjuvant that activates or increases the activity of TLR2.

Methods for making liposomes are well known in the art. See e.g. Gregoriadis (1990) and Frezard (1999) both cited previously. Any suitable method for making liposomes may be used in the practice of the invention, or liposomes may be obtained from a commercial source. Liposomes are typically prepared by hydrating the liposome components that will form the lipid bilayer (e.g. phospholipids and cholesterol) with an aqueous solution, which may be pure water or a solution of one or more components dissolved in water, e.g. phosphate-buffered saline (PBS), phosphate-free saline, or any other physiologically compatible aqueous solution.

In an embodiment, a liposome component or mixture of liposome components, such as a phospholipid (e.g. Phospholipon® 90G) and cholesterol, may be solubilized in an organic solvent, such as a mixture of chloroform and methanol, followed by filtering (e.g. a PTFE 0.2 µm filter) and drying, e.g. by rotary evaporation, to remove the solvents.

Hydration of the resulting lipid mixture may be effected by e.g. injecting the lipid mixture into an aqueous solution or sonicating the lipid mixture and an aqueous solution. During formation of liposomes, the liposome components form single bilayers (unilamellar) or multiple bilayers (multilamellar) surrounding a volume of the aqueous solution with which the liposome components are hydrated.

In some embodiments, the liposomes are then dehydrated, such as by freeze-drying or lyophilization.

The liposomes are combined with the carrier comprising a continuous hydrophobic phase. This can be done in a variety of ways.

If the carrier is composed solely of a hydrophobic substance or a mixture of hydrophobic substances (e.g. use of a 100% mineral oil carrier), the liposomes may simply be mixed with the hydrophobic substance, or if there are multiple hydrophobic substances, mixed with any one or a combination of them.

If instead the carrier comprising a continuous phase of a hydrophobic substance contains a discontinuous aqueous phase, the carrier will typically take the form of an emulsion of the aqueous phase in the hydrophobic phase, such as a water-in-oil emulsion. Such compositions may contain an emulsifier to stabilize the emulsion and to promote an even distribution of the liposomes. In this regard, emulsifiers may be useful even if a water-free carrier is used, for the purpose of promoting an even distribution of the liposomes in the carrier. Typical emulsifiers include mannide oleate (Arlacel™ A), lecithin (e.g. S100 lecithin), a phospholipid, Tween™ 80, and Spans™ 20, 80, 83 and 85. Typically, the volume ratio (v/v) of hydrophobic substance to emulsifier is in the range of about 5:1 to about 15:1 with a ratio of about 10:1 being preferred.

The liposomes may be added to the finished emulsion, or they may be present in either the aqueous phase or the hydrophobic phase prior to emulsification.

The antigen may be introduced at various different stages of the formulation process. More than one type of antigen may be incorporated into the composition (e.g. an inactivated virus, attenuated live virus, protein or polypeptide).

In some embodiments, the antigen is present in the aqueous solution used to hydrate the components that are used to form the lipid bilayers of the liposomes (e.g. phospholipid(s) and cholesterol). In this case, the antigen will be encapsulated in the liposome, present in its aqueous interior. If the resulting liposomes are not washed or dried, such that there is residual aqueous solution present that is ultimately mixed with the carrier comprising a continuous phase of a hydrophobic substance, it is possible that additional antigen may be present outside the liposomes in the final product. In a related technique, the antigen may be mixed with the components used to form the lipid bilayers of the liposomes, prior to hydration with the aqueous solution. The antigen may also be added to pre-formed liposomes, in which case the antigen may be actively loaded into the liposomes, or bound to the surface of the liposomes or the antigen may remain external to the liposomes. In such embodiments, prior to the addition of antigen, the pre-formed liposomes may be empty liposomes (e.g. not containing encapsulated antigen or lipid-based adjuvant) or the pre-formed liposomes may contain lipid-based adjuvant incorporated into or associated with the liposomes. These steps may preferably occur prior to mixing with the carrier comprising a continuous phase of a hydrophobic substance.

In an alternative approach, the antigen may instead be mixed with the carrier comprising a continuous phase of a hydrophobic substance, before, during, or after the carrier is combined with the liposomes. If the carrier is an emulsion, the antigen may be mixed with either or both of the aqueous phase or hydrophobic phase prior to emulsification. Alternatively, the antigen may be mixed with the carrier after emulsification.

The technique of combining the antigen with the carrier may be used together with encapsulation of the antigen in the liposomes as described above, such that antigen is present both within the liposomes and in the carrier comprising a continuous phase of a hydrophobic substance.

The above-described procedures for introducing the antigen into the composition apply also to the djuvant of the compositions of the present invention. That is, the adjuvant may be introduced into e.g. any one or more of: (1) the aqueous solution used to hydrate the components that are used to form the lipid bilayers of the liposomes; (2) the aqueous solution after formation of the lipid bilayers of the liposomes; (3) the components used to form the lipid bilayers of the liposomes; or (4) the carrier comprising a continuous phase of a hydrophobic substance, before, during, or after the carrier is combined with the liposomes. If the carrier is an emulsion, the adjuvant may be mixed with either or both of the aqueous phase or hydrophobic phase before, during or after emulsification.

The technique of combining the adjuvant with the carrier may be used together with encapsulation of the adjuvant in the liposomes, or with addition of the adjuvant to the liposomes, such that adjuvant is present inside and/or outside the liposomes and in the carrier comprising a continuous phase of a hydrophobic substance.

The adjuvant can be incorporated in the composition together with the antigen at the same processing step, or separately, at a different processing step. For instance, the antigen and the adjuvant may both be present in the aqueous solution used to hydrate the lipid bilayer-forming liposome components, such that both the antigen and adjuvant become encapsulated in the liposomes. Alternatively, the antigen may be encapsulated in the liposomes, and the adjuvant mixed with the carrier comprising a continuous phase of a hydrophobic substance. In a further embodiment, the adjuvant may be incorporated into the composition after the antigen encapsulation step by passing the liposome-antigen preparation through a manual mini-extruder and then mixing the obtained liposome-antigen preparation with the lipid-based adjuvant in, for example, phosphate buffer. The adjuvant may also be incorporated into the composition, either alone or together with antigen, after the liposomes have been formed, such that the adjuvant may be associated or remain external to the liposomes. The adjuvant may also be incorporated into or associated with liposomes prior to addition of antigen, with the antigen remaining outside the pre-formed liposomes or loaded into/associated with the liposomes by further processing. In such embodiments, the resulting liposome-antigen-adjuvant preparation may by lyophilized and then reconstituted in the carrier comprising a continuous phase of a hydrophobic substance. It will be appreciated that many such combinations are possible.

If the composition contains one or more further adjuvants, such additional adjuvants can be incorporated in the composition in similar fashion as described above for the adjuvant or by combining several of such methods as may be suitable for the additional adjuvant(s).

Stabilizers such as sugars, anti-oxidants, or preservatives that maintain the biological activity or improve chemical stability to prolong the shelf life of antigen, adjuvant, the liposomes or the continuous hydrophobic carrier, may be added to such compositions.

In some embodiments, an antigen/adjuvant mixture may be used, in which case the antigen and adjuvant are incorporated into the composition at the same time. An "antigen/adjuvant mixture" refers to an embodiment in which the antigen and adjuvant are in the same diluent at least prior to incorporation into the composition. The antigen and adjuvant in an antigen/adjuvant mixture may, but need not necessarily be chemically linked, such as by covalent bonding.

In some embodiments, the carrier comprising a continuous phase of a hydrophobic substance may itself have adjuvanting-activity. Incomplete Freund's adjuvant, is an example of a hydrophobic carrier with adjuvanting effect. As used herein and in the claims, when the term "adjuvant" is used, this is intended to indicate the presence of an adjuvant in addition to any adjuvanting activity provided by the carrier comprising a continuous phase of a hydrophobic substance.

In an embodiment, to formulate a composition of the invention, a homogenous mixture of S100 lecithin and cholesterol (e.g. 10:1 w:w) are hydrated in the presence of an antigen, optionally in phosphate buffer, to form liposomes with encapsulated antigen. The liposome preparation may then be extruded, optionally through a manual mini-extruder, and mixed with the adjuvant, optionally in phosphate buffer, to incorporate the adjuvant. This suspension may then be lyophilized and reconstituted in a carrier comprising a continuous phase of a hydrophobic substance to form a water-free liposome suspension.

In some embodiments, the composition may be formulated by hydrating a homogenous mixture of S100 lecithin and cholesterol (e.g. 10:1 w:w) in the presence of an antigen and a suitable adjuvant (e.g. Pam-3-Cys), optionally in phosphate buffer, to form liposomes with encapsulated antigen and adjuvant. The liposome/antigen/adjuvant preparation may then be diluted to sufficient quantity, optionally using water, and lyophilized. The lyophilized liposomes may then be reconstituted in a carrier comprising a continuous phase of a hydrophobic substance (e.g. mineral oil or Montanide® ISA 51) to form a water-free liposome suspension.

In some embodiments, the composition may be formulated by hydrating a homogenous mixture of dioleoyl-phosphatidylcholine (DOPC) and cholesterol (e.g. 10:1 w:w) in the presence of an antigen and a suitable adjuvant (e.g. Pam-3-Cys-Ser-(Lys)4; SEQ ID NO: 1), optionally in phosphate buffer, to form liposomes encapsulated with antigen and adjuvant. The liposome/antigen/adjuvant preparation may then be lyophilized and the resultant product reconstituted in a carrier comprising a continuous phase of a hydrophobic substance (e.g. mineral oil or Montanide® ISA 51) to form a water-free liposome suspension.

Alternatively, the antigen or antigen/adjuvant complex may be associated with, in contact with or separate from liposomes and not encapsulated in liposomes. The efficiency of liposome encapsulation of some hydrophilic antigens or hydrophilic antigen/adjuvant complexes may be poor so that upon being placed in a hydrophobic environment or freeze-drying most of the antigen becomes associated with the external surface of the liposomes. This represents another embodiment of the invention.

In a further embodiment, an antigen (peptide or polypeptide) having a B cell epitope and PADRE (fused to the antigen or separate) may be encapsulated together in liposomes. In another embodiment, more than one antigen may be placed together in the same liposomes. In a further embodiment, other substances may be used instead of PADRE that have a T-helper epitope, for example, tetanus toxoid peptide(s). In another embodiment, a adjuvant, preferably a palmitic acid based adjuvant which comprises $PAM_2Cys$ or $PAM_3Cys$, may be encapsulated in the liposomes as well. The liposomes are preferably suspended in PBS. This suspension is then emulsified in a hydrophobic carrier, such as for example, ISA51 or mineral oil. The result is that liposomes containing the antigen(s) and adjuvant(s) are suspended in PBS which in turn is emulsified in a hydrophobic carrier, for example, ISA51 or mineral oil.

In one embodiment, antibody titers obtained from mice injected intramuscularly with a single dose of a composition of the invention comprising liposomes/H5N1 recombinant hemagglutinin protein (antigen)/Pam-3-Cys-Ser-(Lys)4 (SEQ ID NO: 1) (adjuvant)/hydrophobic carrier (Vaccine A) were significantly enhanced at three, four and eight weeks post-immunization compared to mice treated (and boosted) with an aqueous aluminum based control vaccine (FIG. 1). For example, Vaccine A of the invention was capable of generating endpoint antibody titers at three and four weeks post-vaccination of up to 1/2,048,000 and up to 1/8,192,000 at eight weeks post-vaccination, whereas endpoint antibody titers for control vaccine were only up to 1/512,000, 1/256,000 and 1/4,096,000 at three, four and eight weeks post-vaccination, respectively. These results indicate that compositions of the invention are capable of generating, upon single dose, an enhanced in vivo humoral immune response compared to single or boosted aqueous alum based control vaccine.

Figure 2:
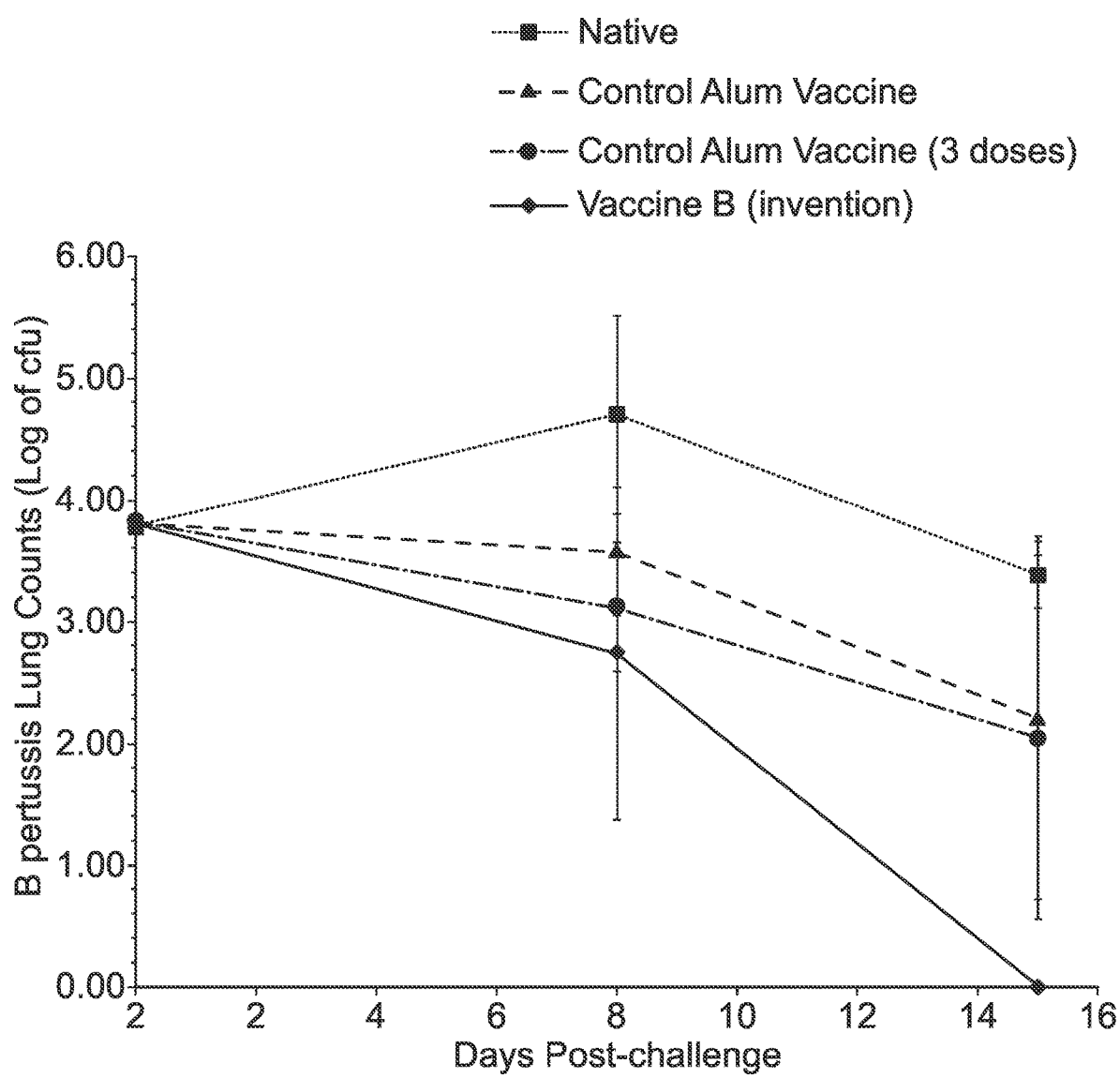
FIG. 2 illustrates the effect of a single administration of a vaccine made in accordance with the invention ("Vaccine B"). Three groups of mice (n=9 or 11) were vaccinated as follows: Group 1 mice were vaccinated with a single dose of 1 microgram PT and 1 microgram Pam-3-Cys-Ser-(Lys)4 (SEQ ID NO: 1) in a 50 microliter dose formulated as a water-free/liposome/P3C/hydrophobic carrier vaccine (Vaccine B). Group 2 and group 3 mice were treated with 1 microgram PT and 100 micrograms alum per 100 microliter dose of control alum vaccine; group 2 mice received a single dose, group 3 mice were boosted at days 21 and 31. Group 4 mice remained un-vaccinated. Mice were challenged 56 days post-vaccination with aerosol inoculation with *Bordetella pertussis* and bacterial lung counts established 8 and 15 days post-challenge. For each treatment group, the log 10 values of the colony forming units per lung were averaged and standard deviations calculated for each time point.

In one embodiment, immunization of mice by single treatment with a composition of the invention comprising liposomes/pertussis toxoid protein (antigen)/Pam-3-Cys-Ser-(Lys)4 (SEQ ID NO: 1) (adjuvant)/hydrophobic carrier (Vaccine B) was able to reduce bacterial lung counts from as high as $6.2 \times 10^4$ cfu per lung at day 8 post-challenge with Bordetella pertussis to 0 cfu per lung at day 15 post-challenge (FIG. 2). These results indicate that a single dose of a composition of the invention effectively protects mice from bacterial challenge and allows them to completely clear the infection from the lungs.

Figure 3:
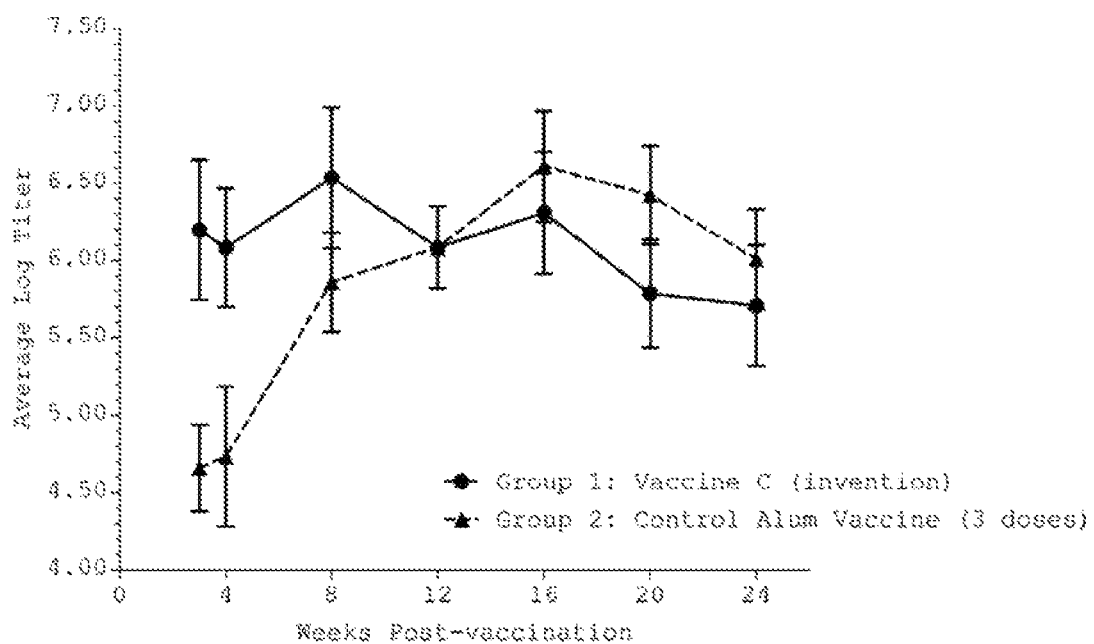
FIG. 3 illustrates the effect of a single administration of a vaccine made in accordance with the invention ("Vaccine C"). Two groups of rabbits (N=8) were vaccinated as follows: Group 1 rabbits were vaccinated with a single dose of 8 micrograms rPA and 2 micrograms Pam-3-Cys in a 100 microliter dose formulated as a liposome/P3C/hydrophobic carrier vaccine (Vaccine C). Group 2 rabbits were treated with 8 micrograms rPA and 350 micrograms aluminum hydroxide per 100 microliter dose of control alum vaccine; rabbits were boosted at 28 and 84 days post-vaccination. Humoral immune responses were measured by ELISA as described above. For each treatment group, the log 10 values of the endpoint antibody titers were averaged and standard deviations calculated for each time point.

In one embodiment, antibody titers obtained from rabbits injected intramuscularly with a single dose of a composition of the invention comprising liposomes/anthrax recombinant protective antigen (antigen)/Pam-3-Cys (adjuvant)/hydrophobic carrier (Vaccine C) were significantly enhanced compared to rabbits treated with an aqueous aluminum based control vaccine at the early (pre-boost) time points (FIG. 3). For example, Vaccine C of the invention was capable of generating endpoint antibody titers at three and four weeks post-vaccination of up to 1/2,048,000 and up to 1/8,192,000 at eight weeks post-vaccination, whereas endpoint antibody titers for control vaccine were only up to 1/64,000, 1/256,000 and 1/2,048,000 at three, four and eight weeks post-vaccination, respectively. These results indicate that compositions of the invention are capable of generating a surprisingly strong in vivo humoral immune response as early as three weeks following a single vaccination.

Figure 4:
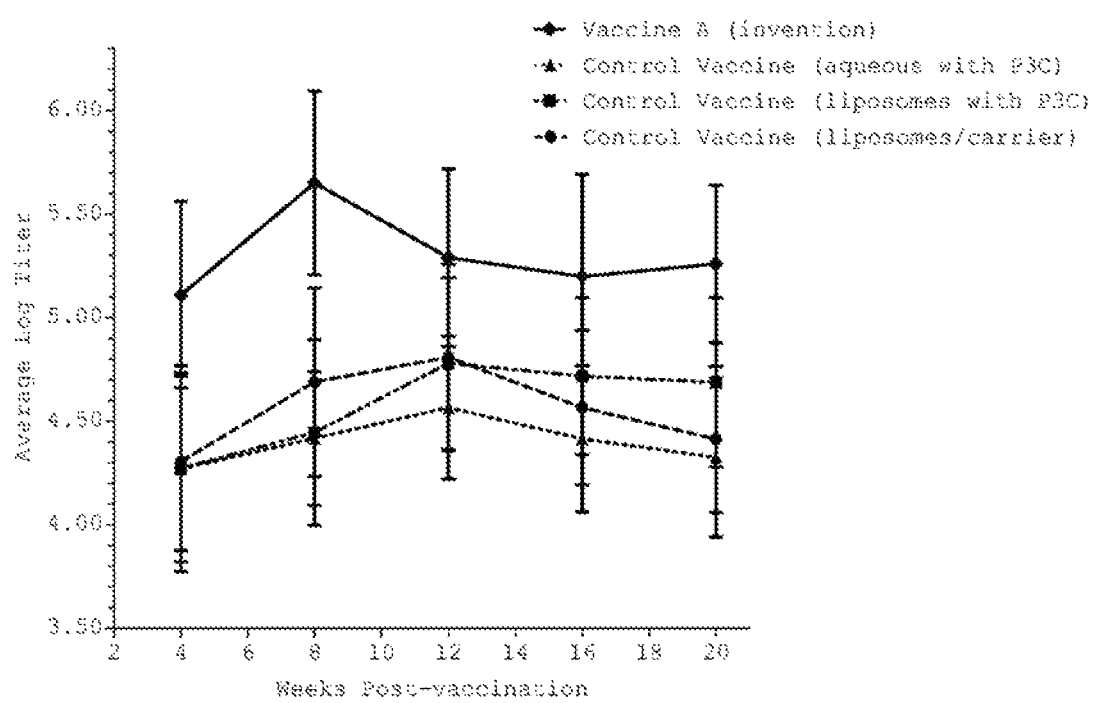
FIG. 4 illustrates that Vaccine A of the invention, specifically comprising an antigen, liposomes, a palmitic acid adjuvant and a hydrophobic carrier, is capable of simulating maximal immunogenicity. Four groups of mice (N=10) were vaccinated as follows: Group 1 mice were vaccinated with a single dose of 1 microgram rHA and 1 microgram Pam-3-Cys in a 50 microliter dose formulated as a liposome/P3C/hydrophobic carrier vaccine (Vaccine A, the invention). Group 2 mice were treated with 1 microgram of rHA and 1 microgram of P3C per 50 microliter dose. Group 3 mice were treated with 1 microgram rHA and 1 microgram of P3C per 50 microliter dose formulated as an aqueous/liposome/P3C vaccine. Group 4 mice were treated with 1 microgram of rHA formulated as a liposome/hydrophobic carrier vaccine. Humoral responses were measured by ELISA as described above. For each treatment group, the log 10 values of the endpoint antibody titers were averaged and standard deviations calculated for each time point.

In one embodiment, antibody titres obtained from mice injected intramuscularly with a single dose of Vaccine A of the invention (Group 1) were significantly enhanced compared to single dose administration of control compositions without liposomes (Group 2), without hydrophobic carrier (Group 3) or without lipid-based adjuvant (Group 4) (FIG. 4). For example, Vaccine C of the invention was capable of generating endpoint antibody titers at eight weeks post-vaccination of up to 1/2,048,000, while Groups 2, 3 and 4 were only able to generate endpoint antibody titers at the same time point of 1/64,000, 1/128,000 and 1/128,000, respectively. These results show the that compositions of the invention comprising each of: an antigen, liposomes, a lipid-based adjuvant and a carrier comprising a continuous phase of a hydrophobic substance, are capable of raising robust and long lasting in vivo humoral immune responses.

The compositions as described herein may be formulated in a form that is suitable for oral, nasal, rectal or parenteral administration. Parenteral administration includes intravenous, intraperitoneal, intradermal, subcutaneous, intramuscular, transepithelial, intrapulmonary, intrathecal, and topical modes of administration. The preferred routes are intramuscular, subcutaneous and intradermal to achieve a depot effect.

The skilled artisan can determine suitable treatment regimes, routes of administration, dosages, etc., for any particular application in order to achieve the desired result. Factors that may be taken into account include, e.g.: the nature of the antigen; the disease state to be prevented or treated; the age, physical condition, body weight, sex and diet of the subject; and other clinical factors. See, for example, "Vaccine Handbook", edited by the Researcher's Associates (Gaku-yuu-kai) of The National Institute of Health (1994); "Manual of Prophylactic Inoculation, 8th edition", edited by Mikio Kimura, Munehiro Hirayama, and Harumi Sakai, Kindai Shuppan (2000); "Minimum Requirements for Biological Products", edited by the Association of Biologicals Manufacturers of Japan (1993).

The optimal amount of adjuvant and antigen to elicit an optimal immune response may depend on a number of factors including, without limitation, the composition, the disease, the subject, and may be readily ascertained by the skilled person using standard studies including, for example, observations of antibody titers and other immunogenic responses in the host.

The compositions as described herein may be effective when administered in a single application.

In another embodiment, the compositions as described herein may be used in combination, before or after, with other therapies.

Kits and Reagents

The present invention is optionally provided to a user as a kit. For example, a kit of the invention contains one or more of the compositions of the invention. The kit can further comprise one or more additional reagents, packaging material, containers for holding the components of the kit, and an instruction set or user manual detailing preferred methods of using the kit components.

Embodiments of the Invention

Particular embodiments of the invention include, without limitation, the following:

1. A composition comprising, consisting of, or consisting essentially of: liposomes; an antigen capable of inducing a humoral immune response; a carrier comprising a continuous phase of a hydrophobic substance; and an adjuvant that activates or increases the activity of TLR2, preferably a lipid-based adjuvant.

2. The composition of paragraph 1, wherein the adjuvant activates or increases the activity of toll-like receptor 2 (TLR2), or a TLR2 dimer such as TLR1/2 or TLR2/6.

3. The composition of paragraph 1, wherein the adjuvant only activates or increases the activity of a toll-like receptor (TLR) selected from TLR2, heterodimeric TLR1/2 and heterodimeric TLR2/6, but does not activate or increase the activity of other TLRs.

4. The composition of any one of paragraphs 1 to 3, wherein theadjuvant is a compound comprising, consisting of, or consisting essentially of at least one natural, synthetic or semi-synthetic lipid moiety, lipid component, or analog or derivative thereof, including for example a lipoamino acid, a lipoglycan, a lipopolysaccharide, a lipoteichoic acid or a cell-wall component of a Gram-positive or Gram-negative bacteria, Rhodopseudomonas viridis or mycoplasma.

5. The composition of any one of paragraphs 1 to 4, wherein theadjuvant comprises, consists of, or consists essentially of PAM$_2$Cys-Ser-(Lys)4 (SEQ ID NO: 1), PAM$_3$Cys-Ser-(Lys)4 (SEQ ID NO: 1), PAM$_3$Cys-SKKKK (SEQ ID NO: 1)((3-irradiated), R-PAM$_3$Cys-SKKKK (SEQ ID NO: 1), S-PAM$_3$Cys-SKKKK (SEQ ID NO: 1), PAM$_3$Cys-SKKKK(Biotin-Aca-Aca) (SEQ ID NO: 1), PAM$_3$Cys-SKKKK(Fluorescein-Aca-Aca) (SEQ ID NO: 1), PAM$_3$Cys-SKKKK (Rhodamine-Aca-Aca) (SEQ ID NO: 1), PAM$_3$Cys-SKKKK-FLAG-tag (SEQ ID NO: 1), PHC-SKKKK (SEQ ID NO: 3), PHC-SKKKK(Biotin-Aca-Aca) (SEQ ID NO: 3), PAM$_3$Cys-SSNAKIDQLSSDVQT (SEQ ID NO: 4), PAM$_3$Cys-SSNKSTTGSGETTTA (SEQ ID NO: 5), PAM$_3$Cys-SSTKPVSQDTSPKPA (SEQ ID NO: 6), PAM$_3$Cys-SSGSKPSGGPLPDAK (SEQ ID NO: 7), PAM$_3$Cys-SSGNKSAPSSSASSS (SEQ ID NO: 8), PAM$_3$Cys-GSHQMKSEGHANMQL (SEQ ID NO: 9), PAM$_3$Cys-SSSNNDAAGNGAAQT (SEQ ID NO: 10), PAM$_3$Cys-KQNVSSLDEKNSVSV (SEQ ID NO: 11), PAM$_3$Cys-NNSGKDGNTSANSAD (SEQ ID NO: 12), PAM$_3$Cys-NNGGPELKSDEVAKS (SEQ ID NO: 13), PAM$_3$Cys-SQEPAAPAAEATPAG (SEQ ID NO: 14), PAM$_3$Cys-SSSKSSDSSAPKAYG (SEQ ID NO: 15), PAM$_3$Cys-AQEKEAKSELDYDQT (SEQ ID NO: 16), PAM$_2$Cys-SKKKK (mixture of RR and RS stereoisomers), (SEQ ID NO: 1) R-PAM$_2$Cys-SKKKK (RR stereoisomer) (SEQ ID NO: 1), S-PAM$_2$Cys-SKKKK (RS stereoisomer) (SEQ ID NO: 1), PAMCys(PAM)-SKKKK, PAM$_2$Cys-SKKKK(Biotin-Aca-Aca)-NH$_2$ (SEQ ID NO: 1), PAM$_2$Cys-SKKKK (Fluorescein-Aca-Aca)-NH$_2$ (SEQ ID NO: 1), PAM$_2$Cys-SKKKK(Rhodamine-Aca-Aca)-NH$_2$ (SEQ ID NO: 1), PAM$_2$Cys-SKKKK-FLAG-tag (SEQ ID NO: 1), PAM-Dhc-SKKKK (SEQ ID NO: 3), PAM-CSKKKK (SEQ ID NO: 1), PAM-Dhc-GDPKHPKSF (SEQ ID NO: 17), PAM-CGDPKHPKSF (SEQ ID NO: 2), FSL-1 (Pam2CGDPKHPKSF; SEQ ID NO: 2), FSL-1-Ala, macrophage activating lipopeptide-2 (MALP-2), lipoarabinomannan from M. smegmatis (LAM-MS), lipomannan from M. smegmatis (LM-MS), lipopolysaccharide from P. gingivalis (LPS-PG Ultrapure), lipoteichoic acid from B. subtilis (LTA-BS) or S. aureus (LTA-SA), or derivatives or analogs thereof, or is a heat-killed bacteria that comprises the cell-wall component of a Gram-positive or Gram-negative bacteria.

6. The composition of any one of paragraphs 1 to 5, wherein theadjuvant is a palmitic acid adjuvant.

7. The composition of any one of paragraphs 1 to 6, wherein the adjuvant comprises, consists of, or consists essentially of dipalmitoyl-S-glyceryl-cysteine (PAM$_2$Cys) or tripalmitoyl-S-glyceryl-cysteine (PAM$_3$Cys).

8. The composition of any one of paragraphs 1 to 6, wherein the adjuvant is PAM$_2$Cys-Ser-(Lys)4 (SEQ ID NO: 1), PAM$_3$Cys-Ser-(Lys)4 (SEQ ID NO: 1), FSL-1 or MALP-2.

9. The composition of paragraph 8, wherein the adjuvant is PAM$_2$Cys-Ser-(Lys)4 (SEQ ID NO: 1).

10. The composition of paragraph 8, wherein theadjuvant is PAM$_3$Cys-Ser-(Lys)4 (SEQ ID NO: 1).

11. The composition of any one of paragraphs 1 to 10 which further comprises at least one other suitable adjuvant in addition to the adjuvant that activates or increases the activity of TLR2.

12. The composition of any one of paragraphs 1 to 11, wherein the antigen is a polypeptide or a carbohydrate.

13. The composition of any one of paragraphs 1 to 12, wherein the antigen comprises, consists of, or consists essentially of a B cell epitope, or a plurality of B cell epitopes.

14. The composition of paragraph 13, wherein the B cell epitope is derived from a virus or bacteria.

15. The composition of paragraph 14, wherein the B cell epitope is derived from influenza virus, Bordetella pertussis or Bacillus anthracis.

16. The composition of paragraph 15, wherein the B cell epitope is an epitope of a hemagglutinin protein of H5N1 influenza virus, an epitope of pertussis toxoid protein, or an epitope of an anthrax recombinant protective antigen.

17. The composition of any one of paragraphs 1 to 13, wherein the antigen is: an antigen associated with an infectious disease; a membrane surface-bound cancer antigen; a toxin; an allergen such as pollen; or an antigen associated with a disease where it is desirable to sequester the antigen in circulation, such as for example an amyloid protein.

18. The composition of paragraph 17, wherein the infectious disease is influenza, a respiratory tract infection caused by human respiratory syncytial virus, pertussis, anthrax or malaria.

19. The composition of paragraph 17, wherein the toxin is a drug substance, such as cocaine.

20. The composition of any one of paragraphs 1 to 13, wherein the antigen is a hapten-carrier adduct.

21. The composition of any one of paragraphs 1 to 20, wherein the liposome comprises, consists of, or consists essentially of a phospholipid or unesterified cholesterol.

22. The composition of any one of paragraphs 1 to 21, wherein the antigen is encapsulated in the liposomes or both the antigen and the adjuvant are encapsulated in the liposomes.

23. The composition of any one of paragraphs 1 to 22, which is a water-free liposome suspension.

24. The composition of any one of paragraphs 1 to 23, wherein the composition is capable of inducing a humoral immune response with a single dose.

25. The composition of paragraph 24, wherein the humoral immune response is characterized by antigen-specific antibody production.

26. The composition of paragraph 25 which is capable of generating the antigen-specific antibody at an antibody titer of up to about 1/2,048,000 by about three weeks post-vaccination of a subject.

27. The composition of paragraph 25 which is capable of generating the antigen-specific antibody at an antibody titer of up to about 1/8,192,000 by about eight weeks post-vaccination of a subject.

28. The composition of any one of paragraphs 24 to 27, wherein the humoral immune response is associated with the activation or generation of T-helper 2 (Th2) cells or T-helper 17 (Th17) cells.

29. The composition of any one of paragraphs 1 to 28 for the treatment or prevention of a disease or disorder ameliorated by a humoral immune response.

30. The composition of any one of paragraphs 1 to 28 for the treatment or prevention of: an infectious disease; a cancer involving a membrane surface-bound cancer antigen; or a disease or disorder where it is desirable to sequester antigen in circulation, such as Alzheimer's disease.

31. The composition of any one of paragraphs 1 to 28 for neutralizing a toxin, virus, bacterium or allergen, with an antibody.

32. A method for treating or preventing a disease or disorder ameliorated by a humoral immune response, said method comprising, consisting of, or consisting essentially of administering the composition of any one of paragraphs 1 to 28 to a subject.

33. A method for treating or preventing an infectious disease; a cancer involving a membrane surface-bound cancer antigen; or a disease or disorder where it is desirable to sequester antigen in circulation, such as Alzheimer's disease, said method comprising, consisting of, or consisting essentially of administering the composition of any one of paragraphs 1 to 28 to a subject.

34. The method of paragraph 33, wherein the infectious disease is influenza, a respiratory tract infection caused by human respiratory syncytial virus, pertussis, anthrax or malaria.

35. A method for neutralizing a toxin, virus, bacterium or allergen, with an antibody, said method comprising, consisting of, or consisting essentially of administering the composition of any one of paragraphs 1 to 28 to a subject.

36. The method of paragraph 35, wherein the toxin is a drug substance, such as cocaine.

37. The method of any one of paragraphs 32 to 36, wherein the subject is a mammal, preferably a human.

38. A kit useful for treating or preventing a disease or disorder ameliorated by a humoral immune response; or useful for treating or preventing an infectious disease; a cancer involving a membrane surface-bound cancer antigen; or a disease or disorder where it is desirable to sequester antigen in circulation, such as Alzheimer's disease; or useful for neutralizing a toxin, virus, bacterium or allergen, with an antibody, wherein the kit comprises, consists of, or consists essentially of the composition of any one of paragraphs 1 to 28, and instructions for its use thereof.

39. A method of preparing the composition of paragraph 1, comprising, consisting of, or consisting essentially of: hydrating a homogenous mixture of S100 lecithin and cholesterol in the presence of the antigen to form a liposome preparation with encapsulated antigen; extruding and then mixing the liposome preparation with the adjuvant; lyophilizing and reconstituting the resultant product in a carrier comprising a continuous phase of a hydrophobic substance. In an alternate embodiment, the hydrating step may be performed in the presence of a homogenous mixture of dioleoyl-phosphatidylcholine (DOPC) and cholesterol.

40. A method of preparing the composition of paragraph 1, comprising, consisting of, or consisting essentially of: hydrating a homogenous mixture of dioleoyl-phosphatidylcholine (DOPC) and cholesterol in the presence of the antigen and the adjuvant to form a liposome preparation with encapsulated antigen and adjuvant; lyophilizing and reconstituting the liposome preparation in a carrier comprising a continuous phase of a hydrophobic substance. In an alternate embodiment, the hydrating step may be performed in the presence of a homogenous mixture of S100 lecithin and cholesterol.

The invention is further illustrated by the following non-limiting examples.

EXAMPLES

Example 1

Pathogen free, female CD1 mice, 6-8 weeks of age, were obtained from Charles River Laboratories (St Constant, QC, Canada) and were housed according to institutional guidelines with water and food ad libitum, under filter controlled air circulation.

The H5N1 recombinant hemagglutinin protein, was purchased from Protein Sciences (Meridien, Conn., USA). This recombinant protein has an approximate molecular weight of 72,000 daltons and corresponds to the hemagglutinin glycoprotein, an antigenic protein present on the surface of the H5N1 influenza virus. This recombinant protein, hereafter designated rHA, was used as a model antigen to test the efficacy of vaccine formulations. rHA was used at 1 microgram per 50 microliter dose.

Vaccine efficacy was assessed by enzyme-linked immunosorbent assay (ELISA), a method that allows the detection of antigen-specific antibody levels in the serum of immunized animals. Performing the ELISA on sera collected from immunized mice on a regular interval (every four weeks for example), is useful for monitoring the antibody responses to a given vaccine formulation. Briefly, a 96-well microtiter plate is coated with antigen (rHA, 1 microgram/milliliter) overnight at 4 degrees Celsius, blocked with 3% gelatin for 30 minutes, then incubated overnight at 4 degrees Celsius with serial dilutions of sera, typically starting at a dilution of 1/2000. A secondary reagent (protein G conjugated to alkaline phosphatase, EMD chemicals, Gibbstown, N.J., USA) is then added to each well at a 1/500 dilution for one hour at 37 degrees Celsius. Following a 60 minute incubation with a solution containing 1 milligram/milliliter 4-nitrophenyl phosphate disodium salt hexahydrate (Sigma-Aldrich Chemie GmbH, Switzerland), the 405 nanometer absorbance of each well is measured using a microtiter plate reader (ASYS Hitech GmbH, Austria). Endpoint titers are calculated as described in Frey A. et al. (Journal of Immunological Methods, 1998, 221:35-41). Calculated titers represent the highest dilution at which a statistically significant increase in absorbance is observed in serum samples from immunized mice versus serum samples from naïve, non-immunized control mice. Titers are presented as log 10 values of the endpoint dilution.

To formulate vaccine corresponding to the invention, a 10:1 w:w homogenous mixture of S100 lecithin and cholesterol (Lipoid GmbH, Germany) was hydrated in the presence of rHA in phosphate buffer to form liposomes with encapsulated rHA. In brief, 20 micrograms of rHA in 775 microliters of 50 millimolar phosphate buffer (pH 7.4) was added to 132 milligrams of the S100 lecithin/cholesterol mixture to form approximately 900 microliters of a liposome suspension encapsulating the rHA antigen. The liposome preparation was then extruded by passing the material through a manual mini-extruder (Avanti, Alabaster, Ala., USA) fitted with a 200 nanometer polycarbonate membrane. To incorporate the adjuvant, the sized liposome mixture was thoroughly mixed with 20 micrograms of Pam-3-Cys-Ser-(Lys)4 (SEQ ID NO: 1) (designated P3C) adjuvant (EMC Microcollections GmbH, Germany) in 100 microliters of phosphate buffer. After diluting the final mixture in half using water, the liposome suspension was lyophilized using the Virtis Advantage freeze dryer (SP Industries, Warm inister, PA, USA). For every 1 milliliter of original liposome suspension containing rHA and P3C, 800 microliters of a mineral oil carrier equivalent to Freund's incomplete adjuvant (known as Montanide® ISA 51, supplied by Seppic, France) was used to reconstitute the lyophilized liposomes to form a water-free liposome suspension. Each vaccine dose consisted of 50 microliters of the above described formulation containing liposomes, rHA antigen, P3C adjuvant, and the mineral oil carrier. This vaccine formulation will be referred to as water-free/liposome/P3C/hydrophobic carrier.

The efficacy of the water-free liposome formulation described above was compared to the efficacy of a control vaccine consisting of 1 microgram of rHA and 50 micrograms of aluminum hydroxide (alhydrogel, Sigma, Mississauga, ON, Canada, hereafter named alum) in 50 microliters of 50 millimolar phosphate buffer (pH 7.4). One group of mice (N=9) were injected once (no boosting) with 1 microgram of rHA antigen and 1 microgram of P3C adjuvant formulated in 50 microliters of water-free/liposome/P3C/hydrophobic carrier as described above. Group 2 mice (N=8) were vaccinated twice (day 0 and day 28) with 1 microgram of rHA and 50 micrograms of alum adjuvant suspended in 50 millimolar phosphate buffer. All mice were vaccinated intramuscularly in the flank region and serum samples were collected at 3, 4, and 8 weeks post-immunization. rHA antibody titers in these sera were examined by ELISA as described above.

The results of this experiment are shown in FIG. 1. Group 2 mice generated a detectable antigen-specific antibody response following the administration of an alum-adjuvanted control vaccine. Group 1 mice, vaccinated with the water-free/liposome/P3C/hydrophobic carrier formulation, yielded significantly enhanced endpoint titers compared to those of group 2. Group 2 mice generated titers up to 1/512,000 (log 10 value of 5.71) and up to 1/256,000 (log 10 value of 5.41) at three and four weeks respectively (before boost) and up to 1/4,096,000 (log 10 equal to 6.61) at eight weeks post-vaccination (after boost). The presence of such antibody responses confirms a genuine immune response generated as a result of the vaccination. Group 1 mice, vaccinated with the vaccine corresponding to the invention, were able to generate endpoint titers reaching up to 1/2,048,000 (log 10 value of 6.31) at three and four weeks post-vaccination and 1/8,192,000 (a log 10 value of 6.91) at eight weeks post-immunization. These results indicate that single dose water-free/liposome/hydrophobic carrier formulations containing a palmitic acid adjuvant are capable of generating an enhanced in vivo immune response compared to a single (week 3 and week 4 data points) or boosted (week 8 data point), aqueous alum based control vaccine.

Example 2

Pathogen free, young adult female Balb/C mice were obtained from Charles River Laboratories (St Constant, QC, Canada) and were housed according to institutional guidelines with water and food ad libitum, under filter controlled air circulation.

The pertussis toxoid protein was sourced from Biocine (Connaught Biosciences, Toronto, ON, Canada). This multi-subunit protein has an approximate molecular weight of 106 Kilo-daltons and corresponds to an antigenic toxin produced by Bordetella pertussis, the causative bacteria of whooping cough. This protein, hereafter designated PT, was used as a model antigen to test the efficacy of vaccine formulations. PT was used at 1 microgram per 50 microliter dose.

Vaccine efficacy was assessed by live bacterial challenge with Bordetella pertussis. Mice were challenged by aerosol inoculation with $9.1 \times 10^8$ Bordetella pertussis, 56 days post-vaccination. Several mice were sacrificed immediately to establish baseline bacterial lung counts. Remaining mice were monitored and sacrificed at eight and fifteen days post-challenge and bacterial lung counts established.

To formulate vaccine corresponding to the invention, a 10:1 w:w homogenous mixture of DOPC and cholesterol (Lipoid GmbH, Germany) was hydrated in the presence of PT and Pam-3-Cys-Ser-(Lys)4 (SEQ ID NO: 1)(designated P3C) in phosphate buffer to form liposomes with encapsulated PT and P3C. In brief, 20 micrograms each of PT and P3C in 850 microliters of 50 millimolar phosphate buffer was added to 132 milligrams of the S100 lecithin/cholesterol mixture to form approximately one milliliter of a liposome suspension encapsulating the PT antigen and P3C adjuvant. The liposome preparation was then lyophilized using the Virtis Advantage freeze dryer (SP Industries, Warminister, Pa., USA). For every one milliliter of original liposome suspension containing rHA and P3C, 800 microliters of a mineral oil carrier equivalent to Freund's incomplete adjuvant (known as Montanide® ISA 51, supplied by Seppic, France) was used to reconstitute the lyophilized liposomes to form a water-free liposome suspension. Each vaccine dose consisted of 50 microliters of the above described formulation containing liposomes, PT antigen, P3C adjuvant, and the mineral oil carrier. This vaccine formulation will be referred to as water-free/liposome/P3C/hydrophobic carrier.

The efficacy of the water-free liposome formulation described above was compared to the efficacy of a control vaccine consisting of 1 microgram of PT and 100 micrograms of aluminum hydroxide adjuvant (Alhydrogel, Sigma, Mississauga, ON, Canada, hereafter named alum) in 100 microliters of 50 millimolar phosphate buffer (pH 7.0). One group of mice (N=11) were injected once (no boosting) with 1 microgram of PT antigen and 1 microgram of P3C adjuvant formulated in 50 microliters of water-free/liposome/P3C/hydrophobic carrier as described above. Group 2 mice (N=9) and group 3 mice (N=9) were vaccinated once or three times (day 0, day 21, and day 31) with 1 microgram of PT and 100 micrograms of alum adjuvant suspended in 100 microliters of phosphate buffer. Mice were vaccinated intramuscularly in the flank region. Group 4 mice (N=10) remained unvaccinated for the duration of the study. All mice were challenged on day 56 post-immunization and bacterial lung counts established 8 and 15 days post-challenge as described above.

The results of this experiment are shown in FIG. 2. Group 4 (naïve) mice were not able to clear the infection, bacterial counts were as high as $2.5 \times 10^5$ cfu per lung at 8 days post-challenge and $4.7 \times 10^3$ cfu per lung at 15 days post-challenge. Group 2 mice, vaccinated with one dose of the alum-adjuvanted control vaccine, had bacterial lung counts as high as $8.9 \times 10^3$ and $3.1 \times 10^2$ cfu per lung at 8 and 15 days post challenge respectively. Group 3 mice vaccinated with three doses of the control had lung counts as high as $3.5 \times 10^3$ and $1.8 \times 10^3$ cfu per lung at the same respective time points. Group 1 mice, vaccinated with a single dose of the vaccine corresponding to the invention, had a bacterial lung count as high as $6.2 \times 10^4$ cfu per lung at 8 days post-challenge and 0 cfu per lung in all animals at day 15 post-challenge. A single dose of the vaccine corresponding to the invention effectively protected the mice from bacterial challenge and allowed them to completely clear the infection from the lungs.

Example 3

Pathogen free, female New Zealand White rabbits, 2-3 kg in weight, were obtained from Charles River Laboratories (St Constant, QC, Canada) and were housed according to institutional guidelines with water and food ad libitum, under filter controlled air circulation.

The anthrax recombinant Protective Antigen was purchased from List Biologics (Campbell, Calif.). This recombinant protein has an approximate molecular weight of 83,000 daltons and corresponds to the protective antigen protein, a cell binding component of the three-protein exotoxin produced by a *Bacillus anthracis*. This recombinant protein, hereafter designated rPA, was used as a model antigen to test the efficacy of vaccine formulations. rPA was used at 8 micrograms per 100 microliter dose.

Vaccine efficacy was assessed by enzyme-linked immunosorbent assay (ELISA), a method that allows the detection of antigen-specific antibody levels in the serum of immunized animals. Performing the ELISA on sera collected from immunized mice on a regular interval (every four weeks for example), is useful for monitoring the antibody responses to a given vaccine formulation. ELISA was performed as outlined in Example 1, using rPA at 1 microgram/milliliter as the coating antigen.

To formulate vaccine corresponding to the invention, a 10:1 w:w homogenous mixture of DOPC lecithin and cholesterol (Lipoid GmbH, Germany) was hydrated in the presence of rPA and Pam-3-cys (P3C) to form liposomes with encapsulated rPA and P3C. In brief, 80 micrograms of rPA and 20 micrograms of P3C in 850 microliters of sterile water were added to 132 milligrams of the DOPC lecithin/cholesterol mixture to form approximately one milliliter of a liposome suspension encapsulating the rPA antigen and P3C adjuvant. After diluting to a sufficient quantity using sterile water, the liposome suspension was lyophilized using the Virtis Advantage freeze dryer (SP Industries, Warminster, Pa., USA). For every 1 milliliter of original liposome suspension containing rPA and P3C, 800 microliters of a mineral oil carrier equivalent to Freund's incomplete adjuvant (known as Montanide® ISA 51, supplied by Seppic, France) was used to reconstitute the lyophilized liposomes to form a water-free liposome suspension. Each vaccine dose consisted of 100 microliters of the above-described formulation containing liposomes, rPA antigen, P3C adjuvant, and the mineral oil carrier. This vaccine is designated Vaccine C (invention).

The efficacy of the vaccine formulation described above was compared to the efficacy of a control vaccine consisting of 8 micrograms of rPA and 350 micrograms of aluminum hydroxide (Alhydrogel) adjuvant (Sigma, Mississauga, ON, Canada) in 100 microliters of sterile water. One group of rabbits (N=8) were injected once (no boosting) with 8 micrograms of rPA antigen and 2 micrograms of P3C adjuvant formulated in 100 microliters of vaccine formulation as described above (Group 1). Group 2 rabbits (N=8) were vaccinated three times (day 0, 28 and 84) with 8 microgram of rPA and 350 micrograms of alum adjuvant suspended in sterile water. All rabbits were vaccinated intramuscularly in the right gastrocnemius muscle and serum samples were collected at 3, 4, 8, 12 16, 20 and 24 weeks post-immunization. rPA antibody titers in these sera were examined by ELISA as described above.

The results of this experiment are shown in FIG. 3. Group 2 rabbits generated a detectable antigen-specific antibody response following the administration of an alum-adjuvanted control vaccine. Group 1 rabbits, vaccinated with the Vaccine C formulation, yielded significantly enhanced endpoint titers compared to those of group 2, at the early (pre-boost) time points. Group 2 rabbits generated titers up to 1/64,000 (average log 10 value of 4.66) and up to 1/256,000 (average log 10 value of 4.73) at three and four weeks respectively (before boost) and up to 1/2,048,000 (average log 10 equal to 5.86) at eight weeks post-vaccination (after boost). The presence of such antibody responses confirms a genuine immune response generated as a result of the vaccination. Group 1 rabbits, vaccinated with the vaccine corresponding to the invention, were able to generate endpoint titers reaching up to 1/2,048,000 (average log 10 value of 6.20 and 6.09) at three and four weeks post-vaccination and 1/8,192,000 (average log 10 value of 6.53) at eight weeks post-immunization. These results showing that single dose liposome/hydrophobic carrier formulations containing a Pam-3-Cys adjuvant are capable of generating on average 34.6 times and 22.9 times (at three and four weeks respectively) more antibodies in vivo than could be achieved with an aqueous alum control vaccine, demonstrate an ability to produce a surprisingly strong immune response as early as three weeks following a single vaccination.

Example 4

Pathogen free, female CD1 mice, 6-8 weeks of age, were obtained from Charles River Laboratories (St Constant, QC, Canada) and were housed according to institutional guidelines with water and food ad libitum, under filter controlled air circulation.

The H5N1 recombinant hemagglutinin protein was purchased from Protein Sciences (Meridien, Conn., USA). This recombinant protein has an approximate molecular weight of 72,000 daltons and corresponds to the hemagglutinin glycoprotein, an antigenic protein present on the surface of the H5N1 influenza virus. This recombinant protein, hereafter designated rHA, was used as a model antigen to test the efficacy of vaccine formulations. rHA was used at 1 microgram per 50 microliter dose.

Vaccine efficacy was assessed by enzyme-linked immunosorbent assay (ELISA), a method that allows the detection of antigen-specific antibody levels in the serum of immunized animals. Performing the ELISA on sera collected from immunized mice on a regular interval (every four weeks for example), is useful for monitoring the antibody responses to a given vaccine formulation. ELISA was carried out as described in Example 1.

To formulate vaccine corresponding to the invention, a 10:1 w:w homogenous mixture of S100 lecithin and cholesterol (Lipoid GmbH, Germany) was hydrated in the presence of rHA and Pam-3-Cys (P3C) in phosphate buffer to form liposomes with encapsulated rHA and P3C. In brief, 20 micrograms each of rHA and P3C in 850 microliters of 50 millimolar phosphate buffer was added to 132 milligrams of the S100 lecithin/cholesterol mixture to form approximately one milliliter of a liposome suspension encapsulating the rHA antigen and P3C adjuvant. The liposome preparation was diluted to a sufficient quantity with sterile water and then lyophilized using the Virtis Advantage freeze dryer (SP Industries, Warminister, Pa., USA). For every one milliliter of original liposome suspension containing rHA and P3C, 800 microliters of the mineral oil carrier (Montanide® ISA 51, supplied by Seppic, France) was used to reconstitute the lyophilized liposomes to form a water-free liposome suspension. Each vaccine dose consisted of 50 microliters of the above described formulation containing liposomes, rHA antigen, P3C adjuvant, and the mineral oil carrier. This vaccine formulation will be referred to as liposome/P3C/hydrophobic carrier. This formulation was used to vaccinate Group 1 mice (n=10).

Group 2 mice (n=10) were treated with 1 microgram of rHA and 1 microgram of P3C per 50 microliter dose, in the absence of liposomes/hydrophobic carrier. Group 3 mice (n=10) were treated with 1 microgram rHA and 1 microgram of P3C per 50 microliter dose formulated as an aqueous/liposome/P3C vaccine, in the absence of hydrophobic carrier. Group 4 mice (n=10) were treated with 1 microgram of rHA formulated as a liposome/hydrophobic carrier vaccine, in the absence of P3C. All mice were vaccinated intramuscularly in the flank region and serum samples were collected at 3, 4, 8, 12, 16 and 20 weeks post-immunization. rHA antibody titers in these sera were examined by ELISA as described.

The efficacies of these vaccine formulations were tested to evaluate the relative contribution of the components of these vaccine formulations (see FIG. 4). The titres from mice in all control groups (groups 2, 3 and 4) were consistently lower than the titres from group 1, vaccinated with Vaccine A, indicating that all components of this formulation are may be important for enhanced immunogenicity. For example, at week 8 post-vaccination, mice in group 1 (vaccinated with Vaccine A) were able to generate endpoint titers reaching up to 1/2,048,000 (average log 10 value of 5.65), whereas mice in group 2, 3 and 4 were able to generate endpoint titers of 1/64,000 (average log 10 value of 4.41), 1/128,000 (average log 10 value of 4.44) and 1/128,000 (average log 10 value of 4.69), respectively. The titers generated by mice in group one were significantly higher (p<0.0001, by one way analysis of variance) than the titers generated in any of the three control vaccine groups. This indicates an involvement of all components of vaccine formulation A, specifically antigen, liposomes, a palmitic acid adjuvant and a hydrophobic carrier, in simulating maximal immunogenicity of this formulation.

Example 5

Pathogen free, female Balb/C mice, 6-12 weeks of age, were obtained from Charles River Laboratories (St Constant, QC, Canada) and were housed according to institutional guidelines with water and food ad libitum, under filter controlled air circulation.

The antigen used in vaccine formulations was a heat inactivated Influenza strain A/PR/8/34 (H1N1). A viral stock was prepared by propagation in chicken eggs. An aliquot of A/PR/8/34 viral stock was quickly thawed and placed in a 56 degree Celcius water bath for 30 minutes to allow heat inactivation of the virus.

Vaccines were administered on day zero under isoflurane anesthetic, intramuscularly into the thigh muscle (one vaccine dose was divided into two injections, one per leg). The mice were weighed during the week after vaccination to ensure the vaccine itself did not cause illness.

On day 28, the mice were anesthetized using isoflurane and inoculated intranasally with 10×MLD50 of virus (two separate administrations of 25 microliters each divided equally into each nostril). The mice were then monitored for 10 days by measuring weight, temperature, and hydration, and by observing appearance, posture, and behavior. Mice that reached pre-determined points of morbidity were euthanized.

Mice in group 1 (n=10) were vaccinated with saline only and served as a negative control vaccine.

Mice in group 2 (n=10) were vaccinated with $2.56 \times 10^3$ TCID50 of heat inactivated Influenza strain A/PR/8/34 (H1N1) formulated in Alhydrogel.

Mice in group 3 (n=10) were vaccinated with a liposome/P3C/hydrophobic carrier vaccine. Briefly, a 10:1 (w:w) homogenous mixture of S100 lecithin and cholesterol (Lipoid GmbH, Germany) was hydrated in the presence of heat inactivated Influenza strain A/PR/8/34 and sterile water to form approximately 850 microliters of liposomes with encapsulated antigen. Pam-3-Cys (P3C) adjuvant was then added, liposomes mixed well, and the mixture diluted to a sufficient quantity with sterile water before being lyophilized using the Virtis Advantage freeze dryer (SP Industries, Warminister, Pa., USA). For every 1 milliliter of original liposome suspension containing A/PR/8/34 and P3C, 800 microliters of a mineral oil carrier (Montanide® ISA 51, Seppic, France) was used reconstitute the lyophilized liposomes to form a water-free liposome suspension. Each dose volume was 50 microliters and contained liposomes, influenza strain A/PR/8/34 ($2.56 \times 10^3$ TCID50), P3C (1 microgram), and the mineral oil carrier.

Figure 5:
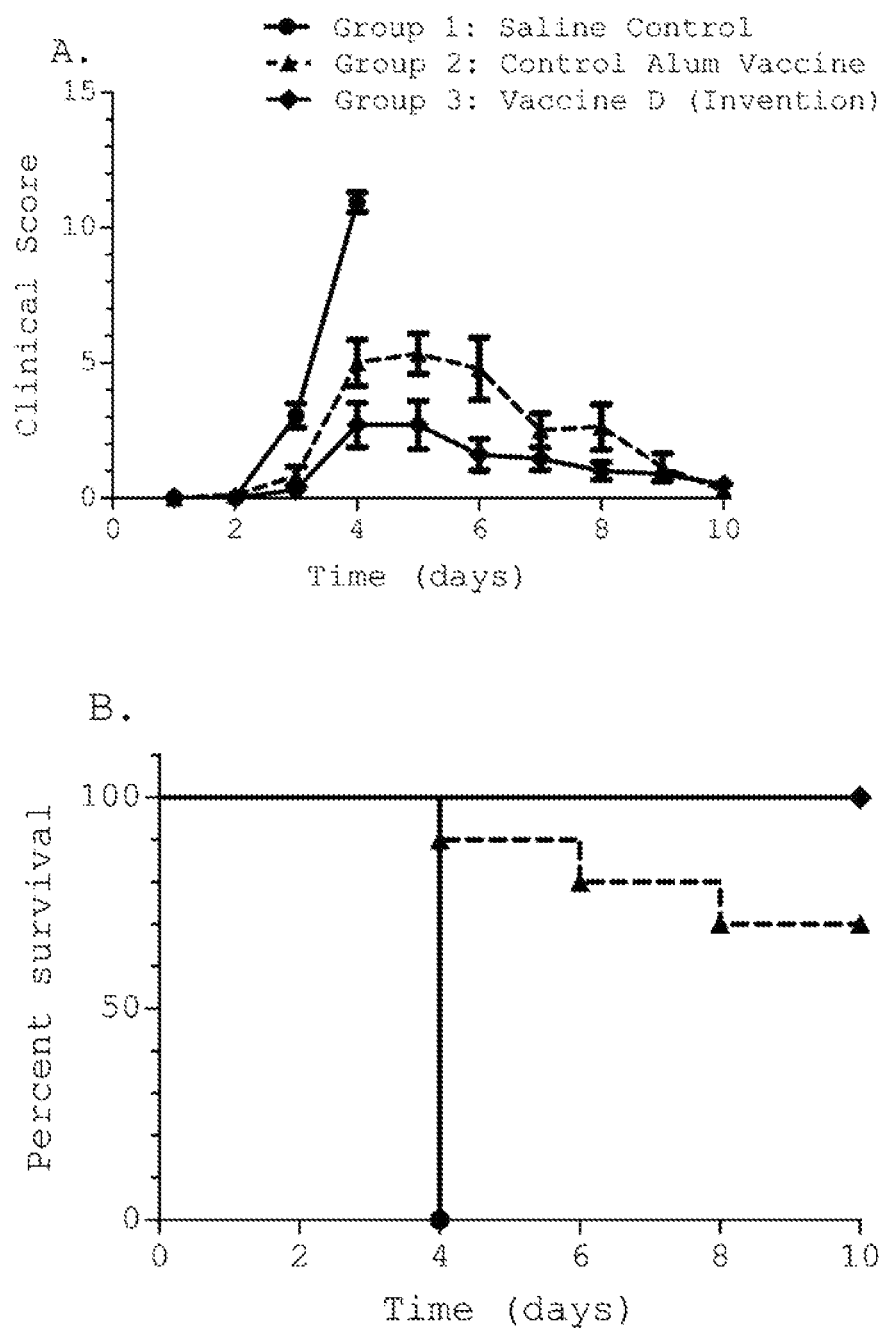
FIG. 5 illustrates that Vaccine D of the invention, comprising a lipid-based adjuvant (i.e. Pam-3-Cys), is capable of enhancing the immune response to inactivated viral vaccine formulations. Panel (A) shows the clinical score and Panel (B) shows the overall survival of mice challenged with A/PR/8/34 (H1N1) influenza 28 days after a single vaccination. Group 1 mice were treated with 50 microliters of saline. Group 2 mice were treated with 50 microliters of $2.56 \times 10^3$ TCID50 A/PR/8/34 with alum. Group 3 mice were treated with 50 microliters of $2.56 \times 10^3$ TCID50 A/PR/8/34 and 1 microgram Pam-3-Cys formulated as a liposome/P3C/hydrophobic carrier vaccine (Vaccine D). Following viral challenge, clinical signs for each mouse were followed every day for 10 days, and scored on the basis of physical appearance, posture, activity level/behavior, body temperature, body weight and hydration. Any mouse with a score of >12 (out of a total possible 18) was euthanized.
Figure 6:
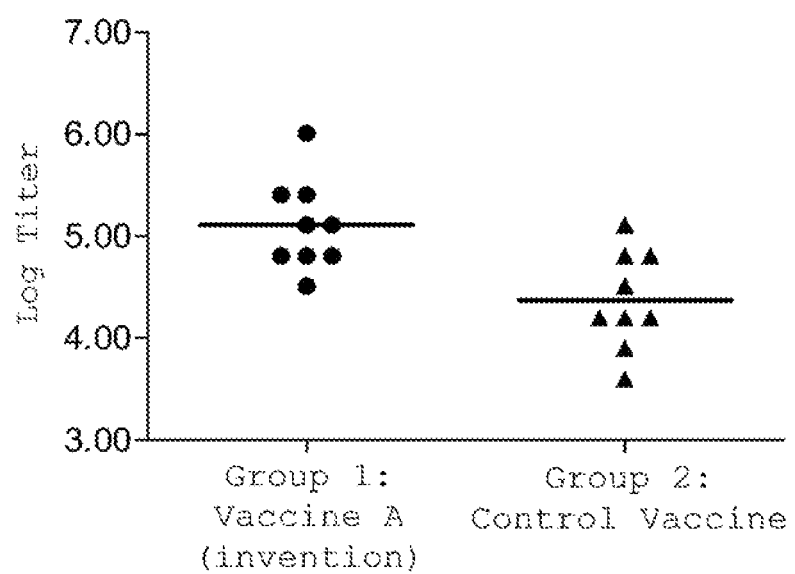
FIG. 6 illustrates that Vaccine A of the invention is capable of stimulating a specific immune response which is significantly stronger than a comparable vaccine prepared with a different adjuvant (liposomes/IMQ/hydrophobic carrier). Two groups of mice (N=9) were vaccinated as follows: Group 1 mice were vaccinated with a single dose of 1 microgram rHA and 1 microgram Pam-3-Cys in a 50 microliter dose formulated as a liposome/P3C/hydrophobic carrier vaccine (Vaccine A). Group 2 mice were treated with 1 microgram of rHA and 1 microgram of Imiquimod per 50 microliter dose formulated as a liposome/IMQ/hydrophobic carrier vaccine (Control Vaccine). Humoral immune responses were measured by ELISA as described above. For each treatment group, the log 10 values of the endpoint antibody titers were calculated. Statistical analysis performed by unpaired t-test, P<0.005.
Figure 7:
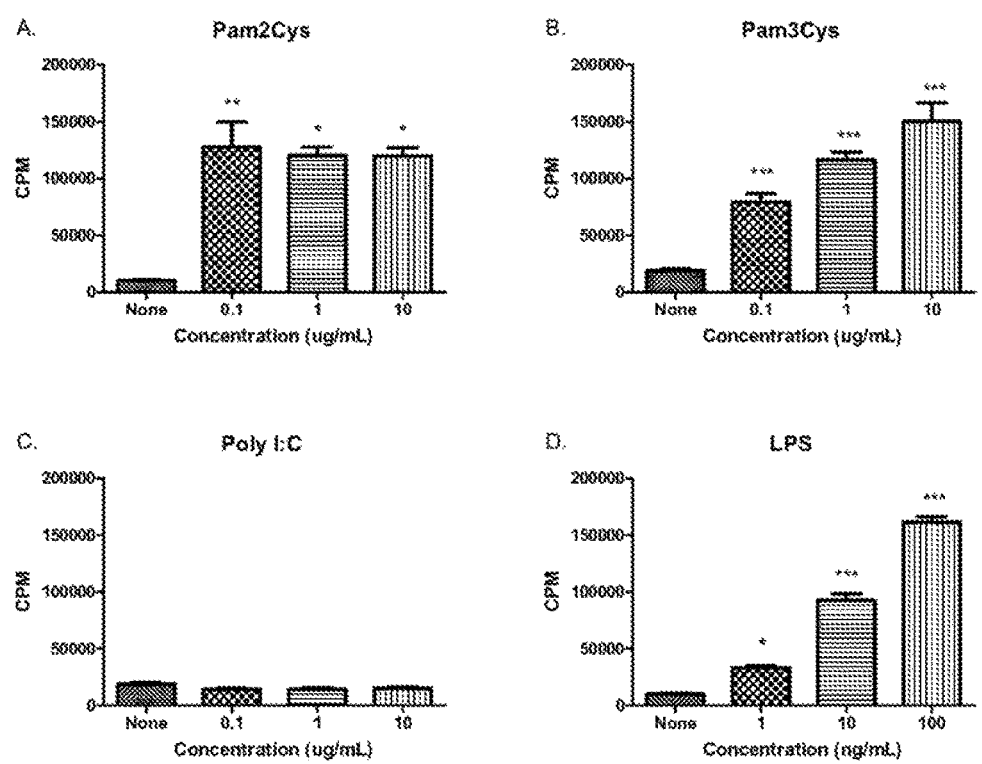
FIG. 7 illustrates that both Pam3Cys and Pam2Cys are capable of inducing potent proliferation of B cells. Purified B cells from C57BL6 mice were stimulated for three days in vitro with Pam2Cys (A), Pam3Cys (B), Poly I:C (C) or LPS (D) at three different concentrations in the presence of anti-Ig & anti-CD40. Proliferation was measured by [$^3$H]-thymidine incorporation, quantified as counts per minute (CPM). N=2-10, statistical analysis performed by ANOVA.

The results of this experiment are shown in FIG. 5. Group 1 mice vaccinated with saline alone rapidly developed clinical signs of influenza infection and all succumbed to infection by day four. The mice in group 2, vaccinated with antigen formulated in Alhydrogel, demonstrated moderately severe clinical symptoms upon influenza infection, with 30% of animals succumbing to infection. However, the mice in group 3, vaccinated with the liposome/P3C/hydrophobic carrier vaccine, had relatively mild clinical symptoms and 100% survived influenza infection.

These observations demonstrate that Pam-3-Cys formulated in the vaccine of the invention can enhance the immune response to inactivated viral vaccine formulations, as demonstrated by enhanced control of the virus upon infection.

Example 6

Pathogen free, female CD1 mice, 6-8 weeks of age, were obtained from Charles River Laboratories (St Constant, QC, Canada) and were housed according to institutional guidelines with water and food ad libitum, under filter controlled air circulation.

As in Examples 1 and 4, H5N1 recombinant hemagglutinin protein, corresponding to the hemagglutinin glycoprotein on the surface of the H5N1 influenza virus, was purchased from Protein Sciences (Meridien, Conn., USA). This recombinant protein, hereafter designated rHA, was used as a model antigen to test the efficacy of vaccine formulations. rHA was used at 1 microgram per 50 microliter dose.

Vaccine efficacy was assessed by enzyme-linked immunosorbent assay (ELISA), a method that allows the detection of antigen-specific antibody levels in the serum of immunized animals. Performing the ELISA on sera collected from immunized mice on a regular interval (every four weeks for example), is useful for monitoring the antibody responses to a given vaccine formulation. ELISA was carried out as described in Example 1.

Both vaccines in this example were formulated as described in Example 4. In summary, for the vaccine corresponding to the invention, rHA antigen and Pam-3-Cys (P3C) adjuvant in 50 millimolar phosphate buffer were used to hydrate S100 lecithin and cholesterol. The final liposome preparation was lyophilized and then reconstituted with ISA51. The final vaccine consisted of 50 microliters of a formulation containing liposomes, 1 microgram of rHA antigen, 1 microgram P3C of adjuvant, and the mineral oil carrier. This vaccine formulation will be referred to as liposome/P3C/hydrophobic carrier. This formulation was used to vaccinate Group 1 mice (n=9).

Group 2 mice (n=9) were treated with a formulation containing liposomes, 1 microgram of rHA, 1 microgram of Imiquimod (IMQ) adjuvant, and the mineral oil carrier. This vaccine will be referred to as liposome/IMQ/hydrophobic carrier. In summary, rHA antigen and IMQ adjuvant (InvivoGen, San Diego, Calif., USA) in 50 millimolar phosphate buffer were used to hydrate S100 lecithin and cholesterol. The final liposome preparation was lyophilized and then reconstituted with ISA51.

All mice were vaccinated intramuscularly in the flank region and serum samples were collected at 4 weeks post-immunization. rHA antibody titers in these sera were examined by ELISA as described in Example 1.

The efficacies of these vaccine formulations were tested to evaluate the relative contribution of the P3C adjuvant in the liposome/hydrophobic carrier formulation (see FIG. 6). Group 2 mice generated a detectable antigen-specific antibody response following the administration of an Imiquimod-adjuvanted control vaccine. Group 1 mice, vaccinated with the liposome/P3C/hydrophobic carrier formulation, yielded significantly enhanced endpoint titers compared to those of group 2 (P<0.005). Group 2 mice generated titers up to 1/128,000 (log 10 value of 5.11) at 28 days (4 weeks) post-vaccination. As noted in example 1, the presence of such antibody responses confirms a genuine immune response generated as a result of the vaccination. Group 1 mice, vaccinated with the vaccine corresponding to the invention, were able to generate endpoint titers reaching up to 1/1,024,000 (log 10 value of 6.01) at four weeks post-immunization. This data indicates that the vaccine corresponding to the invention (liposomes/P3C/hydrophobic carrier) is able to stimulate a specific humoral immune response which is significantly stronger than a comparable vaccine prepared with a different adjuvant (liposomes/IMQ/hydrophobic carrier).

Example 7

Pathogen free, female C57BL6 mice, 6-8 weeks of age, were obtained from Charles River Laboratories (St Constant, QC, Canada) and were housed according to institutional guidelines with water and food ad libitum, under filter controlled air circulation.

Untreated "naïve" mice were terminated and spleens collected. A single cell suspension was prepared from the splenocytes and red blood cells lysed using ACK lysis buffer. B cells were isolated using a negative selection magnetic isolation kit from Miltenyi (Auburn, Calif., USA). Cells were resuspended in complete RPMI media containing 10% FBS, 1% penicillin-streptomycin, 1% L-glutamine and 0.1% b-mercaptoethanol (c-RPMI) at a final concentration of $2\times10^6$ cells/mL. B cells were added to wells of a 96-well plate ($2\times10^5$ cells/well) with anti-Ig (2.5 ug/mL; BD Biosciences, Mississauga, Canada) and anti-CD40 (1 ug/mL; BD Biosciences). B cells were stimulated with the following adjuvants in triplicate: Pam2Cys (EMC Microcollections, Tuebingen, Germany), Pam3Cys (EMC Microcollections), Poly I:C (Thermo Fisher, MI, USA) and LPS (Sigma-Aldrich, Oakville, Canada), or no adjuvant. Each adjuvant was dosed at 10 ug/mL, 1 ug/mL and 0.1 ug/mL, except LPS which was dosed at 100 ng/mL, 10 ng/mL and 1 ng/mL. Cells were incubated at 37° C./5% $CO_2$ for 3 days. Eighteen hours before the end of the experiment, [$^3$H]-thymidine was added to each well at a final concentration of 0.2 uCi/well. Plates were harvested using Titertek Cell Harvester (Skatron Instruments, Sterling, Va., USA) onto filter membranes which were then counted with Beckman LS6000IC liquid scintillation counter (Beckman Coulter Inc., Mississauga, ON, Canada). Proliferation was quantified by averaging the triplicate counts per minute (CPM) representing the incorporation of [3H]-thymidine.

Results of adjuvant stimulation of B cells show that while Pam3Cys and Pam2Cys can induce potent proliferation of B cells, Poly I:C does not (see FIG. 7). LPS, included as a positive control, is known to induce B cell proliferation of low concentrations. Based on these results, it is reasonable to expect that vaccines containing Pam2Cys or Pam3Cys would have similar effects on B cells in vivo, and would be capable of facilitating the production of similar levels of antigen specific antibodies.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or"

should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to encompass the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

As used herein, whether in the specification or the appended claims, the transitional terms "comprising", "including", "carrying", "having", "containing", "involving", and the like are to be understood as being inclusive or open-ended (i.e., to mean including but not limited to), and they do not exclude unrecited elements, materials or method steps. Only the transitional phrases "consisting of" and "consisting essentially of", respectively, are closed or semi-closed transitional phrases with respect to claims. The transitional phrase "consisting of" excludes any element, step, or ingredient which is not specifically recited. The transitional phrase "consisting essentially of" limits the scope to the specified elements, materials or steps and to those that do not materially affect the basic characteristic(s) of the invention disclosed and/or claimed herein.

---

The invention claimed is:

1. A method for inducing a humoral immune response in a subject, said method comprising administering to the subject an effective amount of a water-free composition comprising an adjuvant that activates or increases the activity of toll-like receptor 2 (TLR2), dehydrated liposomes, and an antigen, reconstituted in a carrier comprising a continuous phase of a hydrophobic substance, wherein the antigen comprises a B cell epitope and is capable of inducing a humoral immune response;

wherein the adjuvant comprises dipalmitoyl-S-glyceryl-cysteine (PAM$_2$Cys) or tripalmitoyl-S-glyceryl-cysteine (PAM$_3$Cys);

and wherein the antigen is not coupled covalently to the adjuvant.

2. The method of claim 1, wherein the humoral immune response is induced against an antigen of a pathogenic biological agent; a surface-bound cancer antigen; or an antigen associated with a neurodegenerative disease.

3. The method of claim 1, wherein the humoral immune response is induced to generate neutralizing antibodies against a toxin, virus, bacterium or allergen.

4. The method of claim 1, wherein the adjuvant activates or increases the activity of TLR2 by interacting with a TLR2 dimer of TLR1/2 or TLR2/6.

5. The method of claim 1, wherein the adjuvant is PAM$_2$Cys-Ser-(Lys)4 (SEQ ID NO:1), PAM$_3$Cys-Ser-(Lys)4 (SEQ ID NO:1), PAM$_3$Cys-SKKKK(SEQ ID NO:1) (β-irradiated), R-PAM$_3$Cys-SKKKK (SEQ ID NO:1), S-PAM$_3$Cys-SKKKK (SEQ ID NO:1), PAM$_3$Cys-SKKKK (Biotin-Aca-Aca) (SEQ ID NO:1), PAM$_3$Cys-SKKKK (Fluorescein-Aca-Aca) (SEQ ID NO:1), PAM$_3$Cys-SKKKK (Rhodamine-Aca-Aca) (SEQ ID NO:1), PAM$_3$Cys-SKKKK-FLAG-tag (SEQ ID NO:1), PAM$_3$Cys-SSNAK-IDQLSSDVQT (SEQ ID NO:4), PAM$_3$Cys-SSNK-STTGSGETTTA (SEQ ID NO:5), PAM$_3$Cys-SSTKPVSQDTSPKPA (SEQ ID NO:6), PAM$_3$Cys-SSGSKPSGGPLPDAK (SEQ ID NO:7), PAM$_3$Cys-SSGNKSAPSSSASSS (SEQ ID NO:8), PAM$_3$Cys-GSHQMKSEGHANMQL (SEQ ID NO:9), PAM$_3$Cys-SSSNNDAAGNGAAQT (SEQ ID NO:10), PAM$_3$Cys-KQNVSSLDEKNSVSV (SEQ ID NO:11), PAM$_3$Cys-NNSGKDGNTSANSAD (SEQ ID NO:12), PAM$_3$Cys-NNGGPELKSDEVAKS (SEQ ID NO:13), PAM$_3$Cys- SQEPAAPAAEATPAG (SEQ ID NO:14), PAM₃Cys-SSSKSSDSSAPKAYG (SEQ ID NO:15), PAM₃Cys-AQEKEAKSELDYDQT (SEQ ID NO:16), PAM₂Cys-SKKKK (mixture of RR and RS stereoisomers) (SEQ ID NO:1), R-PAM₂Cys-SKKKK (RR stereoisomer) (SEQ ID NO:1), S-PAM₂Cys-SKKKK (RS stereoisomer) (SEQ ID NO:1), PAM₂Cys-SKKKK(Biotin-Aca-Aca)-NH₂ (SEQ ID NO:1), PAM₂Cys-SKKKK(Fluorescein-Aca-Aca)-NH₂ (SEQ ID NO:1), PAM₂Cys-SKKKK(Rhodamine-Aca-Aca)-NH₂ (SEQ ID NO:1), PAM₂Cys-SKKKK-FLAG-tag (SEQ ID NO:1), FSL-1 (Pam2CGDPKHPKSF) (SEQ ID NO:2), or FSL-1-Ala.

6. The method of claim 5, wherein the adjuvant is PAM₂Cys-Ser-(Lys)4 (SEQ ID NO: 1) or PAM₃Cys-Ser-(Lys)4 (SEQ ID NO:1).

7. The method of claim 6, wherein the adjuvant is PAM₃Cys-Ser-(Lys)4 (SEQ ID NO:1).

8. The method of claim 1, wherein the antigen is a polypeptide or a carbohydrate.

9. The method of claim 1, wherein the B cell epitope is derived from a virus or bacteria.

10. The method of claim 9, wherein the B cell epitope is derived from influenza virus, *Bordetella pertussis*, or *Bacillus anthracis*.

11. The method of claim 10, wherein the B cell epitope is an epitope of a hemagglutinin protein of H5N1 influenza virus, an epitope of pertussis toxoid protein, or an epitope of an anthrax recombinant protective antigen.

12. The method of claim 1, wherein the antigen is encapsulated within the dehydrated liposomes or both the antigen and the adjuvant are encapsulated in the dehydrated liposomes, reconstituted in the continuous phase of a hydrophobic substance.

13. The method of claim 1, wherein the liposomes are non-cationic liposomes, wherein the lipids of the liposomes consist of neutral lipids, negatively charged lipids or a mixture thereof.

14. The method of claim 1, wherein the composition is capable of inducing a humoral immune response with a single dose.

15. The method of claim 2, wherein the pathogenic biological agent is selected from the group consisting of influenza virus, respiratory syncytial virus, *Bordetella pertussis*, *Bacillus anthracis*, and species of the genus *Plasmodium*.

16. The method of claim 1, wherein the liposomes are comprised of phospholipids and cholesterol.

17. The method of claim 1, wherein the carrier is a mannide oleate in mineral oil solution.

18. The method of claim 17, wherein the carrier is Montanide® ISA 51.

19. The method of claim 1, wherein the antigen is selected from the group consisting of H5N1 recombinant hemagglutinin protein, pertussis toxoid protein, anthrax recombinant Protective Antigen and heat inactivated Influenza strain A/PR/8/34 (H1N1).

20. The method of claim 1, wherein the liposomes comprise S100 lecithin and cholesterol or dioleoyl-phosphatidylcholine (DOPC) and cholesterol; the carrier is Montanide® ISA 51; and the adjuvant is PAM₃Cys-Ser-(Lys)4 (SEQ ID NO:1).

21. The method of claim 20, wherein the antigen is selected from the group consisting of H5N1 recombinant hemagglutinin protein, pertussis toxoid protein, anthrax recombinant Protective Antigen and heat inactivated Influenza strain A/PR/8/34 (H1N1).

* * * * *